US008822187B1

(12) United States Patent
Chappell et al.

(10) Patent No.: US 8,822,187 B1
(45) Date of Patent: Sep. 2, 2014

(54) POLYPEPTIDES, NUCLEIC ACID MOLECULES, AND METHODS FOR SYNTHESIS OF TRITERPENES

(75) Inventors: Joe Chappell, Lexington, KY (US); Thomas D. Niehaus, Lexington, KY (US); Shigeru Okada, Tokyo (JP); Timothy P. Devarenne, Bryan, TX (US); David S. Watt, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 151 days.

(21) Appl. No.: 13/458,668

(22) Filed: Apr. 27, 2012

Related U.S. Application Data

(60) Provisional application No. 61/517,876, filed on Apr. 27, 2011.

(51) Int. Cl.
*C12P 5/00* (2006.01)
*C12P 5/02* (2006.01)
*C12N 9/10* (2006.01)

(52) U.S. Cl.
USPC ............................ 435/166; 435/167; 435/193

(58) Field of Classification Search
CPC ............................. C12P 5/007; C12N 9/1085
USPC .......................................... 435/166, 167, 193
See application file for complete search history.

(56) References Cited

U.S. PATENT DOCUMENTS

| 7,985,568 B2 * | 7/2011 | Chappell et al. ............... 435/166 |
| 2010/0009423 A1 | 1/2010 | Chappell et al. |
| 2011/0294182 A1 | 12/2011 | Chappell et al. |

OTHER PUBLICATIONS

Xu MM, Wilderman PR, Peters RJ (2007) Following evolution's lead to a single residue switch for diterpene synthase product outcome. Proc Natl Acad Sci USA 104:7397-7401.
Xu MM, et al. (2007) Functional characterization of the rice kaurene synthase-like gene family. Phytochemistry 68:312-326.
Zhang DL, Poulter CD (1995) Biosynthesis of non-head-to-tail isoprenoids—synthesis of 1'-1-structures and 1'-3-structures by recombinant yeast squalene synthase. J Amer Chem Soc 117:1641-1642.
Agnew WS, Popjak G (1978) Squalene synthetase—stoichiometry and kinetics of presqualene pyrophosphate and squalene synthesis by yeast microsomes. J Biol Chem 253:4566-4573.
Banerjee A, Sharma R, Chisti Y, Banerjee UC (2002) Botryococcus braunii: A renewable source of hydrocarbons and other chemicals. Crit Rev Biotech 22:245-279.
Bergstrom JD, et al. (1993) Zaragozic acids—a family of fungal metabolites that are picomolar competitive inhibitors of squalene synthase. Proc Nati Acad Sci USA 90:80-84.
Blagg BSJ, Jarstfer MB, Rogers DH, Poulter CD (2002) Recombinant squalene synthase. A mechanism for the rearrangement of presqualene diphosphate to squalene. J Amer Chem Soc 124:8846-8853.
Brown AC, Knights BA, Conway E (1969) Hydrocarbon content and its relationship to physiological state in green alga botryococcus braunii. Phytochemistry 8:543-547.
Cao R, et al. (2010) Diterpene cyclases and the nature of the isoprene fold. Proteins 78:2417-2432.
Derenne S, et al. (1997) Chemical structure of the organic matter in a pliocene maar-type shale: Implicated Botryococcus race strains and formation pathways. Geochim Cosmochim Acta 61:1879-1889.
Field B, Osbourn AE (2008) Metabolic diversification—independent assembly of operon-like gene clusters in different plants. Science 320:543-547.
Gelpi E, Oro J, Schneide HJ, Bennett EO (1968) Olefins of high molecular weight in 2 microscopic algae. Science 161:700-701.
Glikson M, Lindsay K, Saxby J (1989) Botryococcus—a planktonic green-alga, the source of petroleum through the ages—transmission electron microscopical studies of oil shales and petroleum source rocks. Org Geochem 14:595-608.
Gu PD, Ishii Y, Spencer TA, Shechter I (1998) Function-structure studies and identification of three enzyme domains involved in the catalytic activity in rat hepatic squalene synthase. J Biol Chem 273:12515-12525.
Haralampidis K, et al. (2001) A new class of oxidosqualene cyclases directs synthesis of antimicrobial phytoprotectants in monocots. Proc Natl Acad Sci USA 98:13431-13436.
Hillen LW, Pollard G, Wake LV, White N (1982) Hydrocracking of the oils of Botryococcus braunii to transport fuels. Biotech Bioeng 24:193-205.
Huang Z, Poulter CD (1989) Tetramethylsqualene, a triterpene from Botryococcus braunii var showa. Phytochemistry 28:1467-1470.
Jandrositz A, Turnowsky F, Hogenauer G (1991) The gene encoding squalene epoxidase from Saccharomyces cerevisiae—cloning and characterization. Gene 107: 155-160.
Jarstfer MB, Zhang DL, Poulter CD (2002) Recombinant squalene synthase. Synthesis of non-head-to-tail isoprenoids in the absence of NADPH. J Amer chem Soc 124:8834-8845.
Jarstfer MB, Blagg BSJ, Rogers DH, Poulter CD (1996) Biosynthesis of squalene. Evidence for a tertiary cyclopropylcarbinyl cationic intermediate in the rearrangement of presqualene diphosphate to squalene. J Amer Chem Soc 118:13089-13090.
Lin F-Y, et al. (2010) Mechanism of action and inhibition of dehydrosqualene sythase. Proc Natl Acad Sci USA 107:21337-21342.
Liu CI, et al. (2008) A cholesterol biosynthesis inhibitor blocks Staphylococcus aureus virulence. Science 319:1391-1394.
Mastalerz M, Hower JC (1996) Elemental composition and molecular structure of Botryococcus alginite in westphalian cannel coals from Kentucky. Org Geochem 24:301-308.
Metzger P, Largeau C (2005) Botryococcus braunii: A rich source for hydrocarbons and related ether lipids. Appl Microbiol Biotech 66:486-496.
Metzger P, Rager MN, Largeau C (2007) Polyacetals based on polymethylsqualene diols, precursors of algaenan in botryococcus braunii race b. Org Geochem 38:566-581.
Metzger P, Berkaloff C, Casadevall E, Coute A (1985) Alkadiene-producing and botryococcene-producing races of wild strains of Botryococcus braunii. Phytochemistry 24:2305-2312.

(Continued)

*Primary Examiner* — Tekchand Saidha
(74) *Attorney, Agent, or Firm* — Stites & Harbison PLLC; Mandy Wilson Decker

(57) ABSTRACT

This application relates to the polypeptides, nucleic acid molecules, vectors, transfected cells, and methods for synthesis of triterpenes, including botryococcene.

7 Claims, 11 Drawing Sheets

(56) References Cited

OTHER PUBLICATIONS

Meyer E, Aglyamova GV, Wang S, Buchanan-Carter J, Abrego D, Metzger P (1999) Two terpenoid diepoxides from the green microalga Botryococcus braunii: Their biomimetic conversion to tetrahydrofurans and tetrahydropyrans. Tetrahedron 55:167-176.

Metzger P, Rager MN, Largeau C (2002) Botryolins A and B, two tetramethylsqualene triethers from the green microalga Botryococcus braunii. Phytochemistry 59:839-843. Colbourne JK, Willis BL, Matz MV (2009) Sequencing and de novo analysis of a coral larval transcriptome using 454 gsflx. BMC Genomics 10.

Moldowan JM, Seifert WK (1980) 1st discovery of botryococcane in petroleum. J Chem Soc-Chem Comm 912-914.

Nara T, Hshimoto T, Aoki T (2000) Evolutionary implications of the mosaic pyrimidine-biosynthetic pathway in eukaryotes. Gene 257:209-222.

Niehaus, et al. (2011) Identification of unique mechanisms for triterpene biosynthesis in Botryococcus braunii. PNAS 108(30):12260-12265.

Okada S, Murakami M, Yamaguchi K (1995) Hydrocarbon composition of newly isolated strains of the green microalga Botryococcus braunii. J Appl Phycol 7:555-559.

Okada S, Tonegawa I, Matsuda H, Murakami M, Yamaguchi K (1997) Braunixanthins 1 and 2, new carotenoids from the green microalga Botryococcus braunii. Tetrahedron 53:11307-11316.

Okada S, Devarenne TP, Chappell J (2000) Molecular characterization of squalene synthase from the green microalga Botryococcus braunii, race B. Arch Biochem Biophys 373:307-317.

Okada S, Devarenne TP, Murakami M, Abe H, Chappell J (2004) Characterization of botryococcene synthase enzyme activity, a squalene synthase-like activity from the green microalga Botryococcus braunii, race B. Arch Biochem Biophys 422: 110-118.

Pan JJ, Bugni TS, Poulter CD (2009) Recombinant squalene synthase. Synthesis of cyclopentyl non-head-to-tail triterpenes. J Org Chem 74:7562-7565.

Pandit J, et al. (2000) Crystal structure of human squalene synthase—a key enzyme in cholesterol biosynthesis. J Biol Chem 275:30610-30617.

Peters RJ (2010) Two rings in them all: The labdane-related diterpenoids. Nat Prod Rep 27:1521-1530.

Poulter CD (1990) Biosynthesis of non-head-to-tail terpenes—formation of 1'-1 and 1'-3 linkages. Acc Chem Res 23:70-77.

Prisic S' Xu MM, Wilderman PR, Peters RJ (2004) Rice contains two disparate ent-copalyl diphosphate synthases with distinct metabolic functions. Plant Physiol 136:4228-4236.

Radisky ES, Poulter CD (2000) Squalene synthase: Steady-state, pre-steady-state, and isotope-trapping studies. Biochemistry 39:1748-1760.

Rilling HC (1966) A new intermediate in biosynthesis of squalene. J Biol Chem 241:3233-3236.

Robinson GW, Tsay YH, Kienzle BK, Smithmonroy CA, Bishop RW (1993) Conservation between human and fungal squalene synthetases—similarities in structure, function, and regulation. Mol Cell Biol 13:2706-2717.

Sasiak K, Rilling HC (1988) Purification to homogeneity and some properties of squalene synthetase. Arch Biochem Biophys 260:622-627.

Song LS (2003) Detection of farnesyl diphosphate accumulation in yeast erg9 mutants. Anal Biochem 317:180-185.

Sun et al. (2009) Sensitive and specific elisa coated by tpn15-tpn17-tpn47 fusion protein for detection of antibodies to Treponema pallidum. Clin Chem Lab Med 47: 321-326.

Takahashi S, Yeo Y, Greenhagen BT, McMullin T, Song L, Maurina-Brunker J, Rosson R, Noel JP Chappell J. (2007) Metabolic engineering of sesquiterpene metabolism in yeast. Biotech Bioeng 97:170-181.

Toyomasu T, et al. (2000) Cloning of a full-length cDNA encoding ent-kaurene synthase from Gibberella fujikuroi: Functional analysis of a bifunctional diterpene cyclase. Biosci Biotechnol Biochem 64:660-664.

Traverse A (1955) Occurrence of the oil-forming alga Botryococcus in lignites and other tertiary sediments. Micropaleontology 1:343-350.

Wang et al. (2004) Strategies for gene disruptions and plasmid constructions in fission yeast. Methods 33: 199-205.

Weiss TL, et al. (2010) Raman spectroscopy analysis of botryococcene hydrocarbons from the green microalga Botryococcus braunii. J Biol Chem 285:32458-32466.

Xu MM, Hillwig ML, Prisic S, Coates RM, Peters RJ (2004) Functional identification of rice syn-copalyl diphosphate synthase and its role in initiating biosynthesis of diterpenoid phytoalexin/allelopathic natural products. Plant J 39:309-318.

\* cited by examiner

```
                            C   L       ☆SRSF
BSS    (1)  ---MGMLRWGVESLQNPDELIPVLRMIYADKFGKIK--PRDEDRGFCYEILNLMSRSFAI
SSL-1  (1)  MTMHQDHGVMKDLVKHPNEFPYLLQLAATTYGSPAAPIPREPDRAFCYNTLHTMSKGEPR
SSL-2  (1)  ------MVKLVEVLQHPIEIVPILQMLHKTYRAKRS--YKDPGLAFCYGMIQRWSRSFSV
SSL-3  (1)  -------MKLREVLQHPGEIIPLLQMMVMAYRRKRK--PQDPNLAWCWEILIKMSRSYVL
                                                             FLAP

VI L  R           ☆    ☆ ☆      ☆          K   L  F
                        FYL  LR DT EDD
BSS   (56)  VIQQLPAQLRDPVGIFYIVLRALDTVEDDMKIAATTKNIPLLPDFYEKISDRSFPMTACDQ
SSL-1 (61)  FVMFLPQELQDPICFYILLRALDTVEDDMNLKSETKISLLRVFHEHCSDRNWSMKSD-Y
SSL-2 (53)  VIQQLPDELRHPICVFYILLRALDTVEDDMNLPNEVKIPLLRTFHEHLFDRSWKLKCG-Y
SSL-3 (52)  VIQQLPEVLQDPICVNYIVLRGLDTLQDDMAIPAEKRVPLLLDYYNHIGDITWKPPCG-Y
              I              II

L           I  I  MG GMA            ☆
BSS  (116)  KDVIRLLDQYPKVTSVFLKLTPREQEIIADITKRMGNGMADEVHKGVPDTVGDYDLVCHY
SSL-1 (120) GIVADIMERFPLVVSVLEKLPPATIQTFRENVKYMGNGMADFI-DKQILTVDEYDLVCHY
SSL-2 (112) GPYVDLMENYPLVTDVFLTLSPGAQEVIRDSTRRMGNGMADFIGKKDEVHSVAEYDLVCHY
SSL-3 (111) GQYVELIEEYPRVTKEFLKLNKQDQQFITDMCMRLGAEMTVEL-KRDVLTVPDLDLMAFT
                                                                    III

VAG VG GL                   GLFLQK ☆NIIRDY ☆RD     R FW
BSS  (176)  VAGVVGLGLSQLFMASGLQSPSLTRSEDLSNHMGLFLQKTNIIRDYFEDINELPAPRMFW
SSL-1 (179) VAGSCGIAVIKVIQFNLATP-EADSYDFSNLGLLLQRANIITDYNEDINEEPRPRMFW
SSL-2 (172) VAGLVGSAVAKIFDSGLEKENLVAEVDLANNMEQFLQKTWIRDYLEDINEEPAPRMFW
SSL-3 (170) NNGFVAICLTKLWDRKFADPKLLDREDLSGHMAMFLGRINVIRDIKELVIED-PPRIWW
                III                              IV

P   W   Y           C            AL H    Y        F FCAI
BSS  (236)  PREIWGKYANNLAEFKDPANKAAAMCLNEMVTDALRHAVYCLQYMSMIEDPQIFNFCAI
SSL-1 (238) PQEIWGKYAEKLADFNEPENIDTAVKCLNHMVTDARHIEPSLKGMVYFTDKTVFRALAL
SSL-2 (232) PREIWGKYAQELADFKDPANEKAAVQCLNHMVTDALRHCEIGLNVIPLLQNIGILRSCLT
SSL-3 (229) PKEIWGKYLKDLRDIIKEEYQKEALACLNDILTDALRHIEPCLQYMEKVWDEGVFFFCAV
                                                                      V

PQ MA TL     N         VK R G
BSS  (296)  PQTMAFGTLSLCYNNYTIFTGPKAAVKLRRGTIAKLMYTSNNMFAMYRHFINFAEKLEVR
SSL-1 (298) LLVTAFGELSTLYMNPNVFKEK---VRQRKGRIARLVMSSRNVPGLFRTCIKLANNFESR
SSL-2 (292) PEVMGLRTLTLCYNNPQVFRG---VVKMRRGETAKLFMSIYDKRSFYQTYLRLANELEAK
SSL-3 (289) PELMSLATISVCYNNPKVFTG---VIKMERGETAKIFLSVTNMPALYKSFSAIAFEMEAK
                V                 NADPH

BSS  (356)  CNTETSEDPSVTITLEHLHKIKAACKAGLAR------TKDDTFDELRSRLLALTGGSFYL
SSL-1 (355) QKQETANDPTVAMIIKRLQSIQATCRDGLAKYDTPSGLKSFCAAPTPTK-----------
SSL-2 (349) CKGEASGDPMVATTLKHVHGIQKSCKAALSSKELLAKSGSALTDPAIRLLLLVGVVAYF
SSL-3 (346) QV---REDPNFALTVKRLQDVQALCKAGLAKSNGKVSAKGA---▲---------------

BSS  (410)  AWTYNFLDLAGPG---DLPTFLSVTQHWWSILIFLISIAVFFIPSRPSPRPTLSA--
SSL-1 (404) ------------------------------------------------------
SSL-2 (409) AYAFNLCDVPGEHGVRALGSILDLSQKGLAVASVALLLLVLLARSRLPLLTSASSKQ
SSL-3 (384) ------------------------------------------------------
```

FIG. 2

POLYPEPTIDES, NUCLEIC ACID MOLECULES, AND METHODS FOR SYNTHESIS OF TRITERPENES

RELATED APPLICATIONS

This application claims priority from U.S. Provisional Application Ser. No. 61/517,876 filed Apr. 27, 2011, the entire disclosure of which is incorporated herein by this reference.

GOVERNMENT INTEREST

This invention was made with government support under Grant No. CBET-0828817 awarded by the National Science Foundation and under grant number 2P20 RR020171 from the National Center for Research Resources of the National Institutes of Health. The government has certain rights in the invention.

TECHNICAL FIELD

The presently-disclosed subject matter relates to compositions and methods for triterpene synthesis, in particular botryococcene synthesis.

INTRODUCTION

*Botryococcus braunii* is a colony-forming, freshwater green algae reported to accumulate 30 to 86% of its dry weight as hydrocarbon oils (1). Three distinct races of *B. braunii* have been described based on the types of hydrocarbons that each accumulates (2). Race A accumulates fatty acid-derived alkadienes and alkatrienes (3), race L accumulates the tetraterpene lycopadiene (4), and race B accumulates triterpenes, predominately botryococcene, squalene and their methylated derivatives (5). The oils accumulate both in intracellular oil bodies and in association with an extracellular matrix (6), which in race B consists largely of long-chain, cross-linked biopolymers formed in part from acetalization of polymethylsqualene diols (7). Di- and tetra-methylated botryococcenes are generally the most abundant triterpenes accumulating in race B with smaller amounts of tetramethylated-squalene (8) and other structural derivatives of squalene and botryococcene that range from $C_{31}$ to $C_{37}$ accumulating to various levels in different strains and in response to variable culture conditions (9). Other polymethylated derivatives such as diepoxy-tetramethylsqualene (10), botryolins (11), and brauixanthins (12) have also been reported.

*B. braunii* race B has received significant attention because it is considered an ancient algal species dating back at least 500 MYA and is one of the few organisms known to have directly contributed to the existing oil and coal shale deposits found on Earth (13-15), accounting for up to 1.4% of the total hydrocarbon content in oil shales (16). Secondly, because the hydrocarbon oils of *B. braunii* race B are readily converted to starting materials for industrial chemical manufacturing and high quality fuels under standard hydrocracking/distillation conditions in yields approaching 97% (FIG. 1A) (17), race B has been considered a potential production host for renewable petrochemicals and biofuels. However, the slow growth habit of *B. braunii* poses serious limitations to its suitability as a robust biofuel production system.

There remains a need in the art to harness this unique oil biosynthetic capacity for use in a system that allows for more rapid and higher yield production.

SUMMARY

The presently-disclosed subject matter meets some or all of the above-identified needs, as will become evident to those of ordinary skill in the art after a study of information provided in this document.

This Summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

Botryococcene biosynthesis is thought to resemble that of squalene, a metabolite essential for sterol metabolism in all eukaryotes. Squalene arises from an initial condensation of two molecules of farnesyl diphosphate (FPP) to form pre-squalene diphosphate (PSPP), which then undergoes a reductive rearrangement to form squalene. In principle, botryococcene could arise from an alternative rearrangement of the pre-squalene intermediate. Because of these proposed similarities, the present inventors predicted that a botryococcene synthase would resemble squalene synthase and hence isolated squalene synthase-like genes from *B. braunii* race B. While *B. braunii* does harbor at least one typical squalene synthase, none of the other three squalene synthase-like (SSL) genes encode for botryococcene biosynthesis directly. SSL-1 catalyzes the biosynthesis of PSPP and SSL-2 the biosynthesis of bisfarnesyl ether, while SSL-3 does not appear able to directly utilize FPP as a substrate. However, when combinations of the synthase-like enzymes were mixed together, in vivo and in vitro, robust botryococcene (SSL-1+ SSL-3) or squalene biosynthesis (SSL1+SSL-2) was observed. These findings were unexpected because squalene synthase, an ancient and likely progenitor to the other *Botryococcus* triterpene synthases, catalyzes a two-step reaction within a single enzyme unit without intermediate release, yet in *B. braunii*, these activities appear to have separated and evolved inter-dependently for specialized triterpene oil production greater than 500 MYA. Co-expression of the SSL-1 and SSL-3 genes in different configurations, as independent genes, as gene fusions, or targeted to intracellular membranes, also demonstrate the potential for engineering even greater efficiencies of botryococcene biosynthesis.

The presently-disclosed subject matter includes an isolated polypeptide having triterpene synthase activity wherein the polypeptide includes a peptide domain selected from domains I, II, III, IV, and V, wherein domain I comprises an amino acid sequence that is at least 60% identical to the amino acid sequence of SEQ ID NO: 17, domain II comprises an amino acid sequence that is at least 60% identical to the amino acid sequence of SEQ ID NO: 18, domain III comprises an amino acid sequence that is at least 60% identical to the amino acid sequence of SEQ ID NO: 19, domain IV comprises an amino acid sequence that is at least 60% identical to the amino acid sequence of SEQ ID NO: 20, and domain V comprises an amino acid sequence that is at least 60% identical to the amino acid sequence of SEQ ID NO: 21. In some embodiments of the isolated polypeptide, domain I comprises the amino acid sequence of SEQ ID NO: 17, domain II comprises the amino acid sequence of SEQ ID NO: 18, domain III comprises the amino acid sequence of SEQ ID NO: 19, domain IV comprises the amino acid sequence of SEQ ID NO: 20, and domain V comprises the amino acid sequence of SEQ ID NO: 21. In some embodiments of the isolated polypeptide, the polypeptide comprises peptide domains I, II, III, IV, and V. In some embodiments, the isolated polypeptide includes the amino acid sequence of SEQ ID NO: 16. In some embodiments, the polypeptide has triterpene synthase activity. In some embodiments, the isolated polypeptide includes an amino acid sequence that is at least 60% identical to the amino acid sequence of SEQ ID NO: 16.

The presently-disclosed subject matter furthering includes an isolated nucleic acid, encoding the polypeptide including a peptide domain selected from domains I, II, III, IV, and V, wherein domain I comprises an amino acid sequence that is at least 60% identical to the amino acid sequence of SEQ ID NO: 17, domain II comprises an amino acid sequence that is at least 60% identical to the amino acid sequence of SEQ ID NO: 18, domain III comprises an amino acid sequence that is at least 60% identical to the amino acid sequence of SEQ ID NO: 19, domain IV comprises an amino acid sequence that is at least 60% identical to the amino acid sequence of SEQ ID NO: 20, and domain V comprises an amino acid sequence that is at least 60% identical to the amino acid sequence of SEQ ID NO: 21. In some embodiments the isolated nucleic acid further encodes a second polypeptide having triterpene synthase activity wherein the second polypeptide comprises a peptide domain selected from domains I, II, III, IV, and V, wherein domain I comprises an amino acid sequence that is at least 65% identical to the amino acid sequence of SEQ ID NO: 3, domain II comprises an amino acid sequence that is at least 65% identical to the amino acid sequence of SEQ ID NO: 4, domain III comprises an amino acid sequence that is at least 60% identical to the amino acid sequence of SEQ ID NO: 5, domain IV comprises an amino acid sequence that is at least 80% identical to the amino acid sequence of SEQ ID NO: 6, and domain V comprises an amino acid sequence that is at least 60% identical to the amino acid sequence of SEQ ID NO: 7. In some embodiments of the presently-disclosed subject matter a vector comprising the nucleic acid(s) is provided.

In some embodiments of the presently-disclosed subject matter a host cell transfected with the nucleic acid(s) is provided. In some embodiments, the host cell is further transfected with a nucleic acid molecule encoding a farnesyl diphosphate synthase, a triterpene methyltransferase, a squalene methyltransferase, or a botryococcene methyltransferase.

In some embodiments of the presently-disclosed subject matter an isolated polypeptide having triterpene synthase activity wherein the polypeptide comprises a peptide domain selected from domains I, II, III, IV, and V, wherein: domain I comprises an amino acid sequence that is at least 60% identical to the amino acid sequence of SEQ ID NO: 10, domain II comprises an amino acid sequence that is at least 60% identical to the amino acid sequence of SEQ ID NO: 11, domain III comprises an amino acid sequence that is at least 60% identical to the amino acid sequence of SEQ ID NO: 12, domain IV comprises an amino acid sequence that is at least 60% identical to the amino acid sequence of SEQ ID NO: 13, and domain V comprises an amino acid sequence that is at least 60% identical to the amino acid sequence of SEQ ID NO: 14. In some embodiments of the isolated polypeptide domain I comprises the amino acid sequence of SEQ ID NO: 10, domain II comprises the amino acid sequence of SEQ ID NO: 11, domain III comprises the amino acid sequence of SEQ ID NO: 12, domain IV comprises the amino acid sequence of SEQ ID NO: 13, and domain V comprises the amino acid sequence of SEQ ID NO: 14. In some embodiments the polypeptide comprises peptide domains I, II, III, IV, and V. In some embodiments the polypeptide has the amino acid sequence of SEQ ID NO: 9. In some embodiments, the polypeptide has triterpene synthase activity. In some embodiments, the polypeptide comprises an amino acid sequence that is at least 60% identical to the amino acid sequence of SEQ ID NO: 9.

The presently-disclosed subject matter further includes an isolated nucleic acid, encoding the polypeptide comprising a peptide domain selected from domains I, II, III, IV, and V, wherein: domain I comprises an amino acid sequence that is at least 60% identical to the amino acid sequence of SEQ ID NO: 10, domain II comprises an amino acid sequence that is at least 60% identical to the amino acid sequence of SEQ ID NO: 11, domain III comprises an amino acid sequence that is at least 60% identical to the amino acid sequence of SEQ ID NO: 12, domain IV comprises an amino acid sequence that is at least 60% identical to the amino acid sequence of SEQ ID NO: 13, and domain V comprises an amino acid sequence that is at least 60% identical to the amino acid sequence of SEQ ID NO: 14. In some embodiments, the nucleic acid further encodes a second polypeptide having triterpene synthase activity wherein the second polypeptide comprises a peptide domain selected from domains I, II, III, IV, and V, wherein: domain I comprises an amino acid sequence that is at least 65% identical to the amino acid sequence of SEQ ID NO: 3, domain II comprises an amino acid sequence that is at least 65% identical to the amino acid sequence of SEQ ID NO: 4, domain III comprises an amino acid sequence that is at least 60% identical to the amino acid sequence of SEQ ID NO: 5, domain IV comprises an amino acid sequence that is at least 80% identical to the amino acid sequence of SEQ ID NO: 6, and domain V comprises an amino acid sequence that is at least 60% identical to the amino acid sequence of SEQ ID NO: 7. In some embodiments of the presently-disclosed subject matter a vector comprising the nucleic acid(s) is provided.

In some embodiments of the presently-disclosed subject matter a host cell transfected with the nucleic acid(s) is provided. In some embodiments, the host cell is further transfected with a nucleic acid molecule encoding a farnesyl diphosphate synthase, a triterpene methyltransferase, a squalene methyltransferase, or a botryococcene methyltransferase.

The presently-disclosed subject matter further includes a method for producing triterpenes including: (a) providing a cell transfected with (i) a nucleic acid encoding a polypeptide having triterpene synthase activity wherein the polypeptide comprises a peptide domain selected from domains I, II, III, IV, and V, wherein: domain I comprises an amino acid sequence that is at least 60% identical to the amino acid sequence of SEQ ID NO: 17, domain II comprises an amino acid sequence that is at least 60% identical to the amino acid sequence of SEQ ID NO: 18, domain III comprises an amino acid sequence that is at least 60% identical to the amino acid sequence of SEQ ID NO: 19, domain IV comprises an amino acid sequence that is at least 60% identical to the amino acid sequence of SEQ ID NO: 20, and domain V comprises an amino acid sequence that is at least 60% identical to the amino acid sequence of SEQ ID NO: 21; or (ii) a nucleic acid encoding a polypeptide having triterpene synthase activity wherein the polypeptide comprises a peptide domain selected from domains I, II, III, IV, and V, wherein: domain I comprises an amino acid sequence that is at least 60% identical to the amino acid sequence of SEQ ID NO: 10, domain II comprises an amino acid sequence that is at least 60% identical to the amino acid sequence of SEQ ID NO: 11, domain III comprises an amino acid sequence that is at least 60% identical to the amino acid sequence of SEQ ID NO: 12, domain IV comprises an amino acid sequence that is at least 60% identical to the amino acid sequence of SEQ ID NO: 13, and domain V comprises an amino acid sequence that is at least 60% identical to the amino acid sequence of SEQ ID NO: 14; and (b) culturing the transfected cell under conditions suitable for production of triterpenes.

In some embodiments of the method the cell is further transfected with a second nucleic acid encoding a second polypeptide having triterpene synthase activity wherein the second polypeptide comprises a peptide domain selected from domains I, II, III, IV, and V, wherein: domain I comprises an amino acid sequence that is at least 65% identical to the amino acid sequence of SEQ ID NO: 3, domain II comprises an amino acid sequence that is at least 65% identical to the amino acid sequence of SEQ ID NO: 4, domain III comprises an amino acid sequence that is at least 50% identical to the amino acid sequence of SEQ ID NO: 5, domain IV comprises an amino acid sequence that is at least 80% identical to the amino acid sequence of SEQ ID NO: 6, and domain V comprises an amino acid sequence that is at least 40% identical to the amino acid sequence of SEQ ID NO: 7. In some embodiments, the method further includes isolating triterpene from the cultured cells.

The presently-disclosed subject matter further includes a kit for producing triterpenes, including (a) a first polypeptide having triterpene synthase activity wherein the polypeptide comprises a peptide domain selected from domains I, II, III, IV, and V, wherein: domain I comprises an amino acid sequence that is at least 60% identical to the amino acid sequence of SEQ ID NO: 17 or at least 60% identical to the amino acid sequence of SEQ ID NO: 10, domain II comprises an amino acid sequence that is at least 60% identical to the amino acid sequence of SEQ ID NO: 18 or at least 60% identical to the amino acid sequence of SEQ ID NO: 11, domain III comprises an amino acid sequence that is at least 60% identical to the amino acid sequence of SEQ ID NO: 19 or at least 60% identical to the amino acid sequence of SEQ ID NO: 12, domain IV comprises an amino acid sequence that is at least 60% identical to the amino acid sequence of SEQ ID NO: 20 or at least 60% identical to the amino acid sequence of SEQ ID NO: 13, and domain V comprises an amino acid sequence that is at least 60% identical to the amino acid sequence of SEQ ID NO: 21 or at least 60% identical to the amino acid sequence of SEQ ID NO: 14; and (b) a second polypeptide having triterpene synthase activity wherein the second polypeptide comprises a peptide domain selected from domains I, II, III, IV, and V, wherein: domain I comprises an amino acid sequence that is at least 65% identical to the amino acid sequence of SEQ ID NO: 3, domain II comprises an amino acid sequence that is at least 65% identical to the amino acid sequence of SEQ ID NO: 4, domain III comprises an amino acid sequence that is at least 50% identical to the amino acid sequence of SEQ ID NO: 5, domain IV comprises an amino acid sequence that is at least 80% identical to the amino acid sequence of SEQ ID NO: 6, and domain V comprises an amino acid sequence that is at least 40% identical to the amino acid sequence of SEQ ID NO: 7. In some embodiments of the kit, the first polypeptide is provided in a first container, and the second polypeptide is provided in a second container.

BRIEF DESCRIPTION OF THE DRAWINGS

FIG. 2 includes an amino acid alignment of BSS (SEQ ID NO: 22), SSL-1 (SEQ ID NO: 2), SSL-2 (SEQ ID NO: 9), and SSL-3 (SEQ ID NO: 16 from *B. braunii* race B. Five highly conserved domains amongst squalene synthase's identified by Robinson et al. (*Mol Cell Biol* 13:2706-2717) and the "FLAP" and putative NADPH binding site identified by Gu et al. (*J Biol Chem* 273:12515-12525) are boxed. Amino acids completely conserved in the squalene synthase of *B. braunii* (AF205791), *C. reinhardtii* (XM001703395), *A. thaliana* (NM119630), *N. tabacum* (U60057), *H. sapiens* (NM004462), *R. norvegicus* (NM019238), *S. cereviseae* (X59959), *S. pombe* (NM001021271), and *Y. lipolytica* (AF092497), plus those residues also conserved with these squalene synthases and dehydrosqualene synthase (CrtM) from *S. aureus* (AM920687), are labeled above the alignment. Residues of CrtM identified by Lin et al. (*Proc Natl Acad Sci USA* 107:21337-21342) as important for the first and second half reactions are labeled with a star. Possible membrane spanning regions of BSS and SSL2 as predicted by TMpred are underlined. In the subsequent studies, a 3' truncated form of SSL2 (tr2) missing the putative membrane spanning domain after D392 (indicated by arrow) was heterologously expressed in bacteria.

BRIEF DESCRIPTION OF THE SEQUENCE LISTING

Figure 1:
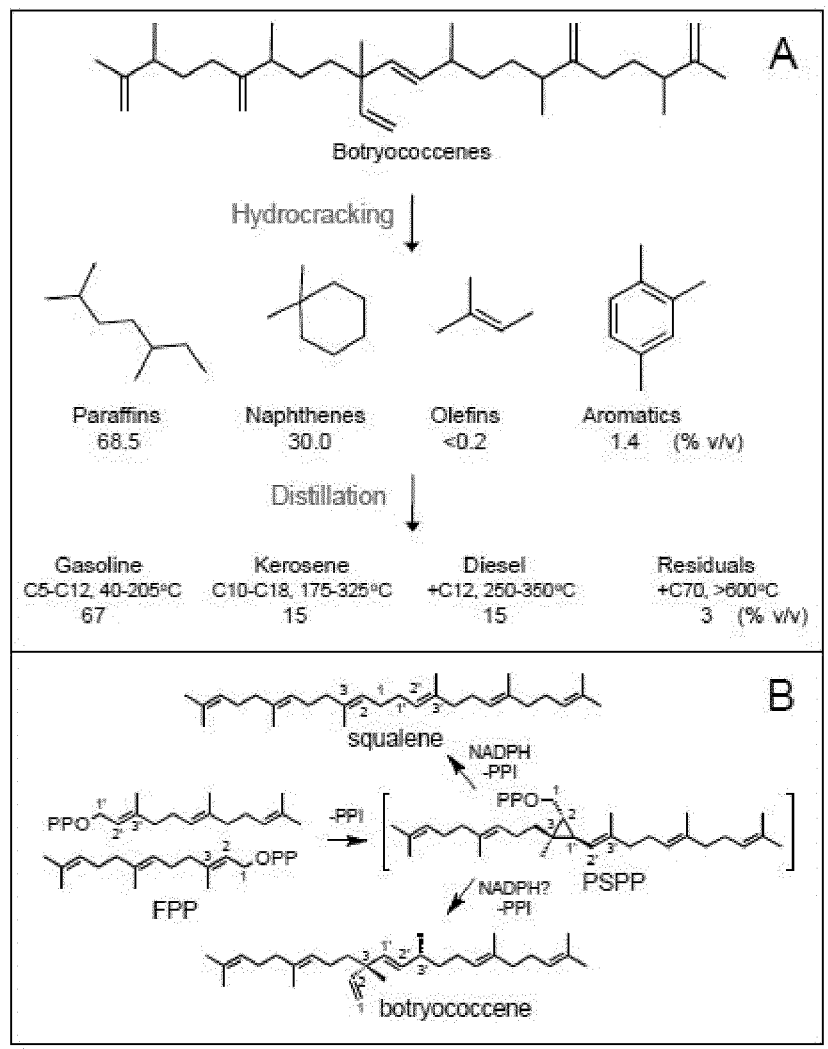
FIG. 1A includes an overview of the hydrocracking process of a typical $C_{34}$ botryococcene to yield fuel suitable for combustion engines; briefly, botryococcenes are treated with high pressure $H_2$ at high temperatures with a Pd catalyst to give a variety of organic molecules, which can be further distilled into various classes of fuel.
FIG. 1B includes biosynthetic pathways for botryococcene and squalene; both triterpenes are derived from an initial condensation of two FPP molecules to form presqualene diphosphate (PSPP), which is subsequently cleaved and reduced to form either botryococcene or squalene.

SEQ ID NO: 1 is a nucleic acid sequence for *Botryococcus braunii* race B squalene synthase-like 1 (SSL-1).

SEQ ID NO: 2 is an amino acid sequence for SSL-1.

SEQ ID NO: 3 is an amino acid sequence for Domain I of SSL-1.

SEQ ID NO: 4 is an amino acid sequence for Domain II of SSL-1.

SEQ ID NO: 5 is an amino acid sequence for Domain III of SSL-1.

SEQ ID NO: 6 is an amino acid sequence for Domain IV of SSL-1.

SEQ ID NO: 7 is an amino acid sequence for Domain V of SSL-1.

SEQ ID NO: 8 is a nucleic acid sequence for *Botryococcus braunii* race B squalene synthase-like 2 (SSL-2).

SEQ ID NO: 9 is an amino acid sequence for SSL-2.

SEQ ID NO: 10 is an amino acid sequence for Domain I of SSL-2.

SEQ ID NO: 11 is an amino acid sequence for Domain II of SSL-2.

SEQ ID NO: 12 is an amino acid sequence for Domain III of SSL-2.

SEQ ID NO: 13 is an amino acid sequence for Domain IV of SSL-2.

SEQ ID NO: 14 is an amino acid sequence for Domain V of SSL-2.

SEQ ID NO: 15 is a nucleic acid sequence for *Botryococcus braunii* race B squalene synthase-like 2 (SSL-3).

SEQ ID NO: 16 is an amino acid sequence for SSL-3.

SEQ ID NO: 17 is an amino acid sequence for Domain I of SSL-3.

SEQ ID NO: 18 is an amino acid sequence for Domain II of SSL-3.

SEQ ID NO: 19 is an amino acid sequence for Domain III of SSL-3.

SEQ ID NO: 20 is an amino acid sequence for Domain IV of SSL-3.

SEQ ID NO: 21 is an amino acid sequence for Domain V of SSL-3.

SEQ ID NO: 22 is an amino acid sequence for *Botryococcus* squalene synthase (BSS).

SEQ ID NO: 23 is an amino acid sequence for Domain I of BSS.

SEQ ID NO: 24 is an amino acid sequence for Domain II of BSS.

SEQ ID NO: 25 is an amino acid sequence for Domain III of BSS.

SEQ ID NO: 26 is an amino acid sequence for Domain IV of BSS.

SEQ ID NO: 27 is an amino acid sequence for Domain V of BSS.

SEQ ID NOS: 28-45 are nucleic acid sequences for nucleotide primers.

DESCRIPTION OF EXEMPLARY EMBODIMENTS

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

Some of the polynucleotide and polypeptide sequences disclosed herein are cross-referenced to GENBANK®/GENPEPT® accession numbers. The sequences cross-referenced in the GENBANK®/GENPEPT® database are expressly incorporated by reference as are equivalent and related sequences present in GENBANK®/GENPEPT® or other public databases. Also expressly incorporated herein by reference are all annotations present in the GENBANK®/GENPEPT® database associated with the sequences disclosed herein. Unless otherwise indicated or apparent, the references to the GENBANK®/GENPEPT® database are references to the most recent version of the database as of the filing date of this Application.

The following are relevant GENBANK® accession numbers: *Botryococcus braunii* race B squalene synthase-like 1 (SSL-1), -2 (SSL-2), and 3 (SSL-3), respectively, —HQ585058; HQ585059, and HQ585060.

While the terms used herein are believed to be well understood by one of ordinary skill in the art, definitions are set forth to facilitate explanation of the presently-disclosed subject matter.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments±20%, in some embodiments ±10%, in some embodiments ±5%, in some embodiments ±1%, in some embodiments ±0.5%, and in some embodiments ±0.1% from the specified amount, as such variations are appropriate to perform the disclosed method. By way of providing an example, about 60% is inclusive of: 60%±0.1%, which is inclusive of 59.9%-60.1%, and so forth.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

The presently-disclosed subject matter includes polypeptides, nucleic acid molecules, vectors, transfected cells, and methods for their use. The polypeptides of the presently-disclosed subject matter include, for example, polypeptides comprising the amino acid sequence set forth in SEQ ID NO: 2, 9, or 16, and fragments thereof. In some embodiments, the polypeptide fragments have triterpene synthase activity.

In some embodiments, the polypeptides comprise one or more peptide domains I, II, III, IV, V and IV, wherein domain I comprises LPQELQDPICIFYL (SEQ ID NO: 3), LPDELRHPICVFYL (SEQ ID NO: 10), or LPEVLQDPICVNYL (SEQ ID NO: 17); domain II comprises LRALDTVEDDMNLKSETK (SEQ ID NO: 4), LRALDTVEDDMNLPNEVK (SEQ ID NO: 11), or LRGLDTLQDDMAIPAEKR (SEQ ID NO: 18); domain III comprises YCHYVAGSCGIAVTKVIV (SEQ ID NO: 5), YCHYVAGLVGSAVAKIFV (SEQ ID NO: 12), or YAFTNNGPVAICLTKLWV (SEQ ID NO: 19); domain IV comprises GLLLQKANIITDYNED (SEQ ID NO: 6), GQFLQKTNVIRDYLED (SEQ ID NO: 13), or AMFLGKINVIRDIKED (SEQ ID NO: 20); and domain V comprises ALALLLVTAFGHLS (SEQ ID NO: 7), SCLIPEVMGLRTLT (SEQ ID NO: 14), or FCAVPELMSLATIS (SEQ ID NO: 21).

The polypeptides of the presently-disclosed subject matter can also contain one or more modified amino acids. The presence of modified amino acids can be advantageous in, for example, increasing triterpene synthase catalytic activity or increasing polypeptide stability. Amino acid(s) are modified, for example, co-translationally or post-translationally during recombinant production (e.g., N-linked glycosylation at N-X-S/T motifs during expression in mammalian cells) or modified by synthetic means. Accordingly, a "mutant", "variant" or "modified" protein, enzyme, polynucleotide, gene, or cell, means a protein, enzyme, polynucleotide, gene, or cell, that has been altered or derived, or is in some way different or changed, from a parent protein, enzyme, polynucleotide, gene, or cell. A mutant or modified protein or enzyme is usually, although not necessarily, expressed from a mutant polynucleotide or gene.

A "parent" protein, enzyme, polynucleotide, gene, or cell, is any protein, enzyme, polynucleotide, gene, or cell, from which any other protein, enzyme, polynucleotide, gene, or cell, is derived or made, using any methods, tools or techniques, and whether or not the parent is itself native or mutant. A parent polynucleotide or gene encodes for a parent protein or enzyme.

A "mutation" means any process or mechanism resulting in a mutant protein, enzyme, polynucleotide, gene, or cell. This includes any mutation in which a protein, enzyme, polynucleotide, or gene sequence is altered, and any detectable change in a cell arising from such a mutation. Typically, a mutation occurs in a polynucleotide or gene sequence, by point mutations, deletions, or insertions of single or multiple nucleotide residues. A mutation includes polynucleotide alterations arising within a protein-encoding region of a gene as well as alterations in regions outside of a protein-encoding sequence, such as, but not limited to, regulatory or promoter sequences. A mutation in a gene can be "silent", i.e., not reflected in an amino acid alteration upon expression, leading to a "sequence-conservative" variant of the gene. This generally arises because of degeneracy of the genetic code wherein more than one codon codes for the same amino acid.

Non-limiting examples of a modified amino acid include a glycosylated amino acid, a sulfated amino acid, a prenylated (e.g., farnesylated, geranylgeranylated) amino acid, an acetylated amino acid, an acylated amino acid, a pegylated amino acid, a biotinylated amino acid, a carboxylated amino acid, a phosphorylated amino acid, and the like. References adequate to guide one of skill in the modification of amino acids are replete throughout the literature. Example protocols are found in Walker (1998) Protein Protocols on CD-ROM (Humana Press, Towata, N.J.).

In some embodiments, the polypeptides of the presently disclosed subject matter include up to 35, 25, 10, 5, 4, 3, 2 or 1 non-conservative amino acid substitutions.

Recombinant methods for producing and isolating the triterpene synthase polypeptides and modified triterpene synthase polypeptides of the presently-disclosed subject matter are described herein. In addition to recombinant production, the polypeptides may be produced by direct peptide synthesis using solid-phase techniques (e.g., Stewart et al. (1969) Solid-Phase Peptide Synthesis (WH Freeman Co, San Francisco); and Merrifield (1963) J. Am. Chem. Soc. 85: 2149-2154; each of which is incorporated by reference). Peptide synthesis may be performed using manual techniques or by automation. Automated synthesis may be achieved, for example, using Applied Biosystems 431A Peptide Synthesizer (Perkin Elmer, Foster City, Calif.) in accordance with the instructions provided by the manufacturer.

A "protein" or "polypeptide", which terms are used interchangeably herein, comprises one or more chains of chemical building blocks called amino acids that are linked together by chemical bonds called peptide bonds. An "enzyme" means any substance, composed wholly or largely of protein, that catalyzes or promotes, more or less specifically, one or more chemical or biochemical reactions. A "native" or "wild-type" protein, enzyme, polynucleotide, gene, or cell, means a protein, enzyme, polynucleotide, gene, or cell that occurs in nature (whose form predominates in natural populations).

Accordingly, in various embodiments, isolated or recombinant polypeptides comprising the amino acid sequence set forth in SEQ ID NO: 2, SEQ ID NO: 9, and SEQ ID NO: 16 are provided. The polypeptides include up to 35, 25, 10, 5, 4, 3, 2 or 1 conservative amino acid substitutions.

"Conservative amino acid substitutions" or, simply, "conservative variations" of a particular sequence refers to the replacement of one amino acid, or series of amino acids, with essentially identical amino acid or series of amino acids. One of skill will recognize that individual substitutions, deletions or additions which alter, add or delete a single amino acid or a percentage of amino acids in an encoded sequence result in "conservative variations" where the alterations result in the deletion of an amino acid, addition of an amino acid, or substitution of an amino acid with a functionally similar amino acid.

Conservative substitution tables providing functionally similar amino acids are well known in the art. For example, one conservative substitution group includes Alanine (A), Serine (S), and Threonine (T). Another conservative substitution group includes Aspartic acid (D) and Glutamic acid (E). Another conservative substitution group includes Asparagine (N) and Glutamine (Q). Yet another conservative substitution group includes Arginine (R) and Lysine (K). Another conservative substitution group includes Isoleucine, (I) Leucine (L), Methionine (M), and Valine (V). Another conservative substitution group includes Phenylalanine (F), Tyrosine (Y), and Tryptophan (W).

Thus, "conservative amino acid substitutions" of a listed polypeptide sequence (e.g., SEQ ID NO:2, SEQ ID NO: 8, or SEQ ID NO: 15) include substitutions of a percentage, typically less than 10%, of the amino acids of the polypeptide sequence, with an amino acid of the same conservative substitution group. Accordingly, a conservatively substituted variation of a polypeptide of the presently-disclosed subject matter can contain, for example, substitutions of 35, 25, 10, 5, 4, 3, 2 or 1 amino acid with an amino acid of the same conservative substitution group.

It is understood that the addition of sequences that do not alter the encoded activity of a nucleic acid molecule, such as the addition of a non-functional or non-coding sequence, is a conservative variation of the basic nucleic acid molecule. The "activity" of an enzyme is a measure of its ability to catalyze a reaction, i.e., to "function", and may be expressed as the rate at which the product of the reaction is produced. For example, enzyme activity can be represented as the amount of product produced per unit of time or per unit of enzyme (e.g., concentration or weight), or in terms of affinity or dissociation constants. As used interchangeably herein a "triterpene synthase activity", "biological activity of triterpene synthase" or "functional activity of triterpene synthase", refers to an activity exerted by a triterpene synthase protein, polypeptide or nucleic acid molecule on a triterpene synthase polypeptide substrate, as determined in vivo, or in vitro, according to standard techniques.

One of skill in the art will appreciate that many conservative substitutions of the nucleic acid constructs which are disclosed herein yield a functionally identical construct. For example, owing to the degeneracy of the genetic code, "silent substitutions" (i.e., substitutions in a nucleic acid sequence which do not result in an alteration in an encoded polypeptide) are an implied feature of every nucleic acid sequence which encodes an amino acid.

Similarly, "conservative amino acid substitutions," in which one or a few amino acids in an amino acid sequence are substituted with different amino acids with highly similar properties, are also readily identified as being highly similar to a disclosed construct. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Such conservative variations of each disclosed sequence are a feature of the polypeptides provided herein.

It will be appreciated by those skilled in the art that due to the degeneracy of the genetic code, a multitude of nucleotide sequences encoding modified triterpene synthase polypeptides of the presently-disclosed subject matter may be produced, some of which bear substantial identity to the nucleic acid sequences explicitly disclosed herein. For instance, codons AGA, AGG, CGA, CGC, CGG, and CGU all encode the amino acid arginine. Thus, at every position in the nucleic acid molecules of the presently-disclosed subject matter where an arginine is specified by a codon, the codon can be altered to any of the corresponding codons described above without altering the encoded polypeptide. It is understood that U in an RNA sequence corresponds to T in a DNA sequence.

"Conservative variants" are proteins or enzymes in which a given amino acid residue has been changed without altering overall conformation and function of the protein or enzyme, including, but not limited to, replacement of an amino acid with one having similar properties, including polar or nonpolar character, size, shape and charge. Amino acids other than those indicated as conserved may differ in a protein or enzyme so that the percent protein or amino acid sequence similarity between any two proteins of similar function may vary and can be, for example, at least 30%, at least 50%, at least 70%, at least 80%, at least 90%, at least 95%, at least 98% or at least 99%, as determined according to an alignment scheme.

Non-conservative modifications of a particular polypeptide are those which substitute any amino acid not characterized as a conservative substitution. For example, any substitution which crosses the bounds of the six groups set forth above. These include substitutions of basic or acidic amino acids for neutral amino acids, (e.g., Asp, Glu, Asn, or Gln for Val, Ile, Leu or Met), aromatic amino acid for basic or acidic amino acids (e.g., Phe, Tyr or Trp for Asp, Asn, Glu or Gln) or any other substitution not replacing an amino acid with a like amino acid. Basic amino acids include lysine (K), arginine (R), histidine (H); acidic amino acids include aspartic acid (D), glutamic acid (E); uncharged polar amino acids include glycine (G), asparagine (N), glutamine (Q), serine (S), threonine (T), tyrosine (Y), cysteine (C); nonpolar amino acids include alanine (A), valine (V), leucine (L), isoleucine (I), proline (P), phenylalanine (F), methionine (M), tryptophan (W); beta-branched amino acids include threonine (T), valine (V), isoleucine (I); aromatic amino acids include tyrosine (Y), phenylalanine (F), tryptophan (W), histidine (H).

A polynucleotide, polypeptide, or other component is "isolated" when it is partially or completely separated from components with which it is normally associated (other proteins, nucleic acid molecules, cells, synthetic reagents, etc.). A nucleic acid molecule or polypeptide is "recombinant" when it is artificial or engineered, or derived from an artificial or engineered protein or nucleic acid molecule. For example, a polynucleotide that is inserted into a vector or any other heterologous location, e.g., in a genome of a recombinant organism, such that it is not associated with nucleotide sequences that normally flank the polynucleotide as it is found in nature is a recombinant polynucleotide. A protein expressed in vitro or in vivo from a recombinant polynucleotide is an example of a recombinant polypeptide. Likewise, a polynucleotide sequence that does not appear in nature, for example a variant of a naturally occurring gene, is recombinant. For example, an "isolated" nucleic acid molecule is one which is separated from other nucleic acid molecules which are present in the natural source of the nucleic acid molecule. For example, with regards to genomic DNA, the term "isolated" includes nucleic acid molecules which are separated from the chromosome with which the genomic DNA is naturally associated. Typically, an "isolated" nucleic acid molecule is free of sequences which naturally flank the nucleic acid molecule (i.e., sequences located at the 5' and 3' ends of the nucleic acid molecule) in the genomic DNA of the organism from which the nucleic acid molecule is derived. For example, in various embodiments, the isolated nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid molecule is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

In some embodiments, a polypeptide provided herein includes amino acid residue substitutions that correspond to positions in a particular sequence at least 80%, 85%, 90%, 95%, 98% or 99% of the time. In other words, the presently-disclosed subject matter encompasses polypeptides that contain the recited amino acid substitutions at 80%, 85%, 90%, 95%, 98% or 99% of the recited positions in a given sequence. The skilled artisan will recognize that not every substitution from a group of substitutions is necessary to obtain a modified polypeptide that is active on a triterpene substrate.

"Sequence identity" herein means the extent to which two nucleotide or amino acid sequences are invariant. "Sequence alignment" means the process of lining up two or more sequences to achieve maximal levels of identity (and, in the case of amino acid sequences, conservation) for the purpose of assessing the degree of similarity. Numerous methods for aligning sequences and assessing similarity/identity are known in the art such as, for example, the Cluster Method, wherein similarity is based on the MEGALIGN algorithm, as well as BLASTN, BLASTP, and FASTA (Lipman and Pearson, (1985), Pearson and Lipman, (1988)). When using all of these programs, the preferred settings are those that results in the highest sequence similarity. For example, the "identity" or "percent identity" with respect to a particular pair of aligned sequences can refer to the percent sequence identity that is obtained by ClustalW analysis (version W 1.8 available from European Bioinformatics Institute, Cambridge, UK), counting the number of identical matches in the alignment and dividing such number of identical matches by the greater of (i) the length of the aligned sequences, and (ii) 96, and using the following default ClustalW parameters to achieve slow/accurate pairwise alignments—Gap Open Penalty: 10; Gap Extension Penalty: 0.10; Protein weight matrix: Gonnet series; DNA weight matrix: IUB; Toggle Slow/Fast pairwise alignments=SLOW or FULL Alignment.

Two sequences are "optimally aligned" when they are aligned for similarity scoring using a defined substitution matrix (e.g., BLOSUM62), gap existence penalty and gap extension penalty so as to arrive at the highest score possible for that pair of sequences. Substitution matrices and their use in quantifying the similarity between two sequences are well-known in the art and described, e.g., in Dayhoff et al. (1978) "A model of evolutionary change in proteins" in "Atlas of Protein Sequence and Structure," Vol. 5, Suppl. 3 (ed. M. O. Dayhoff), pp. 345-352. Natl. Biomed. Res. Found., Washington, D.C. and Henikoff et al. (1992) Proc. Nat'l. Acad. Sci. USA 89: 10915-10919 (each of which is incorporated by reference). The BLOSUM62 matrix is often used as a default scoring substitution matrix in sequence alignment protocols such as Gapped BLAST 2.0. The gap existence penalty is imposed for the introduction of a single amino acid gap in one of the aligned sequences, and the gap extension penalty is imposed for each additional empty amino acid position inserted into an already opened gap. The alignment is defined by the amino acids positions of each sequence at which the alignment begins and ends, and optionally by the insertion of a gap or multiple gaps in one or both sequences so as to arrive at the highest possible score. While optimal alignment and scoring can be accomplished manually, the process is facilitated by the use of a computer-implemented alignment algorithm, e.g., gapped BLAST 2.0, described in Altschul et al. (1997) Nucl. Acids Res. 25: 3389-3402 (incorporated by reference herein), and made available to the public at the National Center for Biotechnology Information (NCBI) Website (www.ncbi.nlm.nih.gov). Optimal alignments, including multiple alignments, can be prepared using, e.g., PSI-BLAST, available through the NCB1 website and described by Altschul et al. (1997) Nucl. Acids Res. 25:3389-3402 (incorporated by reference herein).

With respect to a sequence that is optimally aligned with a reference sequence, a residue "corresponds to" the position in the reference sequence with which the residue is paired in the alignment. The "position" is denoted by a number that sequentially identifies each residue in the reference sequence, e.g., in the case of an amino acid, based on its position relative to the N-terminus. For example, in SEQ ID NO:2, position 1 is M, position 2 is T, position 3 is M, position 4 is H, etc. When a test sequence is optimally aligned with SEQ ID NO:2, a residue in the test sequence that aligns with the H at position 4 is said to "correspond to position 4" of SEQ ID NO:2. Owing to deletions, insertion, truncations, fusions, etc., that must be taken into account when determining an optimal alignment, in general the amino acid residue number in a test sequence as determined by simply counting from the N-terminal will not necessarily be the same as the number of its corresponding position in the reference sequence. For example, in a case where there is a deletion in an aligned test sequence, there will be no amino acid that corresponds to a position in the reference sequence at the site of deletion. Where there is an insertion in an aligned reference sequence, that insertion will not correspond to any amino acid position in the reference sequence. In the case of truncations or fusions there can be stretches of amino acids in either the reference or aligned sequence that do not correspond to any amino acid in the corresponding sequence.

Also contemplated are fragments of the full length triterpene synthase polypeptides and polynucleotides, e.g., fragments of polypeptides comprising the amino acid sequence set forth in SEQ ID NO: 2, SEQ ID NO: 9, and SEQ ID NO: 16 and fragments of nucleic acid molecules comprising the sequence set forth in SEQ ID NO: 1, SEQ ID NO: 8, and SEQ ID NO: 16. A "fragment" is a unique portion of a triterpene synthase polypeptide or the polynucleotide encoding triterpene synthase which is identical in sequence to, but shorter in length than, the parent sequence. A fragment may comprise up to the entire length of the defined sequence, minus one nucleotide/amino acid residue. For example, a fragment may comprise from 5 to 1000 contiguous nucleotides or amino acid residues of a given nucleic acid molecule or polypeptide. A fragment used as a probe, primer, antigen, catalytic molecule, or for other purposes, may be at least 5, 10, 15, 16, 20, 25, 30, 40, 50, 60, 75, 100, 150, 250 or at least 500 contiguous nucleotides or amino acid residues in length. Fragments may be preferentially selected from certain regions of a molecule. For example, a polypeptide fragment may comprise a certain length of contiguous amino acids selected from the first 250 or 500 amino acids (or first 25% or 50%) of a polypeptide as shown in a certain defined sequence. Clearly these lengths are exemplary, and any length that is supported by the specification, including the Sequence Listing, tables, and figures, may be encompassed by the present embodiments.

It is contemplated that in some fragment one or more domains of the polypeptide will remain in tact, with examples including, but not limited to the metal binding domain and the terpene synthase fold.

Also contemplated in the presently-disclosed subject matter are isolated polypeptides that are triterpene synthases, that comprise 5 peptide domains I, II, III, IV, and V. The peptide domains I, II, III, IV, and V of the triterpene synthase of the presently-disclosed subject matter may comprise respectively, e.g., SEQ ID NO: 3, SEQ ID NO: 4, SEQ ID NO: 5, SEQ ID NO: 6, and SEQ ID NO: 7; SEQ ID NO: 10, SEQ ID NO: 11, SEQ ID NO: 12, SEQ ID NO: 13, and SEQ ID NO: 14; SEQ ID NO: 17, SEQ ID NO: 18, SEQ ID NO: 19, SEQ ID NO: 20, and SEQ ID NO: 21 (See FIG. 3, the 5 domains of SSL-1, SSL-2, and SSL-3).

In an embodiment of the presently-disclosed subject matter, domain I comprises an amino acid sequence that is at least 60%, 70%, 80%, 90%, 95% or 98% identical to the full-length of SEQ ID NO: 3, SEQ ID NO: 10, or SEQ ID NO: 17; domain II comprises an amino acid sequence that is at least 60%, 70%, 80%, 90%, 95% or 98% identical the full-length of SEQ ID NO: 4, 11, or 18; domain III may comprise an amino acid sequence that is at least 60%, 70%, 80%, 90%, 95% or 98% identical to the full-length of SEQ ID NO: 5, 12, or 19; domain IV comprises an amino acid sequence that is at least 60%, 70%, 80%, 90%, 95% or 98% identical to the full-length of SEQ ID NO: 6, 13, or 20; and domain V comprises an amino acid sequence that is at least 60%, 70%, 80%, 90%, 95% or 98% identical the full-length of SEQ ID NO: 7, 14, or 21. The 5 peptide domains may be present in the synthase in any order, preferably the order of the 5 peptides in the polypeptide is, from its amino to carboxy terminal, I, II, III, IV, and V, and more preferably the I, II, III, IV and V domains comprise respectively SEQ ID NO: 3, SEQ ID NO: 4, SEQ ID NO: 5, SEQ ID NO: 6 and SEQ ID NO: 7; SEQ ID NO: 10, SEQ ID NO: 11, SEQ ID NO: 12, SEQ ID NO: 13, and SEQ ID NO: 14; or SEQ ID NO: 17, SEQ ID NO: 18, SEQ ID NO: 19, SEQ ID NO: 20, and SEQ ID NO: 21.

The presently-disclosed subject matter includes isolated nucleic acid molecules. Described herein are nucleic acid molecules that encode a polypeptide having triterpene synthase activity. The nucleic acid molecules of this invention include e.g., nucleic acid molecules that encode the amino acid sequence set forth in SEQ ID NO: 2, SEQ ID NO: 9, and SEQ ID NO: 16; nucleic acid molecules that encode fragments of SEQ ID NO: 2, SEQ ID NO: 9, and SEQ ID NO: 16; nucleic acid molecules that comprise SEQ ID NO:1, SEQ ID NO: 8, and SEQ ID NO: 15; and nucleic acid molecules that encode fragments of SEQ ID NO:1, SEQ ID NO: 8, and SEQ ID NO: 15. In one aspect, the invention provides a novel family of isolated or recombinant polynucleotides referred to herein as "triterpene synthase polynucleotides" or "triterpene synthase nucleic acid molecules." Triterpene synthase polynucleotide sequences are characterized by the ability to encode a triterpene synthase polypeptide. In general, the invention includes any nucleotide sequence that encodes any of the novel triterpene synthase polypeptides described herein. The terms "polynucleotide," "nucleotide sequence," and "nucleic acid molecule" are used to refer to a polymer of nucleotides (A, C, T, U, G, etc. or naturally occurring or artificial nucleotide analogues), e.g., DNA or RNA, or a representation thereof, e.g., a character string, etc., depending on the relevant context. A given polynucleotide or complementary polynucleotide can be determined from any specified nucleotide sequence.

In some embodiments, the triterpene synthase polynucleotides comprise recombinant or isolated forms of naturally occurring nucleic acid molecules isolated from an organism, e.g., an algae strain. Exemplary triterpene synthase polynucleotides include those that encode the polypeptide set forth in SEQ ID NO: 2, SEQ ID NO: 9, or SEQ ID NO: 16. In another aspect of the invention, triterpene synthase polynucleotides are produced by diversifying, e.g., mutating, a naturally occurring, isolated, or recombinant triterpene synthase polynucleotide, e.g., the nucleic acid sequence set forth in SEQ ID NO: 1, SEQ ID NO: 8, or SEQ ID NO: 15. It is possible to generate diversified triterpene synthase polynucleotides encoding triterpene synthase polypeptides with superior functional attributes, e.g., increased catalytic function, increased stability, or higher expression level, than a triterpene synthase encoded by the polynucleotide used as a substrate or parent in the diversification process.

The polynucleotides of the invention have a variety of uses in, for example recombinant production (i.e., expression) of the triterpene synthase polypeptides of the invention and as substrates for further diversity generation, e.g., recombination reactions or mutation reactions to produce new and/or improved triterpene synthase homologues, and the like.

It is important to note that certain specific, substantial and credible utilities of triterpene synthase polynucleotides do not require that the polynucleotide encode a polypeptide with substantial triterpene synthase activity or even variant triterpene synthase activity. For example, triterpene synthase polynucleotides that do not encode active enzymes can be valuable sources of parental polynucleotides for use in diversification procedures to arrive at triterpene synthase polynucleotide variants, or non-triterpene synthase polynucleotides, with desirable functional properties (e.g., high$_{cat}$ or k$_{cat}$/K$_m$, low K$_m$, high stability towards heat or other environmental factors, high transcription or translation rates, resistance to proteolytic cleavage, etc.).

Triterpene synthase polynucleotides, including nucleotide sequences that encode triterpene synthase polypeptides and variants thereof, fragments of triterpene synthase polypeptides, related fusion proteins, or functional equivalents thereof, are used in recombinant DNA molecules that direct the expression of the triterpene synthase polypeptides in appropriate host cells, such as plant cells. Due to the inherent degeneracy of the genetic code, other nucleic acid sequences which encode substantially the same or a functionally equivalent amino acid sequence can also be used to clone and express the triterpene synthase polynucleotides.

The term "host cell", as used herein, includes any cell type which is susceptible to transformation with a nucleic acid construct. The term "transformation" means the introduction of a foreign (i.e., extrinsic or extracellular) gene, DNA or RNA sequence to a host cell, so that the host cell will express the introduced gene or sequence to produce a desired substance, typically a protein or enzyme coded by the introduced gene or sequence. The introduced gene or sequence may include regulatory or control sequences, such as start, stop, promoter, signal, secretion, or other sequences used by the genetic machinery of the cell. A host cell that receives and expresses introduced DNA or RNA has been "transformed" and is a "transformant" or a "clone." The DNA or RNA introduced to a host cell can come from any source, including cells of the same genus or species as the host cell, or cells of a different genus or species.

As will be understood by those of skill in the art, it can be advantageous to modify a coding sequence to enhance its expression in a particular host. The genetic code is redundant with 64 possible codons, but most organisms preferentially use a subset of these codons. The codons that are utilized most often in a species are called optimal codons, and those not utilized very often are classified as rare or low-usage codons (see, e.g., Zhang et al. (1991) Gene 105:61-72; incorporated by reference herein). Codons can be substituted to reflect the preferred codon usage of the host, a process sometimes called "codon optimization" or "controlling for species codon bias."

Optimized coding sequences containing codons preferred by a particular prokaryotic or eukaryotic host (see also, Murray et al. (1989) Nucl. Acids Res. 17:477-508; incorporated by reference herein) can be prepared, for example, to increase the rate of translation or to produce recombinant RNA transcripts having desirable properties, such as a longer half-life, as compared with transcripts produced from a non-optimized sequence. Translation stop codons can also be modified to reflect host preference. For example, preferred stop codons for *S. cerevisiae* and mammals are UAA and UGA, respectively. The preferred stop codon for monocotyledonous plants is UGA, whereas insects and *E. coli* prefer to use UAA as the stop codon (Dalphin et al. (1996) Nucl. Acids Res. 24: 216-218; incorporated by reference herein). Methodology for optimizing a nucleotide sequence for expression in a plant is provided, for example, in U.S. Pat. No. 6,015,891, and the references cited therein (incorporated herein by reference).

"Silent variations" are one species of "conservative substitutions." One of skill will recognize that each codon in a nucleic acid sequence (except AUG, which is ordinarily the only codon for methionine) can be modified by standard techniques to encode a functionally identical polypeptide. Accordingly, each silent variation of a nucleic acid sequence that encodes a polypeptide is implicit in any described sequence. The invention provides each and every possible variation of nucleic acid sequence encoding a polypeptide of the invention that could be made by selecting combinations based on possible codon choices. These combinations are made in accordance with the standard triplet genetic code as applied to the nucleic acid sequence encoding a triterpene synthase homologue polypeptide of the invention. All such variations of every nucleic acid sequence herein are specifically provided and described by consideration of the sequence in combination with the genetic code. Any variant can be produced as noted herein.

In general, the invention includes any polypeptide encoded by a modified triterpene synthase polynucleotide derived by mutation, recursive sequence recombination, and/or diversification of the polynucleotide sequences described herein. In some aspects of the invention, a triterpene synthase polypeptide is modified by single or multiple amino acid substitutions, a deletion, an insertion, or a combination of one or more of these types of modifications. Substitutions can be conservative or non-conservative, can alter function or not, and can add new function. Insertions and deletions can be substantial, such as the case of a truncation of a substantial fragment of the sequence, or in the fusion of additional sequence, either internally or at N or C terminal.

Some embodiments of the presently-disclosed subject matter pertain to isolated nucleic acid molecules that encode modified triterpene synthase polypeptides or biologically active portions thereof. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

A nucleic acid molecule of the present invention, e.g., a nucleic acid molecule that encodes a polypeptide set forth in SEQ ID NO: 2, SEQ ID NO: 9, or SEQ ID NO: 16), or having the nucleotide sequence of set forth in SEQ ID NO: 1, SEQ ID NO: 8, or SEQ ID NO: 15, or a portion thereof, can be isolated using standard molecular biology techniques and the sequence information provided herein.

A nucleic acid molecule of the invention can be amplified using cDNA, mRNA or alternatively, genomic DNA, as a template and appropriate oligonucleotide primers according to standard PCR amplification techniques. The nucleic acid molecule so amplified can be cloned into an appropriate vector and characterized by DNA sequence analysis. Furthermore, oligonucleotides corresponding to nucleotide sequences can be prepared by standard synthetic techniques, e.g., using an automated DNA synthesizer. In some embodiments, an isolated nucleic acid molecule of the invention comprises a nucleic acid molecule which is a complement of a nucleotide sequence encoding a polypeptide set forth in SEQ ID NO: 2, SEQ ID NO: 9, or SEQ ID NO: 16, or complement of the nucleotide sequence set forth in SEQ ID NO: 1, SEQ ID NO: 8, or SEQ ID NO: 15. In still another embodiment, an isolated nucleic acid molecule of the invention comprises a nucleotide sequence which is at least about 50%, 52%, 55%, 60%, 62%, 65%, 70%, 75%, 78%, 80%, 85%, 88%, 90%, 95%, 97%, 98% or more identical to the nucleotide sequence encoding a polypeptide set forth in SEQ ID NO: 2, SEQ ID NO: 9, or SEQ ID NO: 16, or the nucleotide sequence set forth in SEQ ID NO: 1, SEQ ID NO: 8, or SEQ ID NO: 15, or a portion of any of these nucleotide sequences.

In addition to the nucleotide sequences encoding a polypeptide set forth in SEQ ID NO: 2, SEQ ID NO: 9, or SEQ ID NO: 16, or the nucleotide sequence set forth in SEQ ID NO: 1, SEQ ID NO: 8, or SEQ ID NO: 15, it will be appreciated by those skilled in the art that DNA sequence polymorphisms that lead to changes in the amino acid sequences of the proteins may exist within a population. Such genetic polymorphisms may exist among individuals within a population due to natural allelic variation. Such natural allelic variations include both functional and non-functional proteins and can typically result in 1-5% variance in the nucleotide sequence of a gene. Any and all such nucleotide variations and resulting amino acid polymorphisms in genes that are the result of natural allelic variation and that do not alter the functional activity of a protein are intended to be within the scope of the invention.

Accordingly, in another embodiment, an isolated nucleic acid molecule of the invention hybridizes under stringent conditions to a nucleic acid molecule comprising the nucleotide sequence encoding a polypeptide set forth in SEQ ID NO: 2, SEQ ID NO: 9, and SEQ ID NO: 1, or the nucleotide sequence set forth in SEQ ID NO: 1, SEQ ID NO: 8, and SEQ ID NO: 15. In other embodiments, the nucleic acid molecule is at least 30, 50, 100, 150, 200, 250, 300, 350, 400, 450, 500, 550, or 600 nucleotides in length. Nucleic acid molecules are "hybridizable" to each other when at least one strand of one polynucleotide can anneal to another polynucleotide under defined stringency conditions. Stringency of hybridization is determined, e.g., by (a) the temperature at which hybridization and/or washing is performed, and (b) the ionic strength and polarity (e.g., formamide) of the hybridization and washing solutions, as well as other parameters. Hybridization requires that the two polynucleotides contain substantially complementary sequences; depending on the stringency of hybridization, however, mismatches may be tolerated. Typically, hybridization of two sequences at high stringency (such as, for example, in an aqueous solution of 0.5×SSC at 65° C.) requires that the sequences exhibit some high degree of complementarity over their entire sequence. Conditions of intermediate stringency (such as, for example, an aqueous solution of 2×SSC at 65° C.) and low stringency (such as, for example, an aqueous solution of 2×SSC at 65° C.), require correspondingly less overall complementarity between the hybridizing sequences (1×SSC is 0.15 M NaCl, 0.015 M Na citrate).

Nucleic acid molecules that hybridize include those which anneal under suitable stringency conditions and which encode polypeptides or enzymes having the same function, such as the ability to catalyze the reductive condensation of 2 farnexyl diphosphate (FPP) substrate molecules yielding botryococcene, a 30-carbon branched-chain hydrocarbon, of the invention. Further, the term "hybridizes under stringent conditions" is intended to describe conditions for hybridization and washing under which nucleotide sequences at least 30%, 40%, 50%, or 60% homologous to each other typically remain hybridized to each other. Preferably, the conditions are such that sequences at least about 70%, more preferably at least about 80%, even more preferably at least about 85% or 90% homologous to each other typically remain hybridized to each other. In some cases, an isolated nucleic acid molecule of the invention that hybridizes under stringent conditions to a nucleic acid sequence encoding a polypeptide set forth in any of SEQ ID NO:2, SEQ ID NO: 9, or SEQ ID NO: 16, or the nucleotide sequence set forth in SEQ ID NO:1, SEQ ID NO: 8, or SEQ ID NO: 15, corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein). Preferably the nucleic acid molecule that hybridizes, hybridizes to at least 30%, 40%, 50%, 60%, 70%, 80%, 85% or 90% of the length of a nucleic acid molecule consisting of SEQ ID NO:1, SEQ ID NO: 8, or SEQ ID NO: 15 under stringent conditions. More preferably the nucleic acid molecule that hybridizes, hybridizes to at least about 80%, even more preferably at least about 85% or 90% of the length of a nucleic acid molecule consisting of SEQ ID NO: 1, SEQ ID NO: 8, or SEQ ID NO: 15. Preferably the nucleic acid molecule that hybridizes encodes a polypeptide having triterpene synthase activity.

The skilled artisan will appreciate that changes can be introduced by mutation into the nucleotide sequences of any nucleic acid sequence encoding a polypeptide set forth in SEQ ID NO:2, SEQ ID NO: 9, or SEQ ID NO: 16, or having the nucleotide sequence set forth in SEQ ID NO:1, SEQ ID NO: 8, or SEQ ID NO: 15, thereby leading to changes in the amino acid sequence of the encoded proteins. In some cases the alteration will lead to altered function of the polypeptide. In other cases the change will not alter the functional ability of the encoded polypeptide. In general, substitutions that do not alter the function of a polypeptide include nucleotide substitutions leading to amino acid substitutions at "non-essential" amino acid residues. Generally these substitutions can be made in, for example, the sequence encoding a polypeptide set forth in SEQ ID NO:2, SEQ ID NO: 9, or SEQ ID NO: 16, or having the nucleotide sequence set forth in SEQ ID NO:1, SEQ ID NO: 8, or SEQ ID NO: 15, without altering the ability of the enzyme to catalyze the reductive condensation of FPP substrate. A "non-essential" amino acid residue is a residue that can be altered from the parent sequence without altering the biological activity of the resulting polypeptide, e.g., catalyzing the reductive condensation of 2 FPP to yield botryococcene.

Also contemplated are those situations where it is desirable to alter the activity of a parent polypeptide such that the polypeptide has new or increased activity on a particular substrate. It is understood that these amino acid substitutions will generally not constitute "conservative" substitutions. Instead, these substitutions constitute non-conservative substitutions introduced in to a sequence in order to obtain a new or improved activity.

It is also understood that an isolated nucleic acid molecule encoding a polypeptide homologous to the polypeptide of SEQ ID NO:2, SEQ ID NO: 9, or SEQ ID NO: 16 can be created by introducing one or more nucleotide substitutions, additions or deletions into the nucleotide sequence encoding the particular polypeptide, such that one or more amino acid substitutions, additions or deletions are introduced into the encoded protein. Mutations can be introduced into the nucleic acid sequence by standard techniques, such as site-directed mutagenesis and PCR-mediated mutagenesis. In contrast to those positions where it may be desirable to make a non-conservative amino acid substitutions (see above), in some positions it is preferable to make conservative amino acid substitutions.

Mutational methods of generating diversity include, for example, site-directed mutagenesis (Ling et al. (1997) Anal Brioche. 254(2): 157-178; Dale et al. (1996) Methods Mol. Biol. 57:369-374; Smith (1985) Ann. Rev. Genet. 19:423-462; Botstein & Shortle (1985) Science 229:1193-1201; Carter (1986) Biochem. J. 237:1-7; and Kunkel (1987) "The efficiency of oligonucleotide directed mutagenesis" in Nucleic Acids & Molecular Biology (Eckstein, F. and Lilley, D. M. J. eds., Springer Verlag, Berlin)); mutagenesis using uracil containing templates (Kunkel (1985) Proc. Natl. Acad. Sci. USA 82:488-492; Kunkel et al. (1987) Methods in Enzymol. 154, 367-382; and Bass et al. (1988) Science 242:240-245); oligonucleotide-directed mutagenesis (Methods in Enzymol. 100: 468-500 (1983); Methods in Enzymol. 154: 329-350 (1987); Zoller & Smith (1982) Nucleic Acids Res. 10:6487-6500; Zoller & Smith (1983) Methods in Enzymol. 100:468-500; and Zoller & Smith (1987) Methods in Enzymol. 154:329-350); phosphorothioate-modified DNA mutagenesis (Taylor et al. (1985) Nucl. Acids Res. 13: 8749-8764; Taylor et al. (1985) Nucl. Acids Res. 13: 8765-8787; Nakamaye & Eckstein (1986) Nucl. Acids Res. 14: 9679-9698; Sayers et al. (1988) Nucl. Acids Res. 16:791-802; and Sayers et al. (1988) Nucl. Acids Res. 16: 803-814); mutagenesis using gapped duplex DNA (Kramer et al. (1984) Nucl. Acids Res. 12: 9441-9456; Kramer & Fritz (1987) Methods in Enzymol. 154:350-367; Kramer et al. (1988) Nucl. Acids Res. 16: 7207; and Fritz et al. (1988) Nucl. Acids Res. 16: 6987-6999) (each of which is incorporated by reference).

Additional suitable methods include point mismatch repair (Kramer et al. (1984) Cell 38:879-887), mutagenesis using repair-deficient host strains (Carter et al. (1985) Nucl. Acids Res. 13: 4431-4443; and Carter (1987) Methods in Enzymol. 154: 382-403), deletion mutagenesis (Eghtedarzadeh & Henikoff (1986) Nucl. Acids Res. 14: 5115), restriction-selection and restriction-purification (Wells et al. (1986) Phil. Trans. R. Soc. Lond. A 317: 415-423), mutagenesis by total gene synthesis (Nambiar et al. (1984) Science 223: 1299-1301; Sakamar and Khorana (1988) Nucl. Acids Res. 14: 6361-6372; Wells et al. (1985) Gene 34:315-323; and Grundstrom et al. (1985) Nucl. Acids Res. 13: 3305-3316); double-strand break repair (Mandecki (1986); Arnold (1993) Current Opinion in Biotechnology 4:450-455; and Proc. Natl. Acad. Sci. USA, 83:7177-7181) (each of which is incorporated by reference). Additional details on many of the above methods can be found in Methods in Enzymology (1987) Volume 154, which also describes useful controls for trouble-shooting problems with various mutagenesis methods.

Additional details regarding various diversity generating methods can be found in the following U.S. patents, PCT publications, and EPO publications: U.S. Pat. No. 5,605,793 to Stemmer (Feb. 25, 1997); U.S. Pat. No. 5,811,238 to Stemmer et al. (Sep. 22, 1998); U.S. Pat. No. 5,830,721 to Stemmer et al. (Nov. 3, 1998); U.S. Pat. No. 5,834,252 to Stemmer, et al. (Nov. 10, 1998); U.S. Pat. No. 5,837,458 to Minshull, et al. (Nov. 17, 1998); WO 95/22625, Stemmer and Crameri; WO 96/33207 by Stemmer and Lipschutz; WO 97/20078 by Stemmer and Crameri; WO 97/35966 by Minshull and Stemmer; WO 99/41402 by Punnonen et al.; WO 99/41383 by Punnonen et al.; WO 99/41369 by Punnonen et al.; WO 99/41368 by Punnonen et al.; EP 752008 by Stemmer and Crameri; EP 0932670 by Stemmer; WO 99/23107 by Stemmer et al.; WO 99/21979 by Apt et al.; WO 98/31837 by del Cardayre et al.; WO 98/27230 by Patten and Stemmer; WO 98/13487 by Stemmer et al.; WO 00/00632; WO 00/09679; WO 98/42832 by Arnold et al.; WO 99/29902 by Arnold et al.; WO 98/41653 by Vind; WO 98/41622 by Borchert et al.; WO 98/42727 by Pati and Zarling; WO 00/18906 by Patten et al.;

WO 00/04190 by del Cardayre et al.; WO 00/42561 by Crameri et al.; WO 00/42559 by Selifonov and Stemmer; WO 00/42560 by Selifonov et al.; WO 01/23401 by Welch et al.; and WO 01/64864 by Affholter (each of which is incorporated by reference). The QUICKCHANGE™ protocol marketed by Stratagene of San Diego, Calif. is one specific method known to those skilled in the art for introducing site-directed mutations. This method relies on the use of oligo or DNA primer pairs, harboring specific DNA sequence changes to be introduced, annealed to the target DNA or gene to be modified. Copies of modified DNA/gene are amplified by standard PCR methodology. Confirmation of alteration of the target DNA sequence is verifiable by automated DNA sequencing.

Also provided are recombinant constructs comprising one or more of the nucleic acid sequences as broadly described above. The constructs comprise a vector, such as, a plasmid, a cosmid, a phage, a virus, a bacterial artificial chromosome (BAC), a yeast artificial chromosome (YAC), or the like, into which a nucleic acid sequence of the invention has been inserted, in a forward or reverse orientation. In a preferred aspect of this embodiment, the construct further comprises regulatory sequences including, for example, a promoter operably linked to the sequence. Large numbers of suitable vectors and promoters are known to those of skill in the art, and are commercially available.

Accordingly, in other embodiments, vectors that include a nucleic acid molecule of the invention are provided. For example, in some embodiments, a vector can include a nucleic acid encoding a polypeptide set forth in SEQ ID NO:2, SEQ ID NO: 9, SEQ ID NO: 16, or a fragment thereof, or a nucleotide sequence set forth in SEQ ID NO:1, SEQ ID NO: 8, SEQ ID NO: 15, or a fragment thereof.

In some embodiments a vector can include a nucleic acid encoding a polypeptide set forth in SEQ ID NO: 9 or a fragment thereof, and further encoding a polypeptide set forth in SEQ ID NO: 2 or a fragment thereof. In some embodiments a vector can include a nucleic acid encoding a polypeptide set forth in SEQ ID NO: 9 or a fragment thereof, and further including a second nucleic acid encoding a polypeptide set forth in SEQ ID NO: 2 or a fragment thereof.

In some embodiments a vector can include a nucleic acid encoding a polypeptide set forth in SEQ ID NO: 16 or a fragment thereof, and further encoding a polypeptide set forth in SEQ ID NO: 2 or a fragment thereof. In some embodiments a vector can include a nucleic acid encoding a polypeptide set forth in SEQ ID NO: 16 or a fragment thereof, and further including a second nucleic acid encoding a polypeptide set forth in SEQ ID NO: 2 or a fragment thereof.

In some embodiments, a vector can include a nucleic acid molecule comprising a nucleic acid encoding a polypeptide comprising one or more of 5 peptide domains I, II, III, IV, and V. The peptide domains I, II, III, IV, and V of the triterpene synthase of the presently-disclosed subject matter may comprise respectively, e.g., SEQ ID NO: 3, SEQ ID NO: 4, SEQ ID NO: 5, SEQ ID NO: 6, and SEQ ID NO: 7; SEQ ID NO: 10, SEQ ID NO: 11, SEQ ID NO: 12, SEQ ID NO: 13, and SEQ ID NO: 14; SEQ ID NO: 17, SEQ ID NO: 18, SEQ ID NO: 19, SEQ ID NO: 20, and SEQ ID NO: 21 (See FIG. 3, the 5 domains of SSL-1, SSL-2, and SSL-3).

In some embodiments, a vector can include a nucleic acid molecule comprising a nucleic acid encoding a polypeptide comprising one or more of 5 peptide domains I, II, III, IV, and V, including: SEQ ID NO: 10, SEQ ID NO: 11, SEQ ID NO: 12, SEQ ID NO: 13, and SEQ ID NO: 14. In some embodiments, the nucleic acid can further encode a polypeptide comprising one or more of 5 peptide domains I, II, III, IV, and V, including: SEQ ID NO: 3, SEQ ID NO: 4, SEQ ID NO: 5, SEQ ID NO: 6, and SEQ ID NO: 7.

In some embodiments, a vector can include a nucleic acid molecule comprising a nucleic acid encoding a polypeptide comprising one or more polypeptides selected from: SEQ ID NO: 10, SEQ ID NO: 11, SEQ ID NO: 12, SEQ ID NO: 13, and SEQ ID NO: 14; and a second nucleic acid molecule comprising a nucleic acid encoding a polypeptide comprising one or more polypeptides selected from: SEQ ID NO: 3, SEQ ID NO: 4, SEQ ID NO: 5, SEQ ID NO: 6, and SEQ ID NO: 7.

In some embodiments, a vector can include a nucleic acid molecule comprising a nucleic acid encoding a polypeptide comprising one or more of 5 peptide domains I, II, III, IV, and V, including SEQ ID NO: 17, SEQ ID NO: 18, SEQ ID NO: 19, SEQ ID NO: 20, and SEQ ID NO: 21. In some embodiments, the nucleic acid can further encode a polypeptide comprising one or more of 5 peptide domains I, II, III, IV, and V, including: SEQ ID NO: 3, SEQ ID NO: 4, SEQ ID NO: 5, SEQ ID NO: 6, and SEQ ID NO: 7.

In some embodiments, a vector can include a nucleic acid molecule comprising a nucleic acid encoding a polypeptide comprising one or more polypeptides selected from SEQ ID NO: 17, SEQ ID NO: 18, SEQ ID NO: 19, SEQ ID NO: 20, and SEQ ID NO: 21; and a second nucleic acid molecule comprising a nucleic acid encoding a polypeptide comprising one or more polypeptides selected from: SEQ ID NO: 3, SEQ ID NO: 4, SEQ ID NO: 5, SEQ ID NO: 6, and SEQ ID NO: 7.

The presently-disclosed subject matter further includes host cells transfected with a nucleic acid molecule, or nucleic acid molecules, as described herein, or a vector that includes a nucleic acid molecule, or nucleic acid molecules, as described herein.

Host cells can include eucaryotic cells such as yeast cells, e.g., yeast cells having a ERG1 knockout, e.g., the yeast strain TN7 described in U.S. Patent Application Publication No. 2010/0009423 incorporated herein in its entirety, insect cells, animal cells, or plant cells (e.g., algal cells or terrestrial plant cells). Host cells also include procaryotic cells such as bacterial cells.

The terms "vector", "vector construct", and "expression vector" mean the vehicle by which a DNA or RNA sequence (e.g. a foreign gene) can be introduced into a host cell, so as to transform the host and promote expression (e.g. transcription and translation) of the introduced sequence. Vectors typically comprise the DNA of a transmissible agent, into which foreign DNA encoding a protein is inserted by restriction enzyme technology. A common type of vector is a "plasmid", which generally is a self-contained molecule of double-stranded DNA that can readily accept additional (foreign) DNA and which can readily introduced into a suitable host cell. A large number of vectors, including plasmid and viral vectors, have been described for replication and/or expression in a variety of eukaryotic and prokaryotic hosts. Non-limiting examples include pKK plasmids (Clonetech), pUC plasmids, pET plasmids (Novagen, Inc., Madison, Wis.), pRSET or pREP plasmids (Invitrogen, San Diego, Calif.), pMAL plasmids (New England Biolabs, Beverly, Mass.), and Ti plasmid vectors, and many appropriate host cells, using methods disclosed or cited herein or otherwise known to those skilled in the relevant art. Vectors can also be selected such that expression of the introduced sequence is targeted to a chloroplast in a plant cell. Recombinant cloning vectors will often include one or more replication systems for cloning or expression, one or more markers for selection in the host, e.g., antibiotic resistance, and one or more expression cassettes.

The terms "express" and "expression" mean allowing or causing the information in a gene or DNA sequence to become manifest, for example producing a protein by activating the cellular functions involved in transcription and translation of a corresponding gene or DNA sequence. A DNA sequence is expressed in or by a cell to form an "expression product" such as a protein. The expression product itself, e.g. the resulting protein, may also be said to be "expressed" by the cell. A polynucleotide or polypeptide is expressed recombinantly, for example, when it is expressed or produced in a foreign host cell under the control of a foreign or native promoter, or in a native host cell under the control of a foreign promoter.

Polynucleotides provided herein can be incorporated into any one of a variety of expression vectors suitable for expressing a polypeptide. Suitable vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, pseudorabies, adenovirus, adeno-associated viruses, retroviruses; Ti plasmids for the incorporation and expression of DNA in plant cells, and many others. Any vector that transduces genetic material into a cell, and, if replication is desired, which is replicable and viable in the relevant host can be used.

Vectors can be employed to transform an appropriate host to permit the host to express an inventive protein or polypeptide. Examples of appropriate expression hosts include: bacterial cells, such as *E. coli, B. subtilis, Streptomyces*, and *Salmonella typhimurium*; fungal cells, such as *Saccharomyces cerevisiae, Pichia pastoris*, and *Neurospora crassa*; insect cells such as *Drosophila* and *Spodoptera frugiperda*; mammalian cells such as CHO, COS, BHK, HEK 293 br Bowes melanoma; plant cells e.g., *Nicotiana tabacum*, a dicot plant species, or corn, a monocot plant species; algal cells e.g., *Chlamydomonas reinhardtii*; or explants of any plant tissues, e.g., leaf, stem or root segments, etc.

In bacterial systems, a number of expression vectors may be selected depending upon the use intended for the triterpene synthase polypeptide. For example, when large quantities of triterpene synthase polypeptide or fragments thereof are needed for commercial production or for induction of antibodies, vectors which direct high level expression of fusion proteins that are readily purified can be desirable. Such vectors include, but are not limited to, multifunctional *E. coli* cloning and expression vectors such as BLUESCRIPT™ (Stratagene), in which the triterpene synthase polypeptide coding sequence may be ligated into the vector in-frame with sequences for the amino-terminal Met and the subsequent 7 residues of 6-galactosidase so that a hybrid protein is produced; pIN vectors (Van Heeke & Schuster (1989) J. Biol. Chem. 264: 5503-5509); pET vectors (Novagen, Madison Wis.); and the like.

Similarly, in the yeast *Saccharomyces cerevisiae* a number of vectors containing constitutive or inducible promoters isolated from, e.g., an alpha factor, an alcohol dehydrogenase or a PGH gene may be used for production of the triterpene synthase polypeptides of the invention. For reviews, see Ausubel (supra) and Grant et al. (1987) Methods in Enzymology 153:516-544 (incorporated herein by reference).

Plant and algal systems may also be used for expression of triterpene synthase. Transcription of sequences encoding triterpene synthase may be driven by viral promoters, e.g., the 35S and 19S promoters of CaMV used alone or in combination with the omega leader sequence from TMV (Takamatsu, N. (1987) EMBO J. 6:307-311). Alternatively, plant promoters such as, e.g., the small subunit of RUBISCO or heat shock promoters may be used. (See, e.g., Coruzzi, G. et al. (1984) EMBO J. 3:1671-1680; Broglie, R. et al. (1984) Science 224:838-843; and Winter, J. et al. (1991) Results Probl. Cell Differ. 17:85-105.) For algal expression work, a strong constitutive promoter includes, e.g., a F-tubulin gene promoter (see Brunke, K J et al. (1984) Molec. Cell. Biol. 4: 1115-1124). These constructs can be introduced into plant cells, for example, by direct DNA transformation or pathogen-mediated transfection. (See, e.g., The McGraw Bill Yearbook of Science and Technology (1992) McGraw Hill, New York N.Y., pp. 191-196.)

Also provided are engineered host cells that are transduced (transformed or transfected) with a vector provided herein (e.g., a cloning vector or an expression vector), as well as the production of polypeptides of the invention by recombinant techniques. The vector may be, for example, a plasmid, a viral particle, a phage, etc. The engineered host cells can be cultured in conventional nutrient media modified as appropriate for activating promoters, selecting transformants, or amplifying the triterpene synthase gene. Culture conditions, such as temperature, pH and the like, are those previously used with the host cell selected for expression, and will be apparent to those skilled in the art and in the references cited herein, including, e.g., Sambrook, Ausubel and Berger, as well as e.g., Freshney (1994) Culture of Animal Cells: A Manual of Basic Technique, 3rd ed. (Wiley-Liss, New York) and the references cited therein.

The presently-disclosed subject matter further includes methods for making a cell for producing triterpenes. Such methods generally include: (a) transforming a host cell with an isolated nucleic acid molecule of the presently disclosed invention, as described herein, and (b) culturing the transformed cell to produce the triterpene (e.g., botryococcene). For example a transformed yeast cell of this invention may be cultured by large scale fermentation, providing the added advantage of producing large amounts of triterpenes, particularly botryococcene.

The presently-disclosed subject matter further includes, methods for selecting a cell that produces triterpenes. The methods can generally include: (a) providing a host cell containing a nucleic acid construct that includes a nucleotide sequence as described herein. The methods further include (b) culturing the cell in the presence of farnesyl diphosphate (FPP) and under conditions where the expressed polypeptide(s) is expressed at an effective level; and (c) detecting the production of triterpenes (e.g., botryococcene).

In other embodiments, methods for producing triterpenes (e.g., botryococcene) are provided. In one aspect, the methods for producing a botryococcene comprise culturing a host cell transfected with a nucleic acid molecule as described herein under conditions sufficient for production of a triterpene. Optionally, the triterpenes produced by the host cells are isolated. The host cell may be, for example, a cell in culture, e.g., the yeast strain TN7 transfected with a vector of this invention, or it may be a cell which is part of an organism such as a transfected cell in a terrestrial plant. In addition to transfection with the nucleic acid molecule of the presently-disclosed subject matter, such plant cells may also be cotransfected with nucleic acid molecules encoding for one or more other enzymes in the triterpene synthesis pathway, such as the genes for farnesyl diphosphate synthase or a triterpene synthase such as squalene synthase or triterpene methyltransferase. Plant cells for transfection include, for example algal cells such as *Botryococcus* spp. cells (e.g., *Botryococcus braunii*), *Chlamydomonas* spp. cells or terrestrial plant cells, such as a tobacco plant cell. Transfection of plant cells with exogenous genes may be directed to the cytosolic compartment, the chloroplast or both. In other embodiments, cells other than plant cells may be transformed with triterpene synthase-encoding nucleic acid molecules, and optionally with nucleic acid molecules encoding one or more other enzymes involved in triterpene synthesis. These cells include, for example, prokaryotic cells such as bacteria and eukaryotic cells, such as fungi or animal cells. In particular the cells may be a natural or recombinant yeast cells, e.g., yeast cells that accumulate FPP but do not metabolize squalene, e.g., yeast cells with a mutant or deleted or disrupted EGR1 gene such that it produces reduced or no squalene epoxidase, e.g., a yeast strain such as TN7. In any of the aforementioned embodiments, the cells may also be genetically altered to enhance the production of farnesyl diphosphate and thereby provide a larger precursor pool for triterpene synthesis, such as through gene knockout, so as to eliminate or reduce diversion of farnesyl diphosphate for use in synthesis of metabolites other than triterpenes, such as sesquiterpenes, sterols, or polyprenols, or to eliminate or reduce the action of phosphatase(s) on farnesyl diphosphate. The production of triterpenes may also be enhanced by diverting other metabolic intermediates such as, e.g., isopentenyl diphosphate or dimethylallyl diphosphate (DMAPP) to the production of FPP, therein providing enhanced carbon flux to a key intermediate for the biosynthesis of triterpenes.

Also an aspect of this invention is a method for producing triterpenes comprising transfecting a yeast strain with a nucleic acid molecule of the presently-disclosed subject matter and culturing the transfected cells under conditions suitable for the production of triterpenes. In some embodiments, the yeast strain has high intracellular concentrations of FPP and/or reduced levels of squalene epoxidase. In such embodiments, the high intracellular concentrations of FPP can be, e.g., at least 10 mg/L, at least 20 mg/L, at least 30 mg/L, at least 40 mg/L, at least 50 mg/L, at least 60 mg/L, at least 70 mg/L, or at least 80 mg/L. The reduced squalene epoxidase can be, e.g., less than the levels of squalene epoxidase found in the yeast strain CALI-7 (Takahashi et al., (2007) "Metabolic Engineering of Sesquiterpene Metabolism in Yeast" Biotech. Bioeng. 170-181). The reduced squalene expoxidase levels can also be undetectable levels, such as the levels in the yeast strain TN7.

In some embodiments, cells transfected with a nucleic acid molecule of the presently-disclosed subject matter are cultured under conditions suitable for the expression of a polypeptide, or polypeptides, of the presently-disclosed subject matter, and an extract rich in the polypeptide(s) is then prepared. This extract can be, for example, a cell paste or tissue homogenate, or it can be, for example, a purified or partially purified preparation of triterpene synthase. FPP, e.g., radiolabelled FPP, plus or minus reducing equivalents (NADPH) and algal lysates is then exposed to the extract rich in polypeptide(s) under conditions which allow for production of triterpenes (e.g., botryococcene). The reductive condensation may be via a batch process or a continuous process. Optionally the triterpenes (e.g., botryococcene) can then be isolated.

The presently-disclosed subject matter has utility as a drug development tool, and can be applied to better understand the mechanism of action of squalene synthase. As noted herein, the utility of the combination of the SSL-1 and SSL-2 or SSL-1 and SSL-2 polypeptides as described herein can provide a useful tool for identifying new drug targets for the control of squalene synthase, which is a target enzyme for control of cholesterol metabolism.

The presently-disclosed subject matter further includes kits for producing triterpenes. In some embodiments, the kit includes a polypeptide comprising the amino acid sequence set forth in SEQ ID NO: 9, SEQ ID NO: 16, or a fragment thereof. In some embodiments, the kit further includes a polypeptide comprising the amino acid sequence set forth in SEQ ID NO: 2 or a fragment thereof.

In some embodiments, the kit can include a polypeptide comprising one or more of 5 peptide domains I, II, III, IV, and V of SSL-3 or SSL-2. In some embodiments, the kit can further include a polypeptide comprising one or more of 5 peptide domains I, II, III, IV, and V of SSL-1.

In some embodiments, the kit can include a polypeptide comprising one or more of 5 peptide domains I, II, III, IV, and V, including: SEQ ID NO: 10, SEQ ID NO: 11, SEQ ID NO: 12, SEQ ID NO: 13, and SEQ ID NO: 14. In some embodiments, the kit can further include a second polypeptide comprising one or more of 5 peptide domains I, II, III, IV, and V, including: SEQ ID NO: 3, SEQ ID NO: 4, SEQ ID NO: 5, SEQ ID NO: 6, and SEQ ID NO: 7.

In some embodiments, the kit can include a polypeptide comprising one or more of 5 peptide domains I, II, III, IV, and V, including SEQ ID NO: 17, SEQ ID NO: 18, SEQ ID NO: 19, SEQ ID NO: 20, and SEQ ID NO: 21. In some embodiments, the kit can further include a second polypeptide comprising one or more of 5 peptide domains I, II, III, IV, and V, including: SEQ ID NO: 3, SEQ ID NO: 4, SEQ ID NO: 5, SEQ ID NO: 6, and SEQ ID NO: 7.

When more than one polypeptide is provided in the kit, the polypeptides can be provided together in a single container, or each in a separate container. The polypeptides can be provided, for example, as lyophylates. The kits can further include instructions for using the polypeptide(s) for producing triterpenes. The kits can further include useful substrates and/or other enzymes to facilitate the production of triterpenes.

As previously discussed, general texts which describe molecular biological techniques useful herein, including the use of vectors, promoters and many other relevant topics, include Berger and Kimmel, Guide to Molecular Cloning Techniques, Methods in Enzymology Volume 152, (Academic Press, Inc., San Diego, Calif.) ("Berger"); Sambrook et al., Molecular Cloning—A Laboratory Manual, 2d ed., Vol. 1-3, Cold Spring Harbor Laboratory, Cold Spring Harbor, N.Y., 1989 ("Sambrook") and Current Protocols in Molecular Biology, F. M. Ausubel et al., eds., Current Protocols, a joint venture between Greene Publishing Associates, Inc. and John Wiley & Sons, Inc., (supplemented through 1999) ("Ausubel") (each of which is incorporated by reference). Examples of protocols sufficient to direct persons of skill through in vitro amplification methods, including the polymerase chain reaction (PCR), the ligase chain reaction (LCR), Q.beta.-replicase amplification and other RNA polymerase mediated techniques (e.g., NASBA), e.g., for the production of the homologous nucleic acids of the invention are found in Berger, Sambrook, and Ausubel, as well as in Mullis et al. (1987) U.S. Pat. No. 4,683,202; Innis et al., eds. (1990) PCR Protocols: A Guide to Methods and Applications (Academic Press Inc. San Diego, Calif.) ("Innis"); Arnheim & Levinson (Oct. 1, 1990) C&EN 36-47; The Journal Of NIH Research (1991) 3: 81-94; Kwoh et al. (1989) Proc. Natl. Acad. Sci. USA 86: 1173; Guatelli et al. (1990) Proc. Nat'l. Acad. Sci. USA 87: 1874; Lomell et al. (1989) J. Clin. Chem. 35: 1826; Landegren et al. (1988) Science 241: 1077-1080; Van Brunt (1990) Biotechnology 8: 291-294; Wu and Wallace (1989) Gene 4:560; Barringer et al. (1990) Gene 89:117; and Sooknanan and Malek (1995) Biotechnology 13: 563-564 (each of which is incorporated by reference). Improved methods for cloning in vitro amplified nucleic acids are described in Wallace et al., U.S. Pat. No. 5,426,039. Improved methods for amplifying large nucleic acids by PCR are summarized in Cheng et al. (1994) Nature 369: 684-685 and the references cited therein (incorporated by reference herein), in which PCR amplicons of up to 40 kb are generated. One of skill will appreciate that essentially any RNA can be converted into a double stranded DNA suitable for restriction digestion, PCR expansion and sequencing using reverse transcriptase and a polymerase. See, e.g., Ausubel, Sambrook and Berger, all supra.

The presently-disclosed subject matter is further illustrated by the following specific but non-limiting examples. The following examples may include compilations of data that are representative of data gathered at various times during the course of development and experimentation related to the presently-disclosed subject matter.

EXAMPLES

Examplary studies are described herein. In identifying the triterpene biosynthetic genes in *B. braunii* the present inventors relied in part on the putative similarities in the biosynthetic mechanisms for squalene and botryococcene (19-21). Squalene biosynthesis has been extensively investigated because it is positioned at a putative branch point in the isoprenoid biosynthetic pathway directing carbon flux to sterol metabolism, and thus represents a potential control point for cholesterol biosynthesis in man (22). Evidence for a two-step reaction mechanism catalyzed by squalene synthase has been described (23) (FIG. 1B). The initial reaction step consists of a head-to-head condensation of 2 farnesyl diphosphate (FPP) molecules to form a stable cyclopropyl intermediate, pre-squalene diphosphate (PSPP) (24, 25). In the second reaction step, PSPP undergoes a reductive rearrangement in the presence of NADPH to yield squalene possessing a C1-C1' linkage between the two farnesyl substituents (26, 27) (FIG. 1B). Poulter (23) also suggested that botryococcene biosynthesis could occur via an analogous reaction mechanism with the initial reaction proceeding through PSPP, followed by a reductive rearrangement yielding a C3-C1' linkage between the two farnesyl precursors and possessing an ethyl as well as a methyl group at C3 in the final product.

Extensive investigations of squalene synthase including site-direct mutagenesis (28) and structural elucidation of 3-dimensional structure (29) have focused on 5 highly conserved domains (domains I-V) thought associated with catalysis (30). Many studies have also utilized these highly conserved domains as a means for isolating the corresponding genes from a diverse range of organisms. For instance, present inventors previously described the functional characterization of a squalene synthase gene from *B. braunii* race B (31). In that work, degenerate oligonucleotide primers complementary to several of the conserved domains were used to amplify a small region of a putative squalene synthase gene, and that gene fragment was then used to isolate a full-length cDNA from a cDNA library. Heterologous expression of that cDNA in bacteria and in vitro characterization of the encoded enzyme validated that the cDNA encoded for a squalene synthase enzyme, but lacked any detectable botryococcene synthase activity.

The studies described herein represent efforts to define the botryococcene biosynthetic pathway, to identify the genes coding for the unique enzymological transformations, and to reconstruct the initial steps of these unusual triterpene pathways in a heterologous host.

Functional Identification of Genes for Triterpene Biosynthesis.

Figure 3:
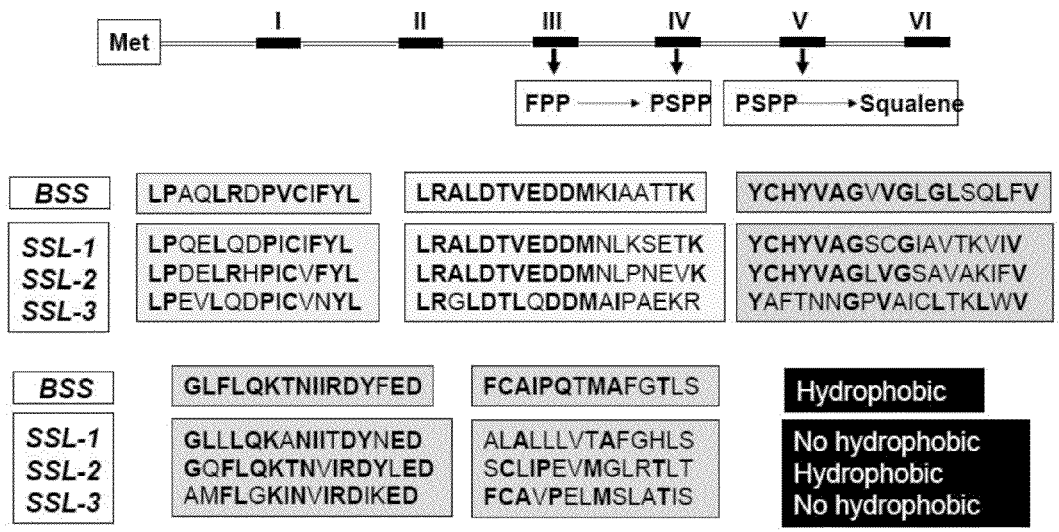
FIG. 3 includes an alignment comparison of selection regions/domains of sequence for *Botryococcus braunii* race B squalene synthase-like 1, 2, and 3, (SSL-1, SSL-2, and SSL-3), and *Botryococcus* squalene synthase (BSS). Sequences displayed across the five domains are: SSL1, SEQ ID NO: 3, 4, 5, 6, and 7; SSL-2, SEQ ID NO: 10, 11, 12, 13, and 14; SSL-3, SEQ ID NO: 17, 18, 19, 20, and 21; and BSS, SEQ ID NO: 23, 24, 25, 26, and 27.
Figure 4:
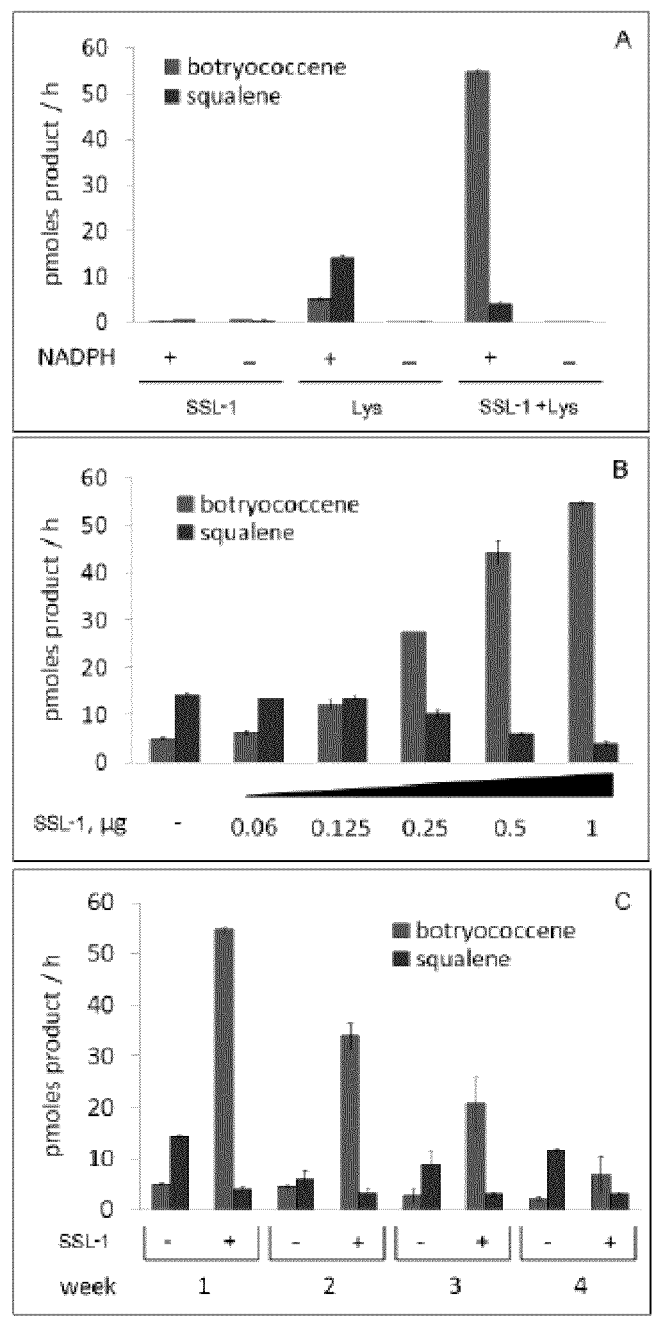
FIG. 4 depicts the dependence of the squalene synthase-like-1 enzyme on algal lysate for botryococcene biosynthesis. Purified SSL-1 enzyme (1 μg) (SSL-1), *B. braunii* 2000 g whole-cell lysate (10 μg protein) (Lys), and equal aliquots of both SSL-1 and lysate were incubated with radiolabeled FPP, with (+) or without (−) 2 mM NADPH and the incorporation into squalene and botryococcene determined by TLC separation of the reaction products followed by scintillation counting of the corresponding zones (panel A). Increasing amounts of purified SSL-1 were incubated with 10 μg of *B. braunii* 2000 g whole-cell lysate and the incorporation of radiolabeled FPP into squalene and botryococcene determined by TLC separation/scintillation counting (panel B). *B. braunii* 2000 g whole-cell lysates were prepared from cells collected at the indicated times (weeks) after subculturing, and aliquots containing 10 μg of protein were incubated without (−) or with (+) 1 μg of purified SSL-1 protein, and incorporation of radiolabeled FPP into squalene and botryococcene determined (panel C). The SSL-1 gene containing a 5' terminal sequence coding for a hexa-histidine tag was over-expressed in *E. coli* and the corresponding enzyme purified by cobalt affinity chromatography according to the manufacturer (Sigma). *B. braunii* lysate was prepared from cells collected at the indicated stages of culture development according to the procedure described by Okada, S. et al. (*Arch Biochem Biophys* 422: 110-118) and 10 μg of lysate protein was used per assay. Assays were incubated at 37° C. for 1 h, then the reaction products extracted with hexane. Aliquots of the hexane extracts was separated by silica TLC and the radioactivity migrating to zones corresponding to authentic standards of botryococcene and squalene determined by scintillation counting. Data represents mean±s.e.m.
Figure 5:
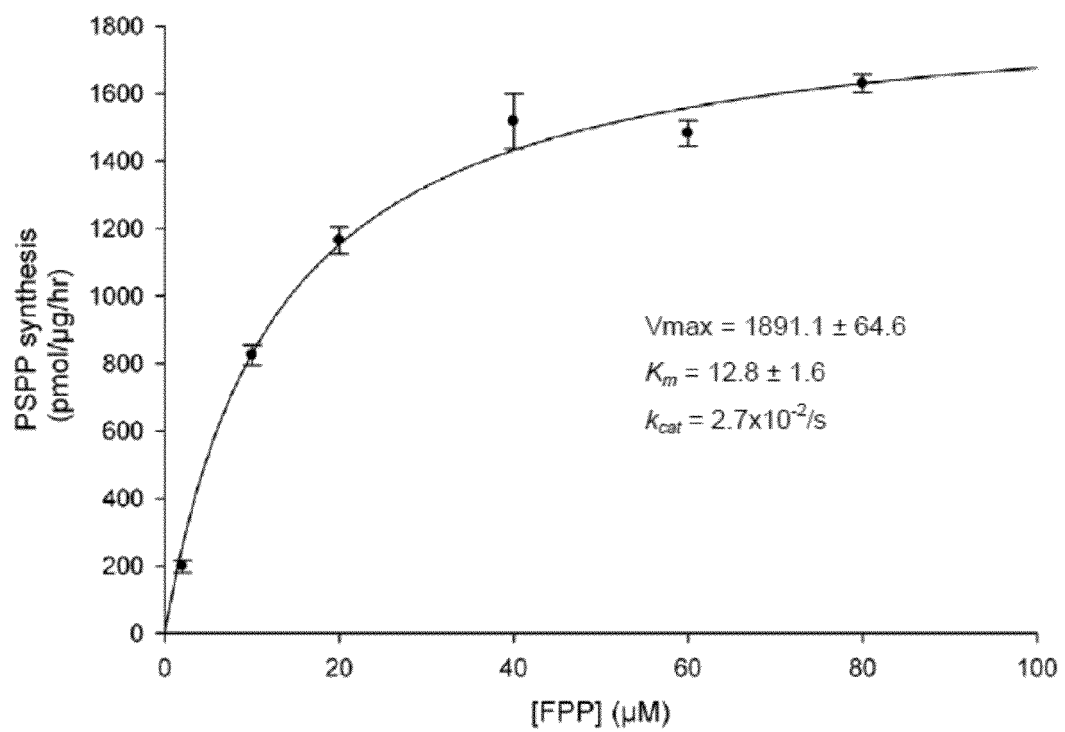
FIG. 5 depicts Michaelis-Menten enzyme kinetics of the SSL-1 reaction. Enzyme assays (50 µl) were set up as described in the methods section with purified SSL-1 (0.2-1.0 µg), 0.1% triton X-100, ±2 mM NADPH, and the indicated concentration of $^3$H-FPP. Assays were incubated for 15 min at 37° C. and stopped by addition of 50 µl 0.5 M EDTA. The reactions were then extracted 3× with 200 µl water saturated 1-butanol and pooled in a 4 ml glass screw cap vial. The butanol was evaporated with a stream of nitrogen gas and the white residue was resuspended in 2 ml of acid phosphatase solution (20% 1-propanol (v/v), 100 mM sodium acetate pH 4.7, 0.1% Triton X-100, 10 units sweet potato acid phosphatase) and incubated overnight (12-16 h) in a 28° C. shaker. Dephosphorylated products were extracted 3× with 1 ml n-hexane, pooled, dried with a stream of nitrogen gas, and resuspended in 200 µl of n-hexane. Aliquots of the hexane extract were spotted onto reverse-phase TLC plates along with standards of FOH and PSOH and developed with methanol:acetone (8:2). The standards were visualized with iodine vapors and the zones corresponding to FOH (rf=0.65) and PSOH (rf=0.45) were scraped and analyzed by scintillation spectroscopy. Addition of NADPH had no significant effect on enzyme activity (less than 4% difference) and greater than 95% of the input radioactivity was recovered as FOH and PSOH, indicating that PSPP is the only dominant reaction product formed from FPP by the SSL-1 enzyme. The data was analyzed using the SigmaPlot Enzyme Kinetics 1.3 software. Data represents mean±S.E.M of duplicate assays with and triplicate assays without NADPH.
Figure 6:
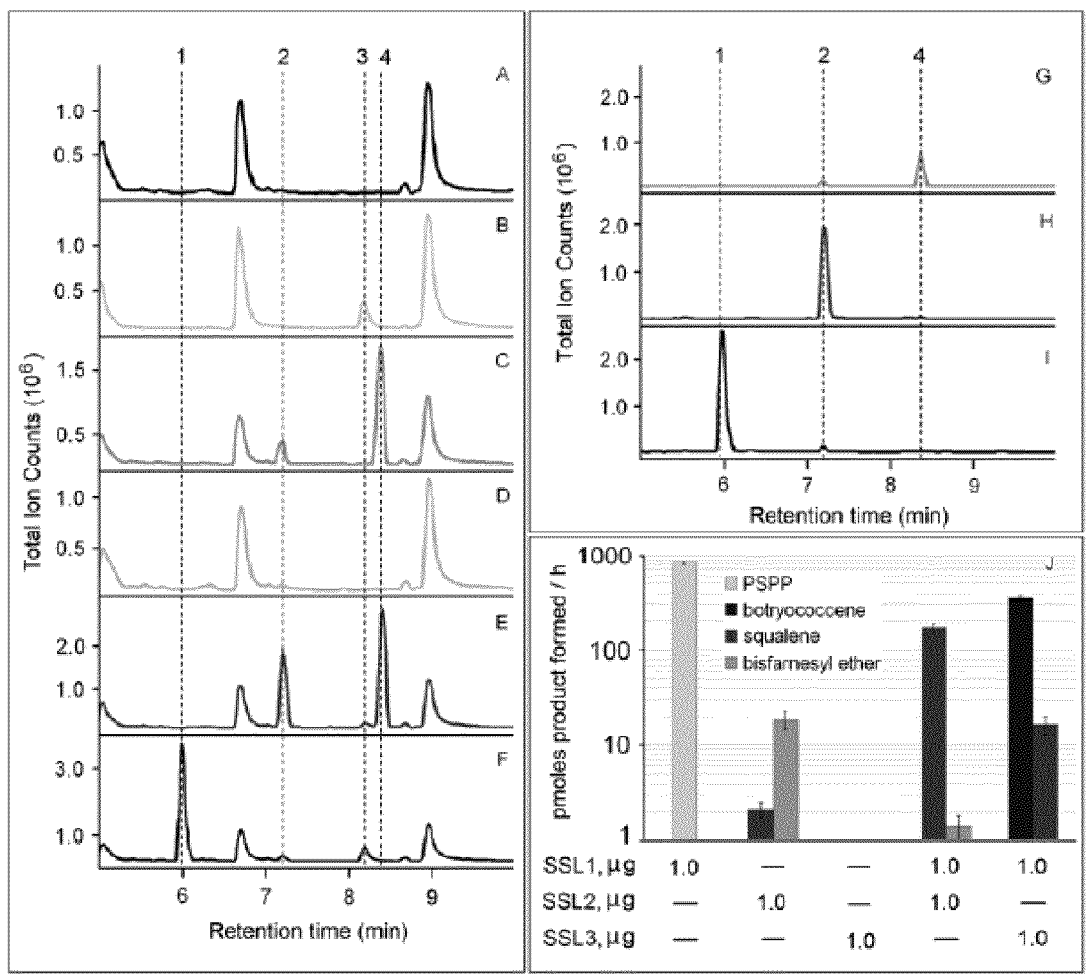
FIG. 6 depicts the functional characterization of the squalene synthase-like genes of *Botryococcus braunii* race B. The squalene synthase-like genes, SSL-1, SSL-2 and SSL-3, were expressed in yeast separately (SSL-1 (B), SSL-2(C) or SSL-3(D)) or in combinations (SSL-1+SSL-2(E), SSL-1+SSL-3(F)) and the hexane extractable metabolites profiled by GC-MS. The chemical profile of yeast not engineered with any gene constructs serves as the background control (A). The SSL genes were also expressed in bacteria, the affinity-tagged proteins purified and assayed separately (SSL-2 (G)) or in combinations (SSL-1+SSL-2 (H); SSL-1+SSL-3 (I)) for the reaction products generated upon incubation with FPP and profiled by GC-MS (G-I), or for quantitative determination of radio labeled FPP incorporated into specific reaction products separated by TLC (J). Data (J) represents mean±S.E.M. obtained from three independent experiments (n=3). The chromatograms (A-I) are also annotated for the elution behavior of botryococcene (1), squalene (2), presqualene alcohol (3) and bisfarnesyl ether (4).

Because the present inventors surmised that a botryococcene synthase enzyme might possess amino acid domains in common with squalene synthase, the *B. braunii* squalene synthase cDNA was used to re-screen the *B. braunii* cDNA library under low stringency hybridization conditions and a unique squalene synthase-like gene (SSL-1) was isolated and characterized. The SSL-1 gene predicted a squalene synthase-like protein exhibiting some resemblance to other squalene synthase enzymes within domains I-V, but missing a carboxy-terminal, membrane spanning domain (FIG. 2; FIG. 3). Surprisingly, purified bacterial expressed SSL-1 protein did not exhibit either squalene nor botryococcene biosynthesis when assayed in vitro even in the presence of a variety of reducing co-factors like NADPH (FIGS. 4A and 5), ferredoxin or cytochrome B5 systems. However, when SSL-1 was expressed in a yeast engineered for high-level production of FPP and having its endogenous squalene synthase and squalene epoxidase genes inactivated, pre-squalene alcohol (PSOH), the dephosphorylated form of PSPP, accumulated to significant levels (FIG. 6B). Subsequent incubations of SSL-1 with radiolabeled FPP confirmed robust in vitro production of PSPP as the sole reaction product with a $K_m$ for FPP of 12.8 µM and catalytic turnover rate ($k_{cat}$) equal to $2.7 \times 10^{-2}$/sec with no stimulation of activity by NADPH addition (FIGS. 6J and 5). This suggested that SSL-1 was catalytically competent for the first half reaction of squalene synthase, but perhaps required additional conditions or algal factors for complete catalytic activity. Mixing the purified SSL-1 enzyme with algal cell-free lysate did indeed enhance NAD(P)H-dependent botryococcene biosynthesis up to 10-fold, which was also proportional to the amount of the purified SSL-1 protein or the algal lysate added (FIG. 4A-C). The mechanism for botryococcene biosynthesis thus appeared to be similar to squalene synthase in its first half reaction, catalysis of PSPP formation, but differed in requiring another algal co-factor that either shuttled reducing equivalents to the reaction mechanism of SSL-1 or participated directly in the conversion of PSPP to botryococcene.

Figure 7:
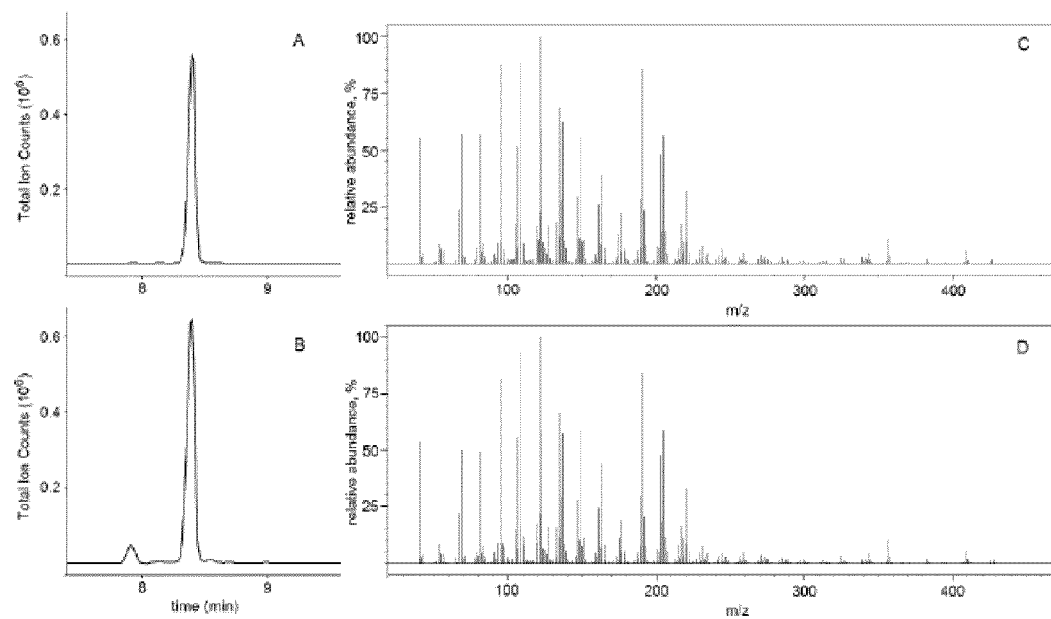
FIG. 7 includes GC chromatographs of unknown terpene purified from yeast overexpressing the SSL-2 gene (A) in comparison to chemically synthesized bisfarnesyl ether (B). The MS for the dominant peak compounds with retention time of 8.38 min in panels A and B are shown in panels C and D, respectively. Chemically synthesized bisfarnesyl ether produced identical NMR spectrums to the unknown terpene purified from yeast over-expressing the SSL-2 gene:
$^1$H NMR (400 MHz, CDCl$_3$) δ1.58 (br s, 6), 1.64-1.66 (m, 18), 1.92-2.14 (m, 16), 3.96 (d, J=6.8 Hz, 4), 5.04-5.12 (m, 4), 5.32-5.38 (m, 2);
$^{13}$C NMR (100 MHz, CDCl$_3$) δ 16.2 (CH$_2$C(CH$_3$)=CHCH$_2$), 16.7 (CH$_2$C(CH$_3$)=CHCH$_2$O), 17.9 (Z—CH$_3$ of (CH$_3$)$_2$C=CHCH$_2$), 25.9 (E-CH$_3$ of (CH$_3$)$_2$C=CHCH$_2$), 26.5 ((CH$_3$)$_2$C=CHCH$_2$), 26.9 (CH$_2$C(CH$_3$)=CHCH$_2$), 39.8 (CH$_2$C(CH$_3$)=CHCH$_2$), 39.9 (CH$_2$C(CH$_3$)=CHCH$_2$O), 66.6 (CH$_2$C(CH$_3$)=CHCH$_2$O), 121.3 (CH$_2$C(CH$_3$)=CHCH$_2$O), 124.1 ((CH$_3$)$_2$C=CHCH$_2$), 124.5 (CH$_2$C(CH$_3$)=CHCH$_2$), 131.5 ((CH$_3$)$_2$C=CHCH$_2$), 135.4 (CH$_2$C(CH$_3$)=CHCH$_2$), and 140.2 (CH$_2$C(CH$_3$)=CHCH$_2$O).

Because no natural occurring squalene synthase catalyzing only the first or second half reactions has been reported, the present inventors reasoned that other squalene synthase-like cDNAs for botryococcene biosynthesis might exist and therefore undertook a more exhaustive assessment of the SSL genes expressed in the *Botryococcus braunii* race B cells. The transcriptomic data from two independent sequencing efforts were thus assembled together and screened computationally for additional squalene synthase-like genes. Two additional SSL genes were uncovered and labeled SSL-2 and SSL-3 (FIG. 2). Although both of the predicted proteins showed amino acid sequence similarity to other squalene synthases in excess of 62%, neither bacterial-expressed, purified enzymes exhibited any botryococcene biosynthesis and only SSL-2 showed a low capacity for squalene biosynthesis when incubated with FPP as substrate (FIG. 6G). When expressed in yeast, SSL-3 also did not cause the accumulation of any distinct products (FIG. 6D), but SSL-2 resulted in the accumulation of a small amount of squalene (~10% of the total) and a terpene compound of unknown structure (FIG. 6C). The dominant terpene accumulating in the SSL-2 expressing yeast was subsequently identified by NMR as bisfarnesyl ether and confirmed by comparative analysis of corresponding ether prepared by chemical synthesis (FIG. 7). Subsequent analysis of the reaction products generated by in vitro incubation of SSL-2 with FPP also verified this enzyme as the source of this unique terpene ether (FIG. 6G & J).

Figure 8:
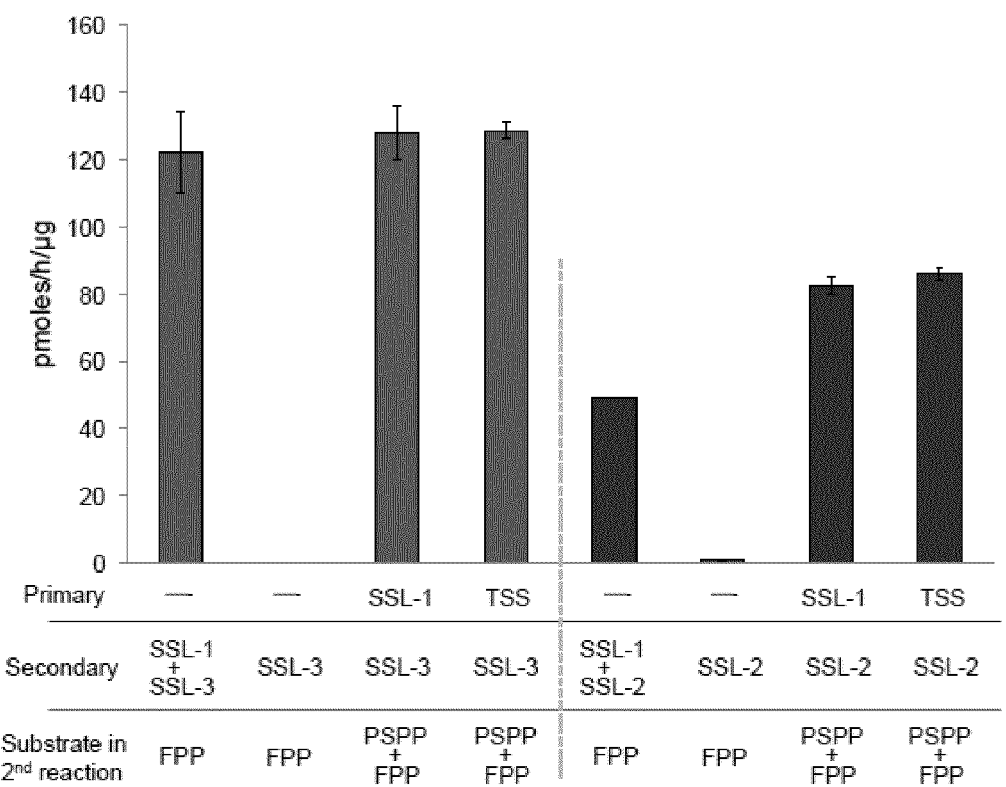
FIG. 8 shows that SSL-3 and SSL-2 utilize PSPP, but not FPP, for efficient biosynthesis of botryococcene or squalene, respectively. Two primary enzyme assays (500 µl) were set up with 20 µg of purified SSL-1 or *Nicotiana benthamiana* squalene synthase (TSS) plus 40 µM $^3$H-FPP. The assays were incubated at 37° C. for 1 h, then extracted 3× with 500 µl water saturated 1-butanol, pooled, and evaporated under a stream of nitrogen gas. The white residue was resuspended in 50 µl of 25 mM NH$_4$HCO$_3$ in 70% ethanol (v/v). An aliquot of the resuspension was analyzed by the acid phosphatase assay (described in supplemental FIG. 4) and shown to consist of 45% and 40% PSPP for the SSL-1 and TSS primary incubations, respectively. The remaining reaction product (55% and 60%, respectively) in both assays was FPP. It was calculated that 1 µl of each resuspension contained ~150 pmoles of 3H-PSPP. Secondary enzyme assays (50 µl) were set up with 1 µl of the reaction products isolated from the primary incubations (~3 µM PSPP and ~4 µM FPP), 2 mM NADPH, and either 1 µg of SSL-3 or SSL-2 enzyme. For comparison, enzyme assays were also set up containing 3 µM $^3$H-FPP, 2 mM NADPH and either 1 µg each of SSL-1 plus SSL-3, or SSL-1 plus SSL-2. Additional control assays contained 5 µM $^3$H-FPP, 2 mM NADPH, and either 1 µg of SSL-3 or SSL-2. The reactions were incubated at 37° C. for 15 min, stopped by addition of 50 µl 0.5 M EDTA, and extracted with 100 µl n-hexane. Aliquots of the hexane extracts, along with standards of squalene and botryococcene, were separated by silica TLC using n-hexane as the developing solvent. Standards were visualized with iodine vapors and the corresponding zones were analyzed by scintillation spectroscopy. Botryococcene biosynthesis is shown in blue and squalene biosynthesis is shown in red. Data represents mean±S.E.M.

The observations of unique terpene products from squalene synthase-like enzymes in *Botryococcus*, namely PSPP by SSL-1 and bisfarnesyl ether by SSL-2, suggested that triterpene metabolism in this algae may operate differently from that in other organisms. Hence, the present inventors considered the possibility that multiple SSL proteins might be required to give botryococcene biosynthesis. To evaluate this possibility, the different SSL genes were co-expressed in yeast, or the heterologous expressed and purified proteins were incubated in various combinations. When SSL-1 was co-expressed with SSL-2, the amount of squalene accumulating increased about 30-fold (FIG. 6E) along with a significant accumulation of bisfarnesyl ether still occurring. When purified SSL-1 and SSL-2 enzymes were incubated in a 1:1 stoichiometric ratio, squalene accumulation predominated (FIG. 6H), suggesting that something different mechanistically might be occurring when the SSL-1 and 2 genes were co-expressed in yeast (see below). More surprising, however, when SSL-1 and SSL-3 were co-expressed, botryococcene accumulation became readily apparent and accumulated to upwards of 20 mg/L along with 0.7 mg/L of squalene (FIG. 6F). In vitro incubations of the purified SSL-1 and SSL-3 proteins confirmed botryococcene as the predominant reaction product with squalene representing only 3-4% of the total reaction products (FIG. 6I & J). Additional in vitro studies have also confirmed that both SSL-2 and SSL-3 are able to efficiently catalyze the biosynthesis of squalene and botryococcene, respectively, from PSPP but not FPP, and these activities of SSL-2 and SSL-3 are sufficient to account for all the squalene and botryococcene biosynthesized in combined assays with SSL-1 (FIG. 8).

Mechanistic Considerations for Bisfarnesyl Ether Biosynthesis.

Figure 9:
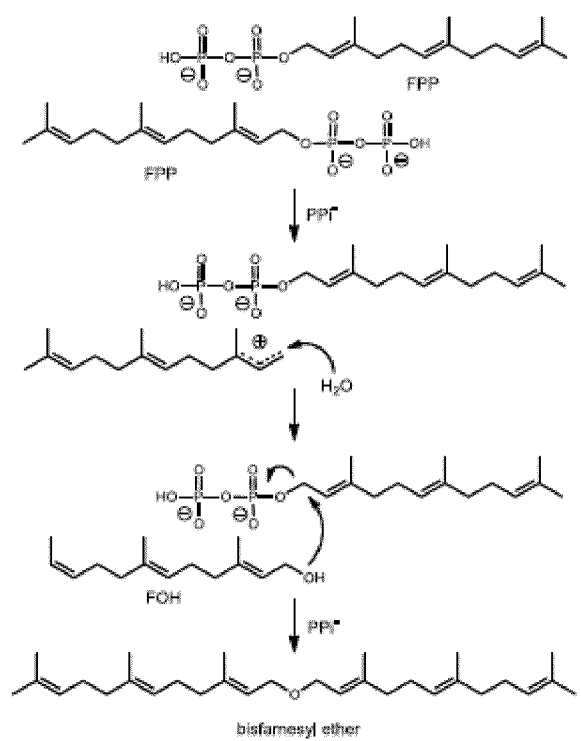
FIG. 9 describes a proposed mechanism for bisfarnesyl ether biosynthesis by SSL-2. When 2 molecules of FPP are bound by the SSL-2 enzyme, ionization of the diphosphate substituent from one creates a carbocation, which can react with a water molecule in close proximity to generate farnesol, FOH. If the FOH becomes appropriately positioned relative to the second FPP molecule, then a Williamson ether synthesis (32) reaction could occur to yield bisfarnesyl ether.

When incubated by itself, SSL-2 catalyzes the NADPH-dependent biosynthesis of approximately ~90% bisfarnesyl ether and 10% squalene (FIG. 6G). This suggests that SSL-2 does have the ability to generate PSPP, but at a much lower efficiency relative to ether formation. Based on a consideration of the detailed carbocation mechanism elucidated for the biosynthesis of squalene from FPP (FIG. 1B) (23), one might not expect bisfarnesyl ether biosynthesis to involve a PSPP intermediate. Instead, if the initial carbocation generated on one of the two SSL-2 bound FPP molecules were quenched by reaction with an available water molecule, and if the so formed farnesol (FOH) were positioned in the correct orientation and proximity to a second FPP molecule, displacement of the pyrophosphate group via a $S_N2$ Williamson ether synthesis-type reaction (32) could yield the bisfarnesyl ether (FIG. 9). Support for such a mechanism comes from the incorporation of radiolabeled FOH directly into the bisfarnesyl ether product, but only when SSL-2 is incubated with both FOH and FPP (Table 1).

TABLE 1

Substrate specificity of SSL-2.

| Substrate | Bisfarnesyl ether formed (pmoles /h · μg protein) |
|---|---|
| $^3$H-farnesol | 0 |
| FPP + $^3$H-farnesol | 16.3 +/− 0.4 |
| $^3$H-FPP | 13.5 +/− 3.3 |

Purified SSL-2 protein (2 μg) was incubated with either 10 μM 1-$^3$H-farnesol, 10 μM 1-$^3$H-farnesol plus 10 μM FPP, or 10 μM 1-$^3$H-FPP in a 50 μl reaction at 37° C. for 1 h, the reaction products extracted with MTBE, and aliquots separated on silica TLC plates. The radioactivity incorporated in the zones corresponding to bisfarnesyl ether were determined by scintillation counting. Data represents mean±S.E.M.

To determine if the mechanism of NADPH dependence for bisfarnesyl ether formation by SSL-2 was catalytic or structural, the quantitative yield of reaction product and NADPH oxidation were determined. While the biosynthesis of 1072 pmoles of squalene was correlated with an equal stoichiometric oxidation of 1098 pmoles of NADPH by the *Nicotiana benthamiana* squalene synthase enzyme, greater than 21 pmoles of bisfarnesyl ether were formed by SSL-2 when only 4.6 pmoles of NADPH were oxidized (Table 2). Approximately half of the NADPH oxidation by SSL-2 under these conditions could be associated with the biosynthesis of 2.2 pmoles of squalene (Table 51). Hence, about 10 times more bisfarnesyl ether is formed per mole equivalent of NADPH oxidation (21 pmoles versus 2.4 pmoles), more consistent with an allosteric or structural role for NADPH in the SSL-2 bisfarnesyl ether reaction rather than a catalytic one. A similar role for NADPH in stimulating PSPP formation by squalene synthases was reported earlier (29, 33, 34).

TABLE 2

NADPH oxidation is correlated with squalene biosynthesis catalyzed by the *Nicotiana benthamiana* squalene synthase (TSS) and SSL-2 enzymes, but not bisfarnesyl ether biosynthesis by SSL-2 enzyme.

| | pmoles NADPH oxidized per μg protein | pmoles squalene recovered per μg protein | pmoles bisfarnesyl ether recovered per μg protein |
|---|---|---|---|
| TSS | 1098.6 ± 59.6 | 1072.6 ± 63.6 | — |
| SSL-2 | 4.6 ± 2.6 | 2.2 ± 0.4 | 21.7 ± 1.8 |

With reference to Table 2, Assays were performed as described above in the Methods except that an alternative reaction buffer (50 mM Tris pH 8.0, 250 mM NaCl, 20 mM MgCl2) was used to minimize spontaneous NADPH oxidation and prevent protein precipitation at high concentrations. All the assays also contained 100 μM NADPH and 40 μM FPP in 300 μl final reaction volumes and the oxidation of NADPH monitored at 340 nm with a Biorad SmartSpec Plus at room temperature (23° C.). An extinction coefficient of 6220/M/cm was used to calculate the amount of NADPH oxidized. No NADPH oxidation could be measured in complete reaction buffer without protein over a 1 h incubation. When either TSS or SSL-2 was incubated in reaction buffer without FPP, NADPH was oxidized at a rate of 24 and 22 pmoles/μg protein/h, respectively, suggesting that both enzymes cause a slight oxidation of NADPH that is uncoupled with squalene or bisfarnesyl ether biosynthesis. This background NADPH oxidation was subtracted from the experimental determined rates. The experimental enzyme assays contained either purified TSS (0.75 or 1.5 μg) or SSL-2 (8 or 16 μg) and 40 μM $^3$H-FPP. Absorbance at 430 nm was recorded every 2.5 min. for 15 minutes, after which the reaction was stopped by adding an equal volume of 0.5 M EDTA. The reaction mixture was collected, extracted with 200 μl of hexane and aliquots were separated by silica TLC along with standards of squalene and bisfarnesyl ether using hexane:MTBE (25:1) as the developing solvent. The standards were subsequently visualized with iodine vapor, and corresponding zones analyzed by scintillation spectroscopy. Data represents mean±S.E.M of duplicate samples.

Improving the Efficiency of Botryococcene Biosynthesis.

Figure 10:
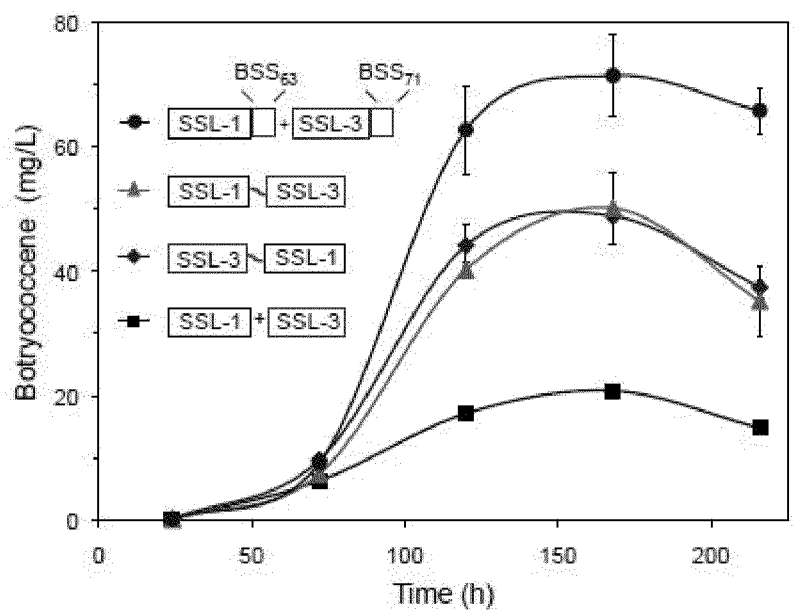
FIG. 10 includes a comparison of botryococcene production in yeast engineered with different configurations of SSL-1 and SSL-3. Yeast line TN7 was engineered with the SSL-1 and SSL-3 genes on separate plasmids (squares), with gene fusions (SSL-1 fused to SSL-3 via a triplet repeat of GGSG (triangles), or vice versa (diamonds)), or with 63 or 71 amino acids of the carboxy terminus of the *Botryococcus* squalene synthase, sequences containing a membrane spanning domain, appended to the carboxy termini of the SSL-1 and SSL-3 enzymes, respectively (circles). The data represents mean±S.E.M.

Production of botryococcene by yeast was improved by engineering different configurations of the SSL-1 and 3 genes (FIG. 10). While co-expression of SSL-1 and SSL-3 yielded significant botryococcene, peptide fusions of SSL-1 and SSL-3 connected by a triplet repeat linker of GGSG improved production capacity greater than 2-fold to upwards of 50 mg/L. Further enhancement to over 70 mg/L was observed by appending the carboxy-terminal 63 or 71 amino acids of the *Botryococcus* squalene synthase onto the carboxy-termini of SSL-1 and SSL-3 enzymes, respectively. These terminal amino acids serve to tether squalene synthase, and by inference SSL-1 and 3, to the yeast's endo-membrane system, which might bring the enzymes in closer proximity to one another or give the enzymes greater access to endogenous FPP pools. Further support for this notion has been the observation of greater than 100 mg/L of botryococcene by yeast over-expressing gene fusions of SSL-1 and SSL-3 harboring the putative ER membrane targeting sequence of the *botryococcus* squalene synthase.

Discussion—

Figure 11:
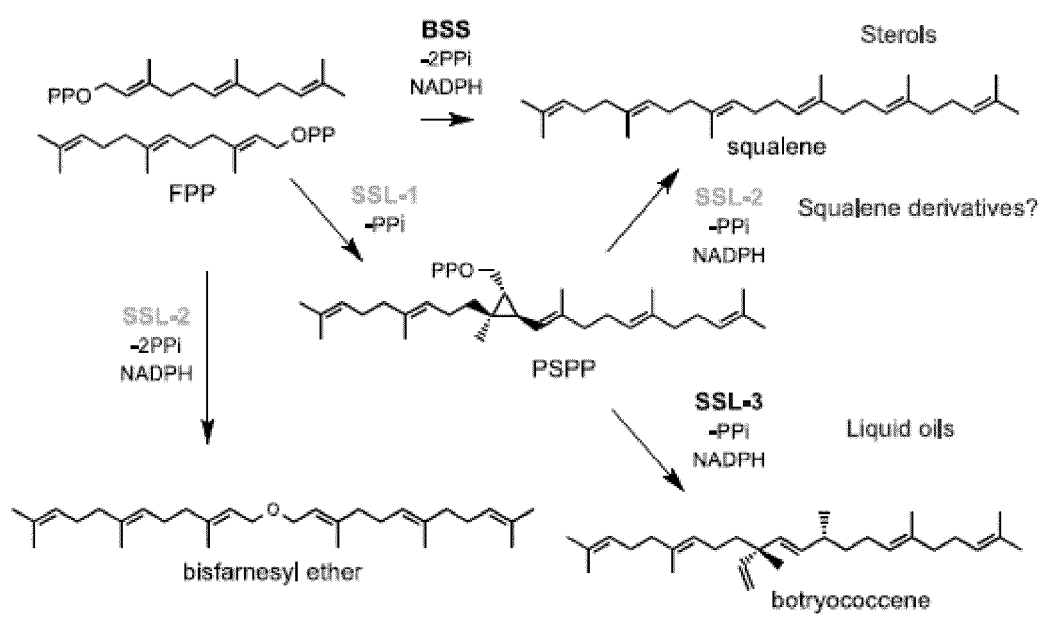
FIG. 11 depicts the catalytic roles of the squalene synthase-like enzymes in *Botryococcus braunii* race B and their putative contributions to the triterpene constituents that accumulate. The previously identified squalene synthase gene (BSS) (31) is thought to provide squalene essential for sterol metabolism, whereas the squalene synthase-like genes SSL-1, SSL-2 and SSL-3 provide for the triterpene oils serving specialized functions for the algae. In combination with SSL-1, SSL-2 could provide squalene for extracellular matrix.

The results presented here were unexpected because squalene biosynthesis is known as a two-step process catalyzed by a single enzyme (FIG. 11). FPP is first converted to the intermediate PSPP, followed by its reductive rearrangement to squalene (24). However, PSPP is not evident in these reactions unless NADPH, the reducing reagent, is omitted from the incubations (19). Under conditions of adequate NADPH, it appears unlikely that PSPP is released from the squalene synthase enzyme, then re-bound as a natural consequence of the catalytic cycle (34). Regardless, a single enzyme is responsible for the entire conversion process and this mechanism appears highly conserved from yeast to man, including algae like *Botryococcus* (31). In contrast, botryococcene biosynthesis appears to require the successive action of two distinct enzymes. First SSL-1 catalyzes the biosynthesis of PSPP as a separate and distinct product, which the second enzyme, SSL-3, efficiently converts to botryococcene in a NADPH-dependent manner. Whatever the evolutionary forces driving this division of labor might have been, it also appears to have occurred twice within the life history of *Botryococcus*. When SSL-1 is co-expressed with SSL-2, squalene accumulates, which the present inventors speculate might represent a distinct pool of squalene in *Botryococcus* destined to specialized roles like the biogenesis of the extracellular matrix and other squalene derivatives.

Support for the neofunctionalization of these unusual binary systems for triterpene biosynthesis is provided by the distinctive biosynthetic activities associated with SSL-2 (FIG. 11). First, this enzyme catalyzes the NADPH-dependent biosynthesis of an unusual terpene ether. There are no reports of bisfarnesyl ether accumulation in *Botryococcus* or any other organism, but it could be incorporated into other more complex matrix polymers masking its detection. One possible means for bisfarnesyl ether biosynthesis does not involve a PSPP intermediate, but instead an alternative reactivity of two bound farnesyl moieties via a $S_N2$ Williamson ether synthesis-type reaction (FIG. 9) (32). Support for such a mechanism comes from the incorporation of radiolabeled FOH directly into the bisfarnesyl ether product, but only when SSL-2 is incubated with both FOH and FPP (Table 1). Second, the accumulation of both squalene and bisfarnesyl ether in yeast co-expressing SSL-1 and SSL-2 is also consistent with this proposed mechanism. The yeast line used for these studies is engineered for high FPP production, but tends to accumulate FOH as a consequence of FPP dephosphorylation catalyzed by endogenous phosphatases (35, 36). Hence, the yeast co-expressing SSL-1 and SSL-2 have significant pools of FOH and FPP, which will compete with any PSPP generated by SSL-1 for binding and catalysis by SSL-2. Third, while there is no obvious or direct chemical requirement for reducing equivalents in the biosynthesis of the bisfarnesyl ether from FPP and FOH, the significance of the NADPH dependence might relate to a structural role rather than a catalytic one. Pandit et al. (29) suggested that NADPH binding to its putative bind site in the human squalene synthase might stabilize a region of the enzyme not well resolved in the crystal structure, and thus positioning a domain into close association with the active site. NADPH binding to the SSL-2 enzyme could evoke a similar conformational change that renders the SSL-2 enzyme competent for either bisfarnesyl ether or squalene biosynthesis dependent on available substrates (FPP, FOH and PSPP). Hence, not only has SSL-2 maintained its catalytic ability to convert PSPP to squalene, it has evolved a novel catalytic activity yielding a bisprenyl ether from prenyl diphosphates.

One possibility for how these unique triterpene synthases arose is that a progenitor squalene synthase gene could have duplicated to yield multiple gene copies. While one copy (BSS) maintained its coding capacity for squalene synthase activity, essential for sterol metabolism, the other copies (SSL-1, SSL-2 and SSL-3) would have afforded opportunities for evolutionary diversification. Alternatively, *Botryococcus* could have acquired multiple copies of SSL genes by a horizontal gene transfer process and those genes may have evolved specialized synthase-like activities. For example, one of the acquired squalene synthase like genes could have evolved the capacity for botryococcene biosynthesis and a subsequent gene duplication event could have resulted in loss of function for either the first half reaction or the second (45). No matter the specific mechanism, what makes the possible events associated with the neofunctionalization of the SSL enzymes particularly intriguing is that specialized triterpene oil accumulation, like botryococcene, could not have occurred without both SSL-1 and SSL-3 evolving in concert with one another.

There are other examples of similar division and diversification of enzymological capacities within key genes for pyrimidine (37), diterpene (38) and triterpene (39) metabolism. For instance, biosynthesis of the diterpene kaurene in many fungi relies on a single, multifunctional enzyme (40) that catalyzes the conversion of the linear isoprenoid intermediate geranylgeranyl diphosphate to the bicyclic copalyl diphosphate (CPP) product. CPP then undergoes a second cyclization reaction initiated at a separate binding site on the same enzyme to yield kaurene. In higher plants, the enzymes for CPP and kaurene biosynthesis are encoded by separate and distinct genes (38). Specific CPP synthases within rice catalyze the biosynthesis of either ent-CPP or syn-CPP isomers (41, 42). These are complemented with equally distinct diterpene synthases that can utilize one or the other CPP isomer for hormone or defense compound biosynthesis (43, 44). Yet, there are other diterpene synthases that have retained these two enzyme functions, but have evolved whole new catalytic outcomes (45). Osbourn and co-workers (39, 46) have also provided evidence that the genes encoding for the enzymes catalyzing the cyclization of oxidosqualene to distinct tetra- and penta-cyclic classes of triterpenes, primarily sterols and defense related saponins, respectively, likely arose from common ancestor genes evolving novel catalytic functions dedicated to primary and specialized metabolism. Microbial forms of dihydrosqualene synthase, like CrtM, might also be considered an example of squalene synthase-like enzyme diversification (47, 48). CrtM relies on PSPP biosynthesis, but does not utilize NADPH for the second half reaction. CrtM instead yields dehydrosqualene, a reaction product with much in common with phytoene, the tetraterpene equivalent of dehydrosqualene, and by inference shares catalytic features of the second half reaction in common with phytoene synthase. Nonetheless, what distinguishes the current results from all the others is there are no other known examples where the half-reaction specificity of squalene synthases appear separated from one another and subject to evolutionary diversification, except for that reported here for *Botryococcus*.

The family of squalene synthase-like enzymes in *Botryococcus* is also informative relative to the recent elucidation of the crystal structure of dehydrosqualene synthase (CrtM) of *Staphylococcus aureus*, a target enzyme for a new generation of anti-infective reagents, along with refinements in the human squalene synthase structure (47, 48). Those studies detailed how two FPP molecules bind to CrtM and human squalene synthase, are converted to the PSPP intermediate, and then re-positioned in the active site pocket in preparation for the second half reaction. Key residues identified include those that coordinate magnesium ions for their interactions with the diphosphate substituents of the FPPs and PSPP, and hence considered involved in both half-reactions. Based on sequence alignments (FIG. 2), many of these residues (S19, Y41, R45, D48, D52, Y129, N168, and D177, numbering according to CrtM and annotated by a star above the residue in FIG. 2) appear conserved in the *Botryococcus* squalene synthase and all three of the SSL enzymes. Because SSL-2 and SSL-3 are deficient in PSPP biosynthesis, these particular residues are not by themselves sufficient for PSPP biosynthesis. Conversely, since SSL-1 can only catalyze the formation of PSPP, these same residues do not appear sufficient to initiate the second half reaction. Amino acids at other positions are undoubtedly important for PSPP formation and the catalytic specificity of the second half reaction, squalene versus botryococcene biosynthesis. Experiments to functionally define which amino acids at which positions are responsible for the enzymological specificity of these triterpene synthases will be significantly advantaged by having these unique *Botryococcus* SSL enzymes which are specialized to either the first half-reaction or the second.

Altogether, the results establish that botryococcene and squalene oils are synthesized in *Botryococcus braunii* race B by the combined action of separate and distinct squalene synthase-like enzymes, have opened up new avenues for understanding the chemical specificity and diversification within this class of enzymes, and provide a demonstration for the bioengineering and production of a key petrochemical replacement.

Methods

The squalene synthase-like cDNAs were isolated either by screening a *Botryococcus* cDNA library using low stringency hybridization conditions with a radio labeled *Botryococcus* squalene synthase probe (yielding SSL-1), or by computational screening of the combined *Botryococcus* transcriptomic datasets with the *Botryococcus* squalene synthase cDNA sequence (yielding SSL-2 & SSL-3). These three genes were inserted into the pET28a vector for bacterial expression and the YEp352 or pESC vectors for yeast expression. Bacterial expressed enzymes were purified, incubated with FPP or [1-$^3$H]FPP, and hexane extracts analyzed either by GC-MS, or by scintillation counting of the indicated products isolated by TLC, respectively. Various combinations of the SSL genes were transformed into the TN7 yeast line, the transformants grown in either YPDE or SCE media, and organic extracts of the cultures analyzed by GC-MS. TN7 was created by insertional mutagenesis of the ERG1 gene in the Cali-7 yeast line. The unknown terpene accumulating in TN7 expressing SSL-2 was purified by silica-HPLC, then subjected to standard NMR analyses along with chemically synthesized bisfarnesyl ether. Additional details are described below.

Reagents. [1-$^3$H]Trans, trans farnesol, and [1-$^3$H]FPP were purchased from ARC (St. Louis, Mo.). All other reagents were purchased from Sigma (St. Louis, Mo.) unless stated otherwise.

Culturing of *B. braunii*. *Botryococcus braunii* Berkeley (Showa) strain was grown as previously described (Okada, et al. (2004)), except that cultures were aerated with filter sterilized air containing 2.5% $CO_2$. Algal cells were collected by vacuum filtration using a 20 µM nylon mesh, then scrapped into collection tubes, snap frozen in liquid $N_2$ and stored at −80° C. until further use.

Cloning SSL-1.

Plaque lifts of a *B. braunii* cDNA library previously described by Okada et al. (2000) were prepared and hybridized with the full-length *B. braunii* squalene synthase cDNA radiolabeled with [α-$^{32}$P]dCTP using a Prime-It kit (Stratagene). Hybridization was performed at 30° C. in hybridization buffer consisting of 5×SSPE, 2×Denhardt's solution, 0.2% SDS, 100 µg ml$^{-1}$ salmon sperm DNA and 40% formamide Okada et al. (2000)). The plaque lifts were washed three times at room temperature for 5 min with 2×SSC, 0.1% SDS and hybridization detected by autoradiography. After 2 rounds of plaque purification, isolated plaques were converted to their plasmid forms according to the manufacturer's instructions (Stratagene), restriction digestions of the isolated plasmids compared, and only those showing distinctive differences to that for the *Botryococcus* squalene synthase examined further by automated DNA sequencing. DNA sequence of the squalene synthase-like (SSL-1) cDNA clone yielded a putative full-length open reading frame (ORF) coding for a 402 amino acid protein having a predicted molecular size of 45,692 daltons.

SSL-1 was cloned into the pET28a vector via the cloning site BamHI/XhoI in order to generate a SSL-1 protein with an amino terminal hexa-histidine extension to aid in purification. The SSL-1 gene was also inserted into two standard yeast expression vectors, YEp352 harboring an ADH1 promoter and Ura3 selection via the cloning site EcoRI/HindIII, and pESC harboring an AHD1 promoter and Leu2 selection via the cloning site BamHI/NotI (Takahashi, et al (2007).

Cloning SSL-2.

Transcriptomic sequencing was performed using RNA pooled from *B. braunii* cultures ranging from 1-4 weeks after subculturing. cDNA samples were prepared for de novo transcriptome sequencing similar to the protocol of Meyer et al. (2009), and the resulting cDNA samples processed for DNA sequencing according to the emPCR Method Manual (Roche). Sequencing was performed on a Roche Genome Sequencer FLX and the data assembled using Newbler (Roche). The assembled DNA sequence data was computationally screened using the NCBI blast search function with the *Botryococcus* squalene synthase cDNA sequence as the query, which revealed a partial ORF with strong similarity to the amino terminal halves of BSS and SSL-1. To determine the full length sequence for this SS-like gene (termed SSL-2), an aliquot of plasmid DNA derived from the phage cDNA library described above (using the mass excision protocol as described by Stratagene) was used in PCR reactions with primers specific to SSL-2 and primers specific to the pBluescript SK-vector in attempt to amplify the missing 3' sequence of SSL-2. An 800 by band was isolated, ligated into the pGEM T-Easy vector (Promega), and sequenced. This sequence information was used to deduce the full length sequence for SSL-2, which encodes for a predicted protein consisting of 465 amino acids and having a molecular size of 52,149 daltons.

The full length SSL-2 cDNA was cloned into the Yep352 yeast expression vector via the cloning site EcoRI/NotI. Because SSL-2 encodes for a protein with at least one predicted membrane spanning region at its C-terminus, we designed a truncated form of SSL-2 in which 73 C-terminal amino acids were deleted (SSL-2-tr2). SSL-2-tr2 was cloned into the pET28a vector via the cloning site EcoRI/NotI.

Cloning SSL-3.

The DNA sequence data obtained from a second transcriptomic profiling effort (www.jgi.doe.gov/sequencing/why/bbraunii.html) was combined with the first, and the combined dataset assembled with CLC Genomics Workbench (CLC Bio). Screening of this dataset with the *Botryococcus* squalene synthase revealed another ORF encoding a 383 amino acid squalene synthase-like (SSL-3) protein with a predicted molecular size of 44,127 daltons. SSL-3 was cloned into the pET28a and Yep352 vectors via the cloning sites EcoRI/NotI.

Protein Expression, Purification, and Enzyme Assays.

The recombinant vectors were transformed into *E. coli* strain BL21(DE3) according to the manufacturer's recommendations (Novagen). The selected lines were grown with kanamycin selection at 37° C. with vigorous shaking until the cultures reached an optical density of ~0.8 ($OD_{600}$ nm), then expression of the corresponding SSL gene induced by addition of 0.5 mM isopropylthio-β-D-galactoside (IPTG) and the cultures incubate for an additional 3 to 20 h with shaking at room temperature. One hundred ml of the culture was subject to centrifugation at 4,000 g for 10 min, the pelleted cells resuspended in 10 ml of lysis buffer containing 50 mM $NaH_2PO_4$, pH 7.8, 300 mM NaCl, 10 mM imidazole, 1 mM $MgCl_2$, 1 mM PMSF, 1% glycerol (v/v), then sonicated 4× for 10 sec with a microprobe sonicator at 60% maximum power. The samples were cooled on ice for 2 min between sonication treatments. The sonicate was centrifuged at 16,000 g for 10 min at 4° C. and the supernatant used for purification of the hexa-histidine tagged enzymes.

Purification of the bacterial expressed enzymes was afforded by the amino-terminal hexa-histidine tag using His-Select Cobalt affinity gel (Sigma) columns according the manufacturer's recommendations. Recovery of proteins with the expected molecular sizes was determined by SDS-PAGE. The purified protein fractions were concentrated using Amicon Ultra (0.5 ml, 10K) centrifugation filter units and stored in 300 mM NaCl, 20 mM Tris-HCl pH 7.5, 5 mM dithiothreitol, 2 mM $MgCL_2$, 50% glycerol (v/v) at −20° C. for 2-3 weeks without noticeable loss of activity.

Typical enzyme assays were initiated by mixing aliquots of purified enzyme with 50 mM Mops, pH 7.3, 20 mM $MgCl_2$, 2.5 mM 2-mercaptoethanol, 10 μM [1-$^3$H]-FPP (~2×10$^5$ dpm total), and 2 mM NADPH in total reaction volume of 50 μl. Reactions were incubated at 37° C. for 1 h and then extracted with 100 μl n-hexane or 100 ul MTBE. Forty μl of the n-hexane or MTBE extract was then spotted onto silica TLC plates with authentic standards of botryococcene and squalene and developed with n-hexane, or standards of bisfarnesyl ether and developed with n-hexane:MTBE, 25:1. The standards were visualized with iodine vapors and TLC zones corresponding to the standards were scrapped and analyzed by scintillation spectrometry. If *Botryococcus* lysate was added to enzyme assays, typically 5 μl of lysate (corresponding to 10 μg total protein) prepared from *B. braunii* cells according to Okada et al. (1) was added. Cold assays were scaled up to 0.5 ml total volume and contained 10 μM FPP. Assays were extracted once with 1 ml n-hexane, then with 1 ml MTBE, the organic extracts pooled, and solvent evaporated under a stream of $N_2$. Extracts were resuspended in 50 μl hexane and an aliquot analyzed by GC-MS with a Varian CP-3800 GC coupled to a Varian Saturn 2200 MS/MS (Varian Medical Systems) using a Supelco SLB-5 ms fused silica capillary column (30 m×0.25 mm×0.25 μM film thickness, Supelco). Initial oven temperature was set at 220° C. for 1 min., ramped to 280° C. at 1° C./min., then ramped to 300° C. at 3° C./min.

For reactions requiring dephosphorylation of reaction products like PSPP, the reactions were extracted 3× with 200 μA water saturated 1-butanol and pooled in a 4 ml glass screw cap vial. The butanol was evaporated with $N_2$ and the white residue resuspended in 2 ml of acid phosphatase solution (20% 1-propanol (v/v), 100 mM sodium acetate pH 4.7, 0.1% Triton X-100, 10 units sweet potato acid phosphatase) and incubated overnight (12-16 h) in a 28° C. shaker. Dephosphorylated products were then extracted 3× with 1 ml n-hexane, pooled, dried with $N_2$, and resuspended in 50-200 μl of n-hexane. Aliquots of the hexane extract were spotted onto reverse-phase TLC plates along with standards of FOH and PSOH and developed with methanol:acetone (8:2). The standards were visualized with iodine vapors and the zones corresponding to FOH (rf=0.65) and PSOH (rf=0.45) were scraped and analyzed by scintillation spectroscopy.

Expression in Yeast.

A yeast line, CALI-7, developed previously for the generation of high intracellular concentrations of FPP was used for these purposes (Meyer, et al (2009), Song (2003)). One further modification was an insertional inactivation of the ERG 1 gene (Jandrositz, et al. (1991). The insertional mutation of this gene was created by introducing the TRP1 gene flanked by DNA sequences of the 5' and 3' region of the ERG 1 gene into the CALI-7 cells and subsequent selection for reversion of tryptophan auxotrophic growth according to the method of Wang et al. (2004). This modified yeast line capable of accumulating high levels of FPP but not metabolizing squalene is referred to as TN7.

The various recombinant yeast expression vectors were introduced into the TN7 yeast line via lithium acetate transformation, followed by selection for uracil and leucine auoxtrophic growth (Takahashi, et al. (2007)). Yeast lines were confirmed to possess the various expression vectors by colony PCR. Individual colonies of TN7 and the various TN7-transformants were subsequently grown in 25 ml of YPDE (nutrient rich) or Yeast Synthetic Drop-out medium (selection) for the indicated time at 25° C. before analyzing the cultures for production of novel triterpene components. In brief, 1 ml aliquots of the culture were combined with 1 ml of acetone, vigorously mixed, and incubated at room temperature for 10 min. One ml of hexane was added and mixed vigorously for 60 sec. The mixture was then centrifuged briefly at 500 g to separate the phases, and the organic phase removed and concentrated to dryness under a nitrogen stream. The dried extract was resuspended in 50-500 μl of n-hexane and a 1 μl aliquot analyzed by GC-MS as described above.

SSL-1 and SSL-3 Yeast Expression Constructs.

Fusion constructs were created by employing an assembly PCR strategy as described by Sun et al (2009). For creation of the SSL-1-SSL-3-fusion construct, oligonucleotide primers (5'-ccgGAATTCaaaacaatgactatgcaccaagaccacgg (SEQ ID NO: 28), EcoR1 restriction site in bold, and 5'-ACCAGAAC-CACCACCAGAACCACCACCAGAACCAC-Ccttggtgggagttg gggctgcgc (SEQ ID NO: 29), (GGSG)×3 linker in bold) were used with SSL-1 as the template to amplify SSL-1 with a 3'-extension, and oligonucleotide primers (5'-GGTGGTTCTGGTGGTGGTTCTGGTGGTG-GTTCTGGTatgaaacttcgggaagtcttgc (SEQ ID NO: 30), (GGSG)×3 linker in bold, and 5'-ataagaatGCGGCCGCctaagcacccttagctgaaacc (SEQ ID NO: 31), NotI restriction site in bold) were used with SSL-3 as the template to amplify SSL-3 with a 5'-extension. The two PCR amplification products were purified and both used in a subsequent PCR reaction with the flanking oligonucleotide primers (5'-ccgGAATTCaaaacaatgactatgcaccaagaccacgg (SEQ ID NO: 32), EcoR1 restriction site in bold, and 5'-ataagaatGCGGCCGCctaagcacccttagctgaaacc (SEQ ID NO: 33), NotI restriction site in bold). The fused amplification product was purified, digested with EcoRI and NotI, and ligated into YEp352 (YEp352-SSL-1-3-fus). The SSL-3-SSL-1-fusion construct was created similarly (YEP352-SSL-3-1-fus), except that the oligonucleotide primers (5'-cggGAATTCaaaacaatgaaacttcgggaagtcttgcagc (SEQ ID NO: 34), EcoRI restriction site in bold, and 5'-ACCAGAACCAC-CACCAGAACCACCACCAGAACCACCag-cacccttagctgaaaccttcc (SEQ ID NO: 35), (GGSG)×3 linker in bold) were used with SSL-3 as the template and oligonucleotide primers (5'-GGTGGTTCTGGTGGTG GTTCTG-GTGGTGGTTCTGGTatgactatgcaccaaga ccacgg (SEQ ID NO: 36), (GGSG)×3 linker in bold, and 5'-ataagaatGCGGC-CGCttacttggtgggagttggggctg cgc (SEQ ID NO: 37), NotI restriction site in bold) were used with SSL1 as the template.

The SSL1-BSS$_{63}$ construct was created using the same assembly PCR methodology with oligonucleotide primers (5'-cgcGGATCCaaaacaatgactatgcaccaagaccacgg (SEQ ID NO: 38), BamHI restriction site in bold, and 5'-gcgctaacaact-tggtgggagttggggctgcgcagaaagatttc (SEQ ID NO: 39) with SSL-1 as the template to amplify SSL-1 with a 3'-extension, and oligonucleotide primers 5'-ctcccaccaagttgttagcgctgacgg-gaggcagcttctacc (SEQ ID NO: 40), and 5'-ataaagaatGCGGC-CGCttaggc gctgagtgtgggtctagg (SEQ ID NO: 41), NotI site in bold) with BSS as the template to amplify the c-terminus of BSS with a 5'-extension. Following completion of the assembly PCR protocol, the amplification product was digested with BamHI and NotI and ligated into pESC (pESC-SSL-1-BSS$_{63}$). The SSL-3-BSS$_{71}$ construct was created in the same manner except that oligonucleotide primers (5'-cggGAAT-TCaaaacaatgaaacttcgggaagtcttgcagc (SEQ ID NO: 42), EcoRI restriction site in bold, and 5'-cgtcaaaggtagcaccct-tagctgaaaccttccatttgattttg (SEQ ID NO: 43) were used with SSL-3 as the template and (5'-gctaagggtgctaccttttgacgaat-tgaggagcaggttgttagcg (SEQ ID NO: 44), and 5'-ataaagaat-GCGGCCGCttaggcgctgagtgtgggtctagg (SEQ ID NO: 45), NotI site in bold) were used with BSS as the template. The assembly PCR amplicon was ligated into YEp352 (YEP352-SSL$_3$-BSS$_{71}$).

Purification of Bisfarnesyl Ether.

TN7 yeast containing YEp352-SSL2 was grown in 1 L YPDE media at 25° C. for 8 days, after which hexane extracts were prepared. The raw yeast extracts were then subject to HPLC separation on a Waters 2695 HPLC with a Waters 2996 Photodiode Array detector (Waters Corporation) and a Develosil 60-3, 250 mm×20 mm column (Nomura Chemical), run with an isocratic solvent (n-hexane:MTBE, 50:1) at 8 ml/min. Under these conditions, bisfarnesyl ether eluted at ~16 min. Further purification of the bisfarnesyl ether was afforded by successive chromatographic runs.

Synthesis of (2E,6E)-3,7,11-trimethyl-1-1-((2E,6E)-3,7,11-trimethyldodeca-2,6,10-trienyloxy)dodeca-2,6,10-triene or Bisfarnesyl Ether To 81 mg (2.03 mmole, 2 eq) of 60% sodium hydride (washed with anhydrous hexanes to remove mineral oil) in 1 mL of anhydrous THF under an argon atmosphere at 0° C., 228 mg (1.02 mmol) of trans,trans-farnesol in 1 mL of anhydrous THF was added. The mixture was stirred for 10 min, then 438 mg (1.53 mmol, 1.5 eq) of trans,trans-farnesol bromide was added in 0.5 ml of anhydrous THF. The mixture was stirred for 20 h and allowed to warm to 25° C. The reaction was quenched with 2 mL of 1M HCl, diluted with EtOAc, washed successively with water and brine and dried over anhydrous MgSO$_4$. The crude product was chromatographed on silica gel F254 preparative TLC plates (Merck) in 1:10 EtOAc:hexanes to afford 174 mg (40%) of bisfarnesyl ether that had NMR and mass spectral data identical to that of material produced in enzymatic reactions (FIG. 7).

NMR of Bisfarnesyl Ether.

$^1$H and $^{13}$C NMR spectra were recorded on a JEOL alpha 600 NMR spectrometer at 300K. Chemical shifts were referenced relative to solvent peaks, namely $\delta_H$ 7.24 and $\delta_C$ 77.00 for CDCl$_3$. Results are shown in FIG. 7.

Throughout this document, various references are mentioned. All such references are incorporated herein by reference to the same extent as if each individual reference was specifically and individually indicated to be incorporated by reference, including the references set forth in the following list:

REFERENCES

1. Brown A C, Knights B A, Conway E (1969) Hydrocarbon content and its relationship to physiological state in green alga *botryococcus braunii*. *Phytochemistry* 8:543-547.
2. Metzger P, Largeau C (2005) *Botryococcus braunii*: A rich source for hydrocarbons and related ether lipids. *Appl Microbiol Biotech* 66:486-496.
3. Gelpi E, Oro J, Schneide H J, Bennett E O (1968) Olefins of high molecular weight in 2 microscopic algae. *Science* 161:700-701.
4. Metzger P, Allard B, Casadevall E, Berkaloff C, Coute A (1990) Structure and chemistry of a new chemical race of *Botryococcus braunii* (Chlorophyceae) that produces lycopadiene, a tetraterpenoid hydrocarbon. *J Phycol* 26:258-266.
5. Okada S, Murakami M, Yamaguchi K (1995) Hydrocarbon composition of newly isolated strains of the green microalga *Botryococcus braunii*. *J Appl Phycol* 7:555-559.
6. Weiss T L, et al. (2010) Raman spectroscopy analysis of botryococcene hydrocarbons from the green microalga *Botryococcus braunii*. *J Biol Chem* 285:32458-32466.
7. Metzger P, Rager M N, Largeau C (2007) Polyacetals based on polymethylsqualene diols, precursors of algaenan in *botryococcus braunii* race b. *Org Geochem* 38:566-581.
8. Huang Z, Poulter C D (1989) Tetramethylsqualene, a triterpene from *Botryococcus braunii* var *Showa*. *Phytochemistry* 28:1467-1470.
9. Metzger P, Berkaloff C, Casadevall E, Coute A (1985) Alkadiene-producing and botryococcene-producing races of wild strains of *Botryococcus braunii*. *Phytochemistry* 24:2305-2312.
10. Metzger P (1999) Two terpenoid diepoxides from the green microalga *Botryococcus braunii*: Their biomimetic conversion to tetrahydrofurans and tetrahydropyrans. *Tetrahedron* 55:167-176.
11. Metzger P, Rager M N, Largeau C (2002) Botryolins A and B, two tetramethylsqualene triethers from the green microalga *Botryococcus braunii*. *Phytochemistry* 59:839-843.

12. Okada S, Tonegawa I, Matsuda H, Murakami M, Yamaguchi K (1997) Braunixanthins 1 and 2, new carotenoids from the green microalga *Botryococcus braunii*. *Tetrahedron* 53:11307-11316.
13. Derenne S, et al. (1997) Chemical structure of the organic matter in a pliocene maar-type shale: Implicated *Botryococcus* race strains and formation pathways. *Geochim Cosmochim Acta* 61:1879-1889.
14. Glikson M, Lindsay K, Saxby J (1989) *Botryococcus*—a planktonic green-alga, the source of petroleum through the ages—transmission electron microscopical studies of oil shales and petroleum source rocks. *Org Geochem* 14:595-608.
15. Mastalerz M, Hower J C (1996) Elemental composition and molecular structure of *Botryococcus* alginite in westphalian cannel coals from Kentucky. *Org. Geochem* 24:301-308.
16. Moldowan J M, Seifert W K (1980) 1st discovery of botryococcane in petroleum. *J Chem Soc-Chem Comm* 912-914.
17. Hillen L W, Pollard G, Wake L V, White N (1982) Hydrocracking of the oils of *Botryococcus braunii* to transport fuels. *Biotech Bioeng* 24:193-205.
18. Banerjee A, Sharma R, Chisti Y, Banerjee U C (2002) *Botryococcus braunii*: A renewable source of hydrocarbons and other chemicals. *Crit. Rev Biotech* 22:245-279.
19. Jarstfer M B, Zhang D L, Poulter C D (2002) Recombinant squalene synthase. Synthesis of non-head-to-tail isoprenoids in the absence of NADPH. *J Amer chem Soc* 124:8834-8845.
20. Pan J J, Bugni T S, Poulter C D (2009) Recombinant squalene synthase. Synthesis of cyclopentyl non-head-to-tail triterpenes. *J Org Chem* 74:7562-7565.
21. Zhang D L, Poulter C D (1995) Biosynthesis of non-head-to-tail isoprenoids—synthesis of 1'-1-structures and 1'-3-structures by recombinant yeast squalene synthase. *J Amer Chem Soc* 117:1641-1642.
22. Bergstrom J D, et al. (1993) Zaragozic acids—a family of fungal metabolites that are picomolar competitive inhibitors of squalene synthase. *Proc Natl Acad Sci USA* 90:80-84.
23. Poulter C D (1990) Biosynthesis of non-head-to-tail terpenes—formation of 1'-1 and 1'-3 linkages. *Acc Chem Res* 23:70-77.
24. Rilling H C (1966) A new intermediate in biosynthesis of squalene. *J Biol Chem* 241:3233-3236.
25. Sasiak K, Rilling H C (1988) Purification to homogeneity and some properties of squalene synthetase. *Arch Biochem Biophys* 260:622-627.
26. Blagg B S J, Jarstfer M B, Rogers D H, Poulter C D (2002) Recombinant squalene synthase. A mechanism for the rearrangement of presqualene diphosphate to squalene. *J Amer Chem Soc* 124:8846-8853.
27. Jarstfer M B, Blagg B S J, Rogers D H, Poulter C D (1996) Biosynthesis of squalene. Evidence for a tertiary cyclopropylcarbinyl cationic intermediate in the rearrangement of presqualene diphosphate to squalene. *J Amer Chem Soc* 118:13089-13090.
28. Gu P D, Ishii Y, Spencer T A, Shechter I (1998) Function-structure studies and identification of three enzyme domains involved in the catalytic activity in rat hepatic squalene synthase. *J Biol Chem* 273:12515-12525.
29. Pandit J, et al. (2000) Crystal structure of human squalene synthase—a key enzyme in cholesterol biosynthesis. *J Biol Chem* 275:30610-30617.
30. Robinson G W, Tsay Y H, Kienzle B K, Smithmonroy C A, Bishop R W (1993) Conservation between human and fungal squalene synthetases—similarities in structure, function, and regulation. *Mol Cell Biol* 13:2706-2717.
31. Okada S, Devarenne T P, Chappell J (2000) Molecular characterization of squalene synthase from the green microalga *Botryococcus braunii*, race B. *Arch Biochem Biophys* 373:307-317.
32. Houben J, Weyl T, Müller E (1965) *Methoden der organischen chemie* (G. Thieme, Stutgart, Germany) 4th Ed p 832.
33. Agnew W S, Popjak G (1978) Squalene synthetase—stoichiometry and kinetics of presqualene pyrophosphate and squalene synthesis by yeast microsomes. *J Biol Chem* 253:4566-4573.
34. Radisky E S, Poulter C D (2000) Squalene synthase: Steady-state, pre-steady-state, and isotope-trapping studies. *Biochemistry* 39:1748-1760.
35. Song L S (2003) Detection of farnesyl diphosphate accumulation in yeast erg9 mutants. *Anal Biochem* 317:180-185.
36. Takahashi S, Yeo Y, Greenhagen B T, McMullin T, Song L, Maurina-Brunker J, Rosson R, Noel J P, Chappell J. (2007) Metabolic engineering of sesquiterpene metabolism in yeast. *Biotech Bioeng* 97:170-181.
37. Nara T, Hshimoto T, Aoki T (2000) Evolutionary implications of the mosaic pyrimidine-biosynthetic pathway in eukaryotes. *Gene* 257:209-222.
38. Peters R J (2010) Two rings in them all: The labdane-related diterpenoids. *Nat Prod Rep* 27:1521-1530.
39. Field B, Osbourn A E (2008) Metabolic diversification—independent assembly of operon-like gene clusters in different plants. *Science* 320:543-547.
40. Toyomasu T, et al. (2000) Cloning of a full-length cDNA encoding ent-kaurene synthase from *Gibberella fujikuroi*: Functional analysis of a bifunctional diterpene cyclase. *Biosci Biotechnol Biochem* 64:660-664.
41. Prisic S, Xu M M, Wilderman P R, Peters R J (2004) Rice contains two disparate ent-copalyl diphosphate synthases with distinct metabolic functions. *Plant Physiol* 136:4228-4236.
42. Xu M M, Hillwig M L, Prisic S, Coates R M, Peters R J (2004) Functional identification of rice syn-copalyl diphosphate synthase and its role in initiating biosynthesis of diterpenoid phytoalexin/allelopathic natural products. *Plant J* 39:309-318.
43. Xu M M, Wilderman P R, Peters R J (2007) Following evolution's lead to a single residue switch for diterpene synthase product outcome. *Proc Natl Acad Sci USA* 104:7397-7401.
44. Xu M M, et al. (2007) Functional characterization of the rice kaurene synthase-like gene family. *Phytochemistry* 68:312-326.
45. Cao R, et al. (2010) Diterpene cyclases and the nature of the isoprene fold. *Proteins* 78:2417-2432.
46. Haralampidis K, et al. (2001) A new class of oxidosqualene cyclases directs synthesis of antimicrobial phytoprotectants in monocots. *Proc Natl Acad Sci USA* 98:13431-13436.
47. Lin F-Y, et al. (2010) Mechanism of action and inhibition of dehydrosqualene synthase. *Proc Natl Acad Sci USA* 107:21337-21342.
48. Liu C I, et al. (2008) A cholesterol biosynthesis inhibitor blocks *Staphylococcus aureus* virulence. *Science* 319:1391-1394.
49. Traverse A (1955) Occurrence of the oil-forming alga *Botryococcus* in lignites and other tertiary sediments. *Micropaleontology* 1:343-350.

50. Niehaus, et al. (2011) Identification of unique mechanisms for triterpene biosynthesis in *Botryococcus braunii*. *PNAS* 108(30):12260-12265.
51. Okada S, Devarenne T P, Murakami M, Abe H, Chappell J (2004) Characterization of botryococcene synthase enzyme activity, a squalene synthase-like activity from the green microalga *Botryococcus braunii*, race B. *Arch Biochem Biophys* 422: 110-118.
52. Meyer E, Aglyamova G V, Wang S, Buchanan-Carter J, Abrego D, Colbourne J K, Willis B L, Matz M V (2009) Sequencing and de novo analysis of a coral larval transcriptome using 454 gsflx. BMC Genomics 10.
53. Jandrositz A, Turnowsky F, Hogenauer G (1991) The gene encoding squalene epoxidase from *Saccharomyces cerevisiae*—cloning and characterization. *Gene* 107: 155-160.
54. LL, Kao R, Ivey F D, Hoffman C S (2004) Strategies for gene disruptions and plasmid constructions in fission yeast. *Methods* 33: 199-205.
55. AH, Mao Y F, Hu Y, Sun Q, Yan J (2009) Sensitive and specific elisa coated by tpn15-tpn17-tpn47 fusion protein for detection of antibodies to *Treponema pallidum*. *Clin Chem Lab Med* 47: 321-326.
56. U.S. Pat. No. 7,985,568 for "*Botryococcus brauni* Triterpene Synthase Proteins and Nucelic Acid Molecules, and Method for Their Use" to Chappell, et al.
57. U.S. Patent Application Publication No. 2011/0294182 for "*Botryococcus brauni* Triterpene Synthase Proteins and Nucelic Acid Molecules, and Method for Their Use" to Chappell, et al.
58. U.S. Patent Application Publication No. 2010/0009423 for "*B. braunii*, Race B Gene for a Triterpene Methyltransferase Enzyme and Uses Thereof.

What is claimed is:

1. An isolated polypeptide having triterpene synthase activity wherein the polypeptide comprises peptide domains I, II, III, IV, and V, wherein:
   domain I comprises an amino acid sequence that is at least 95% identical to the amino acid sequence of SEQ ID NO: 17,
   domain II comprises an amino acid sequence that is at least 95% identical to the amino acid sequence of SEQ ID NO: 18,
   domain III comprises an amino acid sequence that is at least 95% identical to the amino acid sequence of SEQ ID NO: 19,
   domain IV comprises an amino acid sequence that is at least 95% identical to the amino acid sequence of SEQ ID NO: 20, and
   domain V comprises an amino acid sequence that is at least 95% identical to the amino acid sequence of SEQ ID NO: 21.

2. The isolated polypeptide of claim 1, wherein
   domain I comprises the amino acid sequence of SEQ ID NO: 17,
   domain II comprises the amino acid sequence of SEQ ID NO: 18,
   domain III comprises the amino acid sequence of SEQ ID NO: 19,
   domain IV comprises the amino acid sequence of SEQ ID NO: 20, and
   domain V comprises the amino acid sequence of SEQ ID NO: 21.

3. The isolated polypeptide of claim 1, which comprises the amino acid sequence of SEQ ID NO: 16.

4. The isolated polypeptide of claim 3, wherein the polypeptide has triterpene synthase activity.

5. The isolated polypeptide of claim 1, which comprises an amino acid sequence that is at least 95% identical to the amino acid sequence of SEQ ID NO: 16.

6. A kit for producing triterpenes, comprising the polypeptide of claim 1 and instructions for using the polypeptide for producing triterpenes.

7. The kit of claim 6, wherein the polypeptide is provided in a container.

* * * * *

SEQUENCE LISTING

```
<160> NUMBER OF SEQ ID NOS: 45

<210> SEQ ID NO 1
<211> LENGTH: 1212
<212> TYPE: DNA
<213> ORGANISM: Artificial Sequence
<220> FEATURE:
<223> OTHER INFORMATION: Synthetic polynucleotide

<400> SEQUENCE: 1
atgactatgc accaagacca cggagtcatg aaagaccttg tcaagcatcc aaatgaattt      60
ccatacttgc tccaactagc tgcaacaacg tacggctcac cggctgcacc gatccccaag     120
gaaccggacc gagctttctg ctacaatact cttcacaccg tttcgaaggg gttccccaga     180
tttgttatga gacttccgca ggaactccaa gatccgatat gcatattcta cctcctgttg     240
cgagcactag acacggtgga ggatgatatg aacctcaaaa gtgagacgaa gatttcactc     300
ctacgcgttt tccatgaaca ctgttcagac aggaactgga gtatgaaaag tgattatggc     360
atatatgcag atctgatgga aagattcccc ctggtcgtat ccgtcttaga gaagctccct     420
cccgccacac agcagacttt cagggagaat gtcaaataca tgggcaatgg catggcagat     480
tttattgata agcagatcct gacagtggat gagtacgacc tctactgcca ctatgtggcc     540
ggcagttgcg gcattgctgt caccaaggtc attgtgcagt tcaaccttgc cacgcctgaa     600
gctgactcct acgactttt caacagtctg ggcctcttgc ttcagaaggc caacatcatc     660
actgactaca atgaagacat caatgaagag cccaggccca ggatgttctg gccccaggag     720
atttggggga agtacgcgga gaagttggct gacttcaatg aacccgaaaa tattgataca     780
gccgtgaagt gcttgaacca catggtcaca gatgcaatgc ggcacattga gccttccctc     840
aaaggcatgg tttatttcac agacaagaca gtctttcggg cgctcgctct tctgctggtc     900
acagcctttg gccatttgtc cactttgtac aacaacccca atgtctttaa agagaaagtg     960
agacagcgga agggaaggat tgcacggctg gtcatgtcat ccaggaatgt accaggcctc    1020
ttccgtacat gcctcaaact cgcaaacaac ttcgagtcca ggtgcaagca agagacggca    1080
aatgatccca ctgtggccat gactatcaag cgcttgcaat ctattcaagc tacatgcaga    1140
gatggcctgg ccaagtatga cacaccctct gggctgaaat ctttctgcgc agccccaact    1200
cccaccaagt ga                                                        1212

<210> SEQ ID NO 2
<211> LENGTH: 403
<212> TYPE: PRT
```

<213> ORGANISM: Artificial
<220> FEATURE:
<223> OTHER INFORMATION: Synthetic polypeptide

<400> SEQUENCE: 2

```
Met Thr Met His Gln Asp His Gly Val Met Lys Asp Leu Val Lys His
1               5                   10                  15

Pro Asn Glu Phe Pro Tyr Leu Leu Gln Leu Ala Ala Thr Thr Tyr Gly
            20                  25                  30

Ser Pro Ala Ala Pro Ile Pro Lys Glu Pro Asp Arg Ala Phe Cys Tyr
        35                  40                  45

Asn Thr Leu His Thr Val Ser Lys Gly Phe Pro Arg Phe Val Met Arg
    50                  55                  60

Leu Pro Gln Glu Leu Gln Asp Pro Ile Cys Ile Phe Tyr Leu Leu Leu
65                  70                  75                  80

Arg Ala Leu Asp Thr Val Glu Asp Asp Met Asn Leu Lys Ser Glu Thr
                85                  90                  95

Lys Ile Ser Leu Leu Arg Val Phe His Glu His Cys Ser Asp Arg Asn
            100                 105                 110

Trp Ser Met Lys Ser Asp Tyr Gly Ile Tyr Ala Asp Leu Met Glu Arg
        115                 120                 125

Phe Pro Leu Val Val Ser Val Leu Glu Lys Leu Pro Pro Ala Thr Gln
    130                 135                 140

Gln Thr Phe Arg Glu Asn Val Lys Tyr Met Gly Asn Gly Met Ala Asp
145                 150                 155                 160

Phe Ile Asp Lys Gln Ile Leu Thr Val Asp Glu Tyr Asp Leu Tyr Cys
                165                 170                 175

His Tyr Val Ala Gly Ser Cys Gly Ile Ala Val Thr Lys Val Ile Val
            180                 185                 190

Gln Phe Asn Leu Ala Thr Pro Glu Ala Asp Ser Tyr Asp Phe Ser Asn
        195                 200                 205

Ser Leu Gly Leu Leu Leu Gln Lys Ala Asn Ile Ile Thr Asp Tyr Asn
    210                 215                 220

Glu Asp Ile Asn Glu Glu Pro Arg Pro Arg Met Phe Trp Pro Gln Glu
225                 230                 235                 240

Ile Trp Gly Lys Tyr Ala Glu Lys Leu Ala Asp Phe Asn Glu Pro Glu
                245                 250                 255

Asn Ile Asp Thr Ala Val Lys Cys Leu Asn His Met Val Thr Asp Ala
            260                 265                 270

Met Arg His Ile Glu Pro Ser Leu Lys Gly Met Val Tyr Phe Thr Asp
        275                 280                 285

Lys Thr Val Phe Arg Ala Leu Ala Leu Leu Val Thr Ala Phe Gly
    290                 295                 300

His Leu Ser Thr Leu Tyr Asn Asn Pro Asn Val Phe Lys Glu Lys Val
305                 310                 315                 320

Arg Gln Arg Lys Gly Arg Ile Ala Arg Leu Val Met Ser Ser Arg Asn
                325                 330                 335

Val Pro Gly Leu Phe Arg Thr Cys Leu Lys Leu Ala Asn Asn Phe Glu
            340                 345                 350

Ser Arg Cys Lys Gln Glu Thr Ala Asn Asp Pro Thr Val Ala Met Thr
        355                 360                 365

Ile Lys Arg Leu Gln Ser Ile Gln Ala Thr Cys Arg Asp Gly Leu Ala
    370                 375                 380

Lys Tyr Asp Thr Pro Ser Gly Leu Lys Ser Phe Cys Ala Ala Pro Thr
```

```
385                 390                 395                 400

Pro Thr Lys

<210> SEQ ID NO 3
<211> LENGTH: 14
<212> TYPE: PRT
<213> ORGANISM: Artificial Sequence
<220> FEATURE:
<223> OTHER INFORMATION: Synthetic polypeptide

<400> SEQUENCE: 3

Leu Pro Gln Glu Leu Gln Asp Pro Ile Cys Ile Phe Tyr Leu
1               5                   10

<210> SEQ ID NO 4
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 4

Leu Arg Ala Leu Asp Thr Val Glu Asp Asp Met Asn Leu Lys Ser Glu
1               5                   10                  15

Thr Lys

<210> SEQ ID NO 5
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 5

Tyr Cys His Tyr Val Ala Gly Ser Cys Gly Ile Ala Val Thr Lys Val
1               5                   10                  15

Ile Val

<210> SEQ ID NO 6
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 6

Gly Leu Leu Leu Gln Lys Ala Asn Ile Ile Thr Asp Tyr Asn Glu Asp
1               5                   10                  15

<210> SEQ ID NO 7
<211> LENGTH: 14
<212> TYPE: PRT
<213> ORGANISM: Artificial Sequence
<220> FEATURE:
<223> OTHER INFORMATION: Synthetic polypeptide

<400> SEQUENCE: 7

Ala Leu Ala Leu Leu Leu Val Thr Ala Phe Gly His Leu Ser
1               5                   10

<210> SEQ ID NO 8
<211> LENGTH: 1398
<212> TYPE: DNA
<213> ORGANISM: Artificial Sequence
<220> FEATURE:
```

<223> OTHER INFORMATION: Synthetic polynucleotide

<400> SEQUENCE: 8

| | | | | | |
|---|---|---|---|---|---|
| atggtgaaac | tcgtcgaggt | tttgcagcac | ccggacgaga | tcgtccccat | cctgcagatg | 60 |
| ttgcataaga | cctaccgcgc | aaagcgcagc | tataaagacc | ctggtctggc | cttttgctac | 120 |
| ggaatgttgc | aacgggtttc | gagaagcttt | tcagtagtta | tacagcagct | gcctgacgaa | 180 |
| ttgcgccatc | caatatgcgt | gttttatctt | attcttcggg | ccctggatac | tgtcgaggat | 240 |
| gacatgaacc | tcccaaatga | agttaaaata | cctcttcttc | gcaccttcca | tgaacatctc | 300 |
| tttgacaggt | cgtggaagct | caaatgtgga | tatggaccgt | atgtagattt | gatggagaac | 360 |
| tatccgctgg | tcacggatgt | cttccttaca | ctctctccag | gcgcacagga | ggtaatccgg | 420 |
| gacagcacgc | gccgcatggg | caatggcatg | gccgacttca | ttggcaagga | tgaggtccac | 480 |
| tcagtagcgg | agtatgatct | gtactgtcac | tatgtggctg | gcttggtcgg | gagtgctgtg | 540 |
| gccaagattt | tgtggacag | cgggctggag | aaggagaatc | tggtcgcaga | ggtggatctg | 600 |
| gccaacaaca | tgggccagtt | cctgcaaaag | accaacgtta | tcgagacta | cttggaggat | 660 |
| attaatgaag | aaccggcccc | taggatgttc | tggccgcggg | agatctgggg | caaatatgcc | 720 |
| caggagctgg | cggacttcaa | ggacccagcc | aatgagaaag | cggcggtaca | gtgcctgaat | 780 |
| cacatggtca | gatgcact | ccgacactgc | gagatcggcc | tgaacgtgat | cccgctgttg | 840 |
| cagaacattg | catcctccg | cagctgcctc | atccccgaag | tcatgggctt | gagaaccctg | 900 |
| accttgtgtt | acaacaatcc | tcaagtcttc | cgagggtgg | tgaagatgcg | gagaggggag | 960 |
| actgccaagc | tgttcatgag | tatctacgac | aagcgctcct | tctaccaaac | atatctccga | 1020 |
| ctcgcgaacg | agttggaagc | aaaatgtaaa | ggggaggcga | gtggagaccc | catggtggcc | 1080 |
| acaacgctga | gcatgtgca | cggaatccag | aagtcatgca | aagccgctct | cagcagcaaa | 1140 |
| gagctgcttg | ccaagtctgg | ctcggccctc | acagacgatc | ccgctatcag | gttgctgctg | 1200 |
| ctggtgggag | tcgtggccta | cttttgcatac | gcattcaact | tggagatgtg | gcggggagag | 1260 |
| cacggggtgc | gggctctggg | ctccattctg | gacctgtccc | agaaaggctt | ggctgtggcg | 1320 |
| agtgtcgctc | tgctgctgct | ggtgcttctg | gccaggagcc | gccttccctt | gctcacctct | 1380 |
| gcttcttcca | agcagtag | | | | | 1398 |

<210> SEQ ID NO 9
<211> LENGTH: 465
<212> TYPE: PRT
<213> ORGANISM: Artificial Sequence
<220> FEATURE:
<223> OTHER INFORMATION: Synthetic polypeptide

<400> SEQUENCE: 9

Met Val Lys Leu Val Glu Val Leu Gln His Pro Asp Glu Ile Val Pro
1               5                   10                  15

Ile Leu Gln Met Leu His Lys Thr Tyr Arg Ala Lys Arg Ser Tyr Lys
            20                  25                  30

Asp Pro Gly Leu Ala Phe Cys Tyr Gly Met Leu Gln Arg Val Ser Arg
        35                  40                  45

Ser Phe Ser Val Val Ile Gln Gln Leu Pro Asp Glu Leu Arg His Pro
    50                  55                  60

Ile Cys Val Phe Tyr Leu Ile Leu Arg Ala Leu Asp Thr Val Glu Asp
65                  70                  75                  80

Asp Met Asn Leu Pro Asn Glu Val Lys Ile Pro Leu Leu Arg Thr Phe
                85                  90                  95

```
His Glu His Leu Phe Asp Arg Ser Trp Lys Leu Lys Cys Gly Tyr Gly
            100                 105                 110

Pro Tyr Val Asp Leu Met Glu Asn Tyr Pro Leu Val Thr Asp Val Phe
            115                 120                 125

Leu Thr Leu Ser Pro Gly Ala Gln Glu Val Ile Arg Asp Ser Thr Arg
            130                 135                 140

Arg Met Gly Asn Gly Met Ala Asp Phe Ile Gly Lys Asp Glu Val His
145                 150                 155                 160

Ser Val Ala Glu Tyr Asp Leu Tyr Cys His Tyr Val Ala Gly Leu Val
                165                 170                 175

Gly Ser Ala Val Ala Lys Ile Phe Val Asp Ser Gly Leu Glu Lys Glu
            180                 185                 190

Asn Leu Val Ala Glu Val Asp Leu Ala Asn Asn Met Gly Gln Phe Leu
            195                 200                 205

Gln Lys Thr Asn Val Ile Arg Asp Tyr Leu Glu Asp Ile Asn Glu Glu
            210                 215                 220

Pro Ala Pro Arg Met Phe Trp Pro Arg Glu Ile Trp Gly Lys Tyr Ala
225                 230                 235                 240

Gln Glu Leu Ala Asp Phe Lys Asp Pro Ala Asn Glu Lys Ala Ala Val
                245                 250                 255

Gln Cys Leu Asn His Met Val Thr Asp Ala Leu Arg His Cys Glu Ile
            260                 265                 270

Gly Leu Asn Val Ile Pro Leu Leu Gln Asn Ile Gly Ile Leu Arg Ser
            275                 280                 285

Cys Leu Ile Pro Glu Val Met Gly Leu Arg Thr Leu Thr Leu Cys Tyr
            290                 295                 300

Asn Asn Pro Gln Val Phe Arg Gly Val Val Lys Met Arg Arg Gly Glu
305                 310                 315                 320

Thr Ala Lys Leu Phe Met Ser Ile Tyr Asp Lys Arg Ser Phe Tyr Gln
                325                 330                 335

Thr Tyr Leu Arg Leu Ala Asn Glu Leu Glu Ala Lys Cys Lys Gly Glu
            340                 345                 350

Ala Ser Gly Asp Pro Met Val Ala Thr Thr Leu Lys His Val His Gly
            355                 360                 365

Ile Gln Lys Ser Cys Lys Ala Ala Leu Ser Ser Lys Glu Leu Leu Ala
            370                 375                 380

Lys Ser Gly Ser Ala Leu Thr Asp Asp Pro Ala Ile Arg Leu Leu Leu
385                 390                 395                 400

Leu Val Gly Val Val Ala Tyr Phe Ala Tyr Ala Phe Asn Leu Gly Asp
                405                 410                 415

Val Arg Gly Glu His Gly Val Arg Ala Leu Gly Ser Ile Leu Asp Leu
            420                 425                 430

Ser Gln Lys Gly Leu Ala Val Ala Ser Val Ala Leu Leu Leu Leu Val
            435                 440                 445

Leu Leu Ala Arg Ser Arg Leu Pro Leu Leu Thr Ser Ala Ser Ser Lys
            450                 455                 460

Gln
465

<210> SEQ ID NO 10
<211> LENGTH: 14
<212> TYPE: PRT
<213> ORGANISM: Artificial Sequence
<220> FEATURE:
```

<223> OTHER INFORMATION: Synthetic polypeptide

<400> SEQUENCE: 10

Leu Pro Asp Glu Leu Arg His Pro Ile Cys Val Phe Tyr Leu
1               5                   10

<210> SEQ ID NO 11
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 11

Leu Arg Ala Leu Asp Thr Val Glu Asp Asp Met Asn Leu Pro Asn Glu
1               5                   10                  15

Val Lys

<210> SEQ ID NO 12
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 12

Tyr Cys His Tyr Val Ala Gly Leu Val Gly Ser Ala Val Ala Lys Ile
1               5                   10                  15

Phe Val

<210> SEQ ID NO 13
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 13

Gly Gln Phe Leu Gln Lys Thr Asn Val Ile Arg Asp Tyr Leu Glu Asp
1               5                   10                  15

<210> SEQ ID NO 14
<211> LENGTH: 14
<212> TYPE: PRT
<213> ORGANISM: Artificial Sequence
<220> FEATURE:
<223> OTHER INFORMATION: Synthetic polypeptide

<400> SEQUENCE: 14

Ser Cys Leu Ile Pro Glu Val Met Gly Leu Arg Thr Leu Thr
1               5                   10

<210> SEQ ID NO 15
<211> LENGTH: 1152
<212> TYPE: DNA
<213> ORGANISM: Artificial Sequence
<220> FEATURE:
<223> OTHER INFORMATION: Synthetic polynucelotide

<400> SEQUENCE: 15
atgaaacttc gggaagtctt gcagcacccg ggtgagatta tccctctcct gcaaatgatg      60
gtcatggcct accgcaggaa gaggaagcct caagatccca atttggcctg gtgctgggag     120
acgctgatta aagtttcgag aagttacgtt ctagtcattc agcagcttcc tgaagtactt     180

```
caggacccta tctgcgtcaa ctatcttgtt cttcgaggct tggacacact gcaggatgac    240
atggcaattc ccgcagagaa gcgggttcca ctcctcctcg actactacaa ccatattgga    300
gacataactt ggaagccgcc ttgcggatat gggcagtatg tggagctgat tgaggagtat    360
ccaagggtga caaagagtt cttgaaactc aacaagcaag atcagcagtt tatcacggac    420
atgtgcatgc ggctgggagc ggagatgaca gtatttctca gagggacgt gttgacagtt    480 cctgacttgg atctgtatgc cttcactaat aacgggccag ttgctatctg cctgaccaag    540
ttatgggtgg acagaaagtt tgcagaccca agcttctgg accgggagga cctatcgggc    600
cacatggcca tgttcttggg caagattaac gtcatccgcg acatcaagga ggatgtcttg    660
gaggatcctc ctcgcatctg gtggccgaag gagatctggg gaaagtacct caaggacctg    720
agggacatca tcaagcctga gtatcaaaag gaagcgctgg cctgtctcaa tgacatcctc    780
acagatgcac tgcgccatat cgagccctgc cttcagtaca tggagatggt ttgggacgag    840
ggcgttttta gttctgcgc cgtgccagag ctcatgtcct ggctaccat ctcggtgtgt    900 tacaacaatc cgaaggtctt cacaggtgtt gtcaagatga ggagggcga aacagcaaag    960 ctgtttctga gcgtaacaaa tatgccagct ctgtacaaga gttttcagc cattgctgaa   1020 gaaatggagg ccaagtgtgt gagggaggat cccaactttg cactcacagt caagcggctt   1080
caggatgtcc aggcgttatg caaggcaggc ctagcaaaat caaatggaaa ggtttcagct   1140
aagggtgctt ag                                                      1152
```

<210> SEQ ID NO 16
<211> LENGTH: 383
<212> TYPE: PRT
<213> ORGANISM: Artificial Sequence
<220> FEATURE:
<223> OTHER INFORMATION: Synthetic polypeptide

<400> SEQUENCE: 16

```
Met Lys Leu Arg Glu Val Leu Gln His Pro Gly Glu Ile Ile Pro Leu
1               5                   10                  15

Leu Gln Met Met Val Met Ala Tyr Arg Arg Lys Arg Lys Pro Gln Asp
            20                  25                  30

Pro Asn Leu Ala Trp Cys Trp Glu Thr Leu Ile Lys Val Ser Arg Ser
        35                  40                  45

Tyr Val Leu Val Ile Gln Gln Leu Pro Glu Val Leu Gln Asp Pro Ile
    50                  55                  60

Cys Val Asn Tyr Leu Val Leu Arg Gly Leu Asp Thr Leu Gln Asp Asp
65                  70                  75                  80

Met Ala Ile Pro Ala Glu Lys Arg Val Pro Leu Leu Asp Tyr Tyr
                85                  90                  95

Asn His Ile Gly Asp Ile Thr Trp Lys Pro Pro Cys Gly Tyr Gly Gln
                100                 105                 110

Tyr Val Glu Leu Ile Glu Glu Tyr Pro Arg Val Thr Lys Glu Phe Leu
            115                 120                 125

Lys Leu Asn Lys Gln Asp Gln Gln Phe Ile Thr Asp Met Cys Met Arg
        130                 135                 140

Leu Gly Ala Glu Met Thr Val Phe Leu Lys Arg Asp Val Leu Thr Val
145                 150                 155                 160

Pro Asp Leu Asp Leu Tyr Ala Phe Thr Asn Asn Gly Pro Val Ala Ile
                165                 170                 175

Cys Leu Thr Lys Leu Trp Val Asp Arg Lys Phe Ala Asp Pro Lys Leu
            180                 185                 190
```

```
Leu Asp Arg Glu Asp Leu Ser Gly His Met Ala Met Phe Leu Gly Lys
        195                 200                 205

Ile Asn Val Ile Arg Asp Ile Lys Glu Asp Val Leu Glu Asp Pro Pro
    210                 215                 220

Arg Ile Trp Trp Pro Lys Glu Ile Trp Gly Lys Tyr Leu Lys Asp Leu
225                 230                 235                 240

Arg Asp Ile Ile Lys Pro Glu Tyr Gln Lys Glu Ala Leu Ala Cys Leu
                245                 250                 255

Asn Asp Ile Leu Thr Asp Ala Leu Arg His Ile Glu Pro Cys Leu Gln
            260                 265                 270

Tyr Met Glu Met Val Trp Asp Gly Val Phe Lys Phe Cys Ala Val
        275                 280                 285

Pro Glu Leu Met Ser Leu Ala Thr Ile Ser Val Cys Tyr Asn Asn Pro
    290                 295                 300

Lys Val Phe Thr Gly Val Val Lys Met Arg Arg Gly Glu Thr Ala Lys
305                 310                 315                 320

Leu Phe Leu Ser Val Thr Asn Met Pro Ala Leu Tyr Lys Ser Phe Ser
                325                 330                 335

Ala Ile Ala Glu Glu Met Glu Ala Lys Cys Val Arg Gly Asp Pro Asn
            340                 345                 350

Phe Ala Leu Thr Val Lys Arg Leu Gln Asp Val Gln Ala Leu Cys Lys
        355                 360                 365

Ala Gly Leu Ala Lys Ser Asn Gly Lys Val Ser Ala Lys Gly Ala
    370                 375                 380

<210> SEQ ID NO 17
<211> LENGTH: 14
<212> TYPE: PRT
<213> ORGANISM: Artificial Sequence
<220> FEATURE:
<223> OTHER INFORMATION: Synthetic polypeptide

<400> SEQUENCE: 17

Leu Pro Glu Val Leu Gln Asp Pro Ile Cys Val Asn Tyr Leu
1               5                   10

<210> SEQ ID NO 18
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 18

Leu Arg Gly Leu Asp Thr Leu Gln Asp Asp Met Ala Ile Pro Ala Glu
1               5                   10                  15

Lys Arg

<210> SEQ ID NO 19
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 19

Tyr Ala Phe Thr Asn Asn Gly Pro Val Ala Ile Cys Leu Thr Lys Leu
1               5                   10                  15

Trp Val
```

```
<210> SEQ ID NO 20
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 20

Ala Met Phe Leu Gly Lys Ile Asn Val Ile Arg Asp Ile Lys Glu Asp
1               5                   10                  15

<210> SEQ ID NO 21
<211> LENGTH: 14
<212> TYPE: PRT
<213> ORGANISM: Artificial Sequence
<220> FEATURE:
<223> OTHER INFORMATION: Synthetic polypeptide

<400> SEQUENCE: 21

Phe Cys Ala Val Pro Glu Leu Met Ser Leu Ala Thr Ile Ser
1               5                   10

<210> SEQ ID NO 22
<211> LENGTH: 461
<212> TYPE: PRT
<213> ORGANISM: Artificial Sequence
<220> FEATURE:
<223> OTHER INFORMATION: Synthetic polypeptide

<400> SEQUENCE: 22

Met Gly Met Leu Arg Trp Gly Val Glu Ser Leu Gln Asn Pro Asp Glu
1               5                   10                  15

Leu Ile Pro Val Leu Arg Met Ile Tyr Ala Asp Lys Phe Gly Lys Ile
                20                  25                  30

Lys Pro Lys Asp Glu Asp Arg Gly Phe Cys Tyr Glu Ile Leu Asn Leu
            35                  40                  45

Val Ser Arg Ser Phe Ala Ile Val Ile Gln Gln Leu Pro Ala Gln Leu
        50                  55                  60

Arg Asp Pro Val Cys Ile Phe Tyr Leu Val Leu Arg Ala Leu Asp Thr
65                  70                  75                  80

Val Glu Asp Asp Met Lys Ile Ala Ala Thr Thr Lys Ile Pro Leu Leu
                85                  90                  95

Arg Asp Phe Tyr Glu Lys Ile Ser Asp Arg Ser Phe Arg Met Thr Ala
            100                 105                 110

Gly Asp Gln Lys Asp Tyr Ile Arg Leu Leu Asp Gln Tyr Pro Lys Val
        115                 120                 125

Thr Ser Val Phe Leu Lys Leu Thr Pro Arg Glu Gln Glu Ile Ile Ala
    130                 135                 140

Asp Ile Thr Lys Arg Met Gly Asn Gly Met Ala Asp Phe Val His Lys
145                 150                 155                 160

Gly Val Pro Asp Thr Val Gly Asp Tyr Asp Leu Tyr Cys His Tyr Val
                165                 170                 175

Ala Gly Val Val Gly Leu Gly Leu Ser Gln Leu Phe Val Ala Ser Gly
            180                 185                 190

Leu Gln Ser Pro Ser Leu Thr Arg Ser Glu Asp Leu Ser Asn His Met
        195                 200                 205

Gly Leu Phe Leu Gln Lys Thr Asn Ile Ile Arg Asp Tyr Phe Glu Asp
    210                 215                 220
```

-continued

Ile Asn Glu Leu Pro Ala Pro Arg Met Phe Trp Pro Arg Glu Ile Trp
225                 230                 235                 240

Gly Lys Tyr Ala Asn Asn Leu Ala Glu Phe Lys Asp Pro Ala Asn Lys
            245                 250                 255

Ala Ala Ala Met Cys Cys Leu Asn Glu Met Val Thr Asp Ala Leu Arg
        260                 265                 270

His Ala Val Tyr Cys Leu Gln Tyr Met Ser Met Ile Glu Asp Pro Gln
    275                 280                 285

Ile Phe Asn Phe Cys Ala Ile Pro Gln Thr Met Ala Phe Gly Thr Leu
290                 295                 300

Ser Leu Cys Tyr Asn Asn Tyr Thr Ile Phe Thr Gly Pro Lys Ala Ala
305                 310                 315                 320

Val Lys Leu Arg Arg Gly Thr Thr Ala Lys Leu Met Tyr Thr Ser Asn
            325                 330                 335

Asn Met Phe Ala Met Tyr Arg His Phe Leu Asn Phe Ala Glu Lys Leu
        340                 345                 350

Glu Val Arg Cys Asn Thr Glu Ser Glu Asp Pro Ser Val Thr Thr
    355                 360                 365

Thr Leu Glu His Leu His Lys Ile Lys Ala Ala Cys Lys Ala Gly Leu
370                 375                 380

Ala Arg Thr Lys Asp Asp Thr Phe Asp Glu Leu Arg Ser Arg Leu Leu
385                 390                 395                 400

Ala Leu Thr Gly Gly Ser Phe Tyr Leu Ala Trp Thr Tyr Asn Phe Leu
            405                 410                 415

Asp Leu Arg Gly Pro Gly Asp Leu Pro Thr Phe Leu Ser Val Thr Gln
        420                 425                 430

His Trp Trp Ser Ile Leu Ile Phe Leu Ile Ser Ile Ala Val Phe Phe
    435                 440                 445

Ile Pro Ser Arg Pro Ser Pro Arg Pro Thr Leu Ser Ala
450                 455                 460

<210> SEQ ID NO 23
<211> LENGTH: 14
<212> TYPE: PRT
<213> ORGANISM: Artificial Sequence
<220> FEATURE:
<223> OTHER INFORMATION: Synthetic polypeptide

<400> SEQUENCE: 23

Leu Pro Ala Gln Leu Arg Asp Pro Val Cys Ile Phe Tyr Leu
1               5                   10

<210> SEQ ID NO 24
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 24

Leu Arg Ala Leu Asp Thr Val Glu Asp Asp Met Lys Ile Ala Ala Thr
1               5                   10                  15

Thr Lys

<210> SEQ ID NO 25
<211> LENGTH: 18
<212> TYPE: PRT
<213> ORGANISM: Artificial Sequence
<220> FEATURE:

```
<223> OTHER INFORMATION: Synthetic polypeptide

<400> SEQUENCE: 25

Tyr Cys His Tyr Val Ala Gly Val Val Gly Leu Gly Leu Ser Gln Leu
1               5                   10                  15

Phe Val

<210> SEQ ID NO 26
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 26

Gly Leu Phe Leu Gln Lys Thr Asn Ile Ile Arg Asp Tyr Phe Glu Asp
1               5                   10                  15

<210> SEQ ID NO 27
<211> LENGTH: 14
<212> TYPE: PRT
<213> ORGANISM: Artificial Sequence
<220> FEATURE:
<223> OTHER INFORMATION: Synthetic polypeptide

<400> SEQUENCE: 27

Phe Cys Ala Ile Pro Gln Thr Met Ala Phe Gly Thr Leu Ser
1               5                   10

<210> SEQ ID NO 28
<211> LENGTH: 38
<212> TYPE: DNA
<213> ORGANISM: Artificial Sequence
<220> FEATURE:
<223> OTHER INFORMATION: synthetic

<400> SEQUENCE: 28
ccggaattca aaacaatgac tatgcaccaa gaccacgg                            38

<210> SEQ ID NO 29
<211> LENGTH: 59
<212> TYPE: DNA
<213> ORGANISM: Artificial Sequence
<220> FEATURE:
<223> OTHER INFORMATION: synthetic

<400> SEQUENCE: 29
accagaacca ccaccagaac caccaccaga accacccttg gtgggagttg gggctgcgc     59

<210> SEQ ID NO 30
<211> LENGTH: 58
<212> TYPE: DNA
<213> ORGANISM: Artificial Sequence
<220> FEATURE:
<223> OTHER INFORMATION: Synthetic

<400> SEQUENCE: 30
ggtggttctg gtggtggttc tggtggtggt tctggtatga aacttcggga agtcttgc      58

<210> SEQ ID NO 31
<211> LENGTH: 38
<212> TYPE: DNA
<213> ORGANISM: Artificial Sequence
<220> FEATURE:
<223> OTHER INFORMATION: synthetic
```

<400> SEQUENCE: 31
ataagaatgc ggccgcctaa gcacccttag ctgaaacc                                  38

<210> SEQ ID NO 32
<211> LENGTH: 38
<212> TYPE: DNA
<213> ORGANISM: Artificial Sequence
<220> FEATURE:
<223> OTHER INFORMATION: synthetic

<400> SEQUENCE: 32
ccggaattca aaacaatgac tatgcaccaa gaccacgg                                  38

<210> SEQ ID NO 33
<211> LENGTH: 38
<212> TYPE: DNA
<213> ORGANISM: Artificial Sequence
<220> FEATURE:
<223> OTHER INFORMATION: synthetic

<400> SEQUENCE: 33
ataagaatgc ggccgcctaa gcacccttag ctgaaacc                                  38

<210> SEQ ID NO 34
<211> LENGTH: 40
<212> TYPE: DNA
<213> ORGANISM: Artificial Sequence
<220> FEATURE:
<223> OTHER INFORMATION: synthetic

<400> SEQUENCE: 34
cgggaattca aaacaatgaa acttcgggaa gtcttgcagc                                40

<210> SEQ ID NO 35
<211> LENGTH: 60
<212> TYPE: DNA
<213> ORGANISM: Artificial Sequence
<220> FEATURE:
<223> OTHER INFORMATION: synthetic

<400> SEQUENCE: 35
accagaacca ccaccagaac caccaccaga accaccagca cccttagctg aaacctttcc          60

<210> SEQ ID NO 36
<211> LENGTH: 59
<212> TYPE: DNA
<213> ORGANISM: Artificial Sequence
<220> FEATURE:
<223> OTHER INFORMATION: synthetic

<400> SEQUENCE: 36
ggtggttctg gtggtggttc tggtggtggt tctggtatga ctatgcacca agaccacgg           59

<210> SEQ ID NO 37
<211> LENGTH: 42
<212> TYPE: DNA
<213> ORGANISM: Artificial Sequence
<220> FEATURE:
<223> OTHER INFORMATION: synthetic

<400> SEQUENCE: 37
ataagaatgc ggccgcttac ttggtgggag ttggggctgc gc                             42

<210> SEQ ID NO 38
<211> LENGTH: 38

-continued

<212> TYPE: DNA
<213> ORGANISM: Artificial Sequence
<220> FEATURE:
<223> OTHER INFORMATION: synthetic

<400> SEQUENCE: 38
cgcggatcca aaacaatgac tatgcaccaa gaccacgg                               38

<210> SEQ ID NO 39
<211> LENGTH: 44
<212> TYPE: DNA
<213> ORGANISM: Artificial Sequence
<220> FEATURE:
<223> OTHER INFORMATION: synthetic

<400> SEQUENCE: 39
gcgctaacaa cttggtggga gttggggctg cgcagaaaga tttc                       44

<210> SEQ ID NO 40
<211> LENGTH: 42
<212> TYPE: DNA
<213> ORGANISM: Artificial Sequence
<220> FEATURE:
<223> OTHER INFORMATION: synthetic

<400> SEQUENCE: 40
ctcccaccaa gttgttagcg ctgacgggag gcagcttcta cc                         42

<210> SEQ ID NO 41
<211> LENGTH: 41
<212> TYPE: DNA
<213> ORGANISM: Artificial Sequence
<220> FEATURE:
<223> OTHER INFORMATION: synthetic

<400> SEQUENCE: 41
ataaagaatg cggccgctta ggcgctgagt gtgggtctag g                          41

<210> SEQ ID NO 42
<211> LENGTH: 40
<212> TYPE: DNA
<213> ORGANISM: Artificial Sequence
<220> FEATURE:
<223> OTHER INFORMATION: synthetic

<400> SEQUENCE: 42
cgggaattca aaacaatgaa acttcgggaa gtcttgcagc                            40

<210> SEQ ID NO 43
<211> LENGTH: 45
<212> TYPE: DNA
<213> ORGANISM: Artificial Sequence
<220> FEATURE:
<223> OTHER INFORMATION: synthetic

<400> SEQUENCE: 43
cgtcaaaggt agcaccctta gctgaaacct ttccatttga ttttg                      45

<210> SEQ ID NO 44
<211> LENGTH: 45
<212> TYPE: DNA
<213> ORGANISM: Artificial Sequence
<220> FEATURE:
<223> OTHER INFORMATION: synthetic

<400> SEQUENCE: 44

```
gctaagggtg ctacctttga cgaattgagg agcaggttgt tagcg                45
```

<210> SEQ ID NO 45
<211> LENGTH: 41
<212> TYPE: DNA
<213> ORGANISM: Artificial Sequence
<220> FEATURE:
<223> OTHER INFORMATION: synthetic

<400> SEQUENCE: 45

```
ataaagaatg cggccgctta ggcgctgagt gtgggtctag g                    41
```